US006156555A

United States Patent [19]

Iida et al.

[11] Patent Number: 6,156,555

[45] Date of Patent: Dec. 5, 2000

[54] METHOD OF PREPARING AN ENZYME PARTICIPATING IN C-TERMINAL AMIDATION

[75] Inventors: Toshii Iida; Toshihiko Kaminuma; Yuka Fuse; Masahiro Tajima; Mitsuo Yanagi, all of Yokohama; Hiroshi Okamoto, Sendai; Jiro Kishimoto; Ohji Ifuku, both of Yokohama; Ichiro Kato, Sendai, all of Japan

[73] Assignee: Shiseido Company Ltd., Tokyo, Japan

[21] Appl. No.: 09/172,120

[22] Filed: Oct. 14, 1998

Related U.S. Application Data

[62] Division of application No. 08/070,301, filed as application No. PCT/JP90/01036, Aug. 14, 1990, Pat. No. 5,871,995.

[30] Foreign Application Priority Data

| | | | |
|---|---|---|---|
| Aug. 15, 1989 | [JP] | Japan | 1-209687 |
| Oct. 31, 1989 | [JP] | Japan | 1-281933 |
| Mar. 26, 1990 | [JP] | Japan | 2-076331 |
| Apr. 24, 1990 | [JP] | Japan | 2-106412 |
| Aug. 2, 1990 | [JP] | Japan | 2-205475 |

[51] Int. Cl.[7] .............................. C12N 9/48; C12N 9/14; C12N 9/78; C12N 9/80; C12N 15/00

[52] U.S. Cl. ............................. 435/212; 435/18; 435/24; 435/69.1; 435/195; 435/227; 435/228; 435/471; 435/814; 435/815

[58] Field of Search .................................... 435/212, 195, 435/227, 228, 471, 18, 24, 69.1, 814, 815

[56] References Cited

U.S. PATENT DOCUMENTS

| | | | |
|---|---|---|---|
| 4,693,985 | 9/1987 | Degen et al. | 436/531 |
| 4,780,934 | 11/1988 | Gilligan et al. | 435/68 |

FOREIGN PATENT DOCUMENTS

| | | |
|---|---|---|
| 0 308 067 | 3/1989 | European Pat. Off. . |
| 0 447 547 | 9/1991 | European Pat. Off. . |
| 0 465 404 B1 | 1/1992 | European Pat. Off. . |
| 3-262484 | 11/1991 | Japan . |
| PCT/US88/ 03172 | 3/1989 | WIPO . |
| WO 89/02460 | 3/1989 | WIPO . |

OTHER PUBLICATIONS

Young et al., "Enzymatic Peptidyl α–Amidation Proceeds through Formation of an α–Hydroxyglycine Intermediate", J. Am. Chem. Soc., vol. 111, No. 5, Mar. 1989, p. 1933–34.

A. Bradbury et al., "Mechanism of C–terminal amide Formation By Pituitary Enzymes," Nature, vol. 298, Aug. 12, 1982, p. 686–688.

K. Ohsuye et al., "Cloning of cDNA Encoding A New Peptide C–Terminal α–Amidating Enzyme . . . ," BBRC, vol. 150, Feb. 15, 1988, p. 1275–1281.

K. Mizuno et al., "Peptide C–Terminal α–Amidating Enzyme Purified to Homogeneity . . . ," BBRC, vol. 137, Jun. 30, 1986, p. 984–991.

A. Katopodis et al., "A Novel Enzyme from Bovine Neurointermediate Pituitary Catalyzes Dealkylation of α–Hydroxyglucine Derivatives, Thereby Functioning Sequentially with Peptidylglycine α–Amidating Monooxygenase in Peptide Amidation", Biochemistry, vol. 29, No. 26, Jul. 3, 1990, p. 6115–6120.

K. Takahashi et al., "Peptidylglycine α–Amidating Reaction: Evidence for A Two–Step Mechanism Involving a Stable Intermediate at Neutral pH", Biochemical and Biophysical Research Communications, vol. 169, No. 2, Jun. 15, 1990, p. 524–530.

J. Glauder et al., "Human Peptidylglycime α–Amidating Monooxygenase: cDNA, Cloning and Functional Expression of a Truncated Form in Cos Cells", Biochemical and Biophysical Research Communications, vol. 169, No. 2, Jun. 15, 1990, p. 551–558.

A. Murthy et al., "Purification and Characterization of Peptidylglycine α–Amidating Monooxygesase from Bovine Neurointermediate Pituitary", The Journal of Biological Chemistry, vol. 261, No. 1., Feb. 5, 1986, p. 1815–1822.

Eipper et al. "Structure of the Precursor to an Enzyme Mediating COOH–Terminal Amidation in Peptide Biosynthesis", *Molecular Endocrinology*, vol. 1, No. 11, pp. 777–790 (1987).

Stoffers et al. "Alternative mRNA splicing generates multiple forms of peptidyl–glycine α–amidating monooxygenase in rat atrium", *Proc. Natl' Acad. Sci. USA*, vol. 86, pp. 735–739 (Jan. 1989).

Tajima et al. "The Reaction Product of Peptidylglycine α–Amidating Enzyme Is a Hydroxyl Derivative at α–Carbon of the Carboxyl–terminal Glycine*", *The Journal of Biological Chemistry*, vol. 265, No. 17, pp. 9602–9605, Issue of Jun. 15, 1990.

Biochemical and Biophysical Research Communication vol. 151, No. 1 (1988), A.G. Katopodis et al.

*Primary Examiner*—David M. Naff
*Attorney, Agent, or Firm*—Foley & Lardner

[57] ABSTRACT

A purified enzyme-I is obtained that participates in C-terminal amidation by acting on a peptide C-terminal glycine adduct to form a peptide C-terminal α-hydroxyglycine adduct. The enzyme has an optimum pH of about 5 to 7, an optimum temperature of 25 to 40° C. and a molecular weight of about 25 kDa or about 36 kDa, and metal ions and ascorbic acid act as a cofactor. A purified enzyme-II is obtained that participates in C-terminal amidation by acting on the peptide C-terminal α-hydroxyglycine adduct to produce a C-terminal amidated compound. The enzyme has an optimum pH of about 5 to 6, an optimum temperature of 15 to 35° C. and a molecular weight of about 40 kDa or about 43 kDa. Enzyme-I does not act on the peptide C-terminal α-hydroxyglycine adduct and enzyme-II does not act on the peptide C-terminal glycine adduct. The enzymes may be purified from a biological material such as horse serum by affinity chromatography using a peptide C-terminal glycine adduct as a ligand. The enzymes may also be obtained from host cells transformed with a plasmid containing a cDNA coding for the enzymes. Assay of activity of the enzymes is carried out by measuring the C-terminal α-hydroxyglycine adduct or the C-terminal amidated compound that has been isolated such as by high performance liquid chromatography with the use of an acetonitrile-containing buffer.

5 Claims, 49 Drawing Sheets

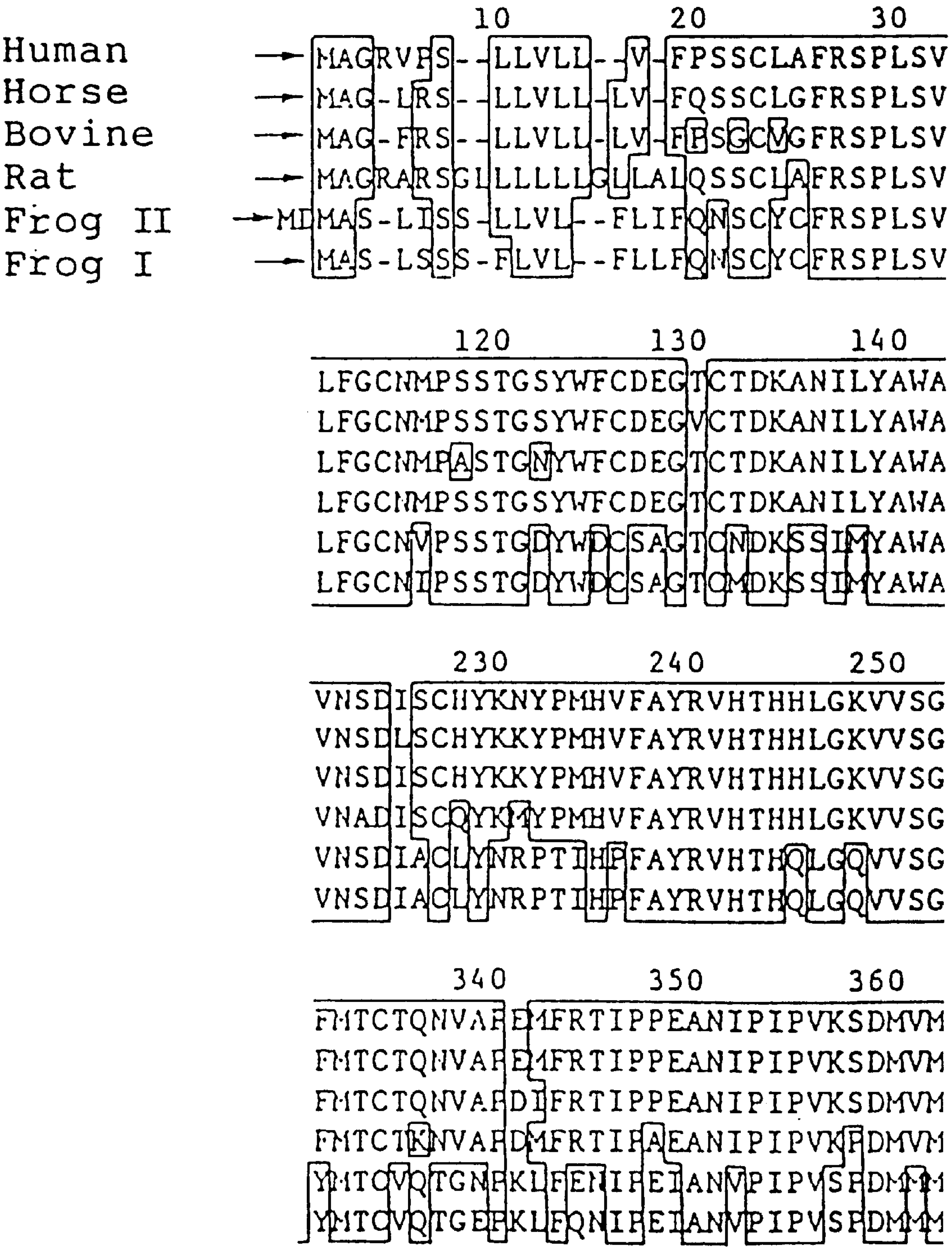

FIG. 5A

```
                        10           20           30
Human     → MAGRVPS--LLVLL--V-FPSSCLAFRSPLSV
Horse     → MAG-LRS--LLVLL-LV-FQSSCLGFRSPLSV
Bovine    → MAG-FRS--LLVLL-LV-FPSGCVGFRSPLSV
Rat       → MAGRARSGLLLLLLGLLALQSSCLAFRSPLSV
Frog II   →MDMAS-LISS-LLVL--FLIFQNSCYCFRSPLSV
Frog I    → MAS-LSSS-FLVL--FLLFQNSCYCFRSPLSV

              120          130          140
          LFGCNMPSSTGSYWFCDEGTCTDKANILYAWA
          LFGCNMPSSTGSYWFCDEGVCTDKANILYAWA
          LFGCNMPASTGNYWFCDEGTCTDKANILYAWA
          LFGCNMPSSTGSYWFCDEGTCTDKANILYAWA
          LFGCNVPSSTGDYWDCSAGTQNDKSSIMYAWA
          LFGCNIPSSTGDYWDCSAGTQMDKSSIMYAWA

              230          240          250
          VNSDISCHYKNYPMHVFAYRVHTHHLGKVVSG
          VNSDLSCHYKKYPMHVFAYRVHTHHLGKVVSG
          VNSDISCHYKKYPMHVFAYRVHTHHLGKVVSG
          VNADISCQYKMYPMHVFAYRVHTHHLGKVVSG
          VNSDIACLYNRPTIHPFAYRVHTHQLGQVVSG
          VNSDIACLYNRPTIHPFAYRVHTHQLGQVVSG

              340          350          360
          FMTCTQNVAPEMFRTIPPEANIPIPVKSDMVM
          FMTCTQNVAPEMFRTIPPEANIPIPVKSDMVM
          FMTCTQNVAPDMFRTIPPEANIPIPVKSDMVM
          FMTCTKNVAPDMFRTIPAEANIPIPVKSDMVM
          YMTCVQTGNPKLFENIPEIANVPIPVSPDMMM
          YMTCVQTGEPKLFQNIPEIANVPIPVSPDMMM
```

FIG. 5B

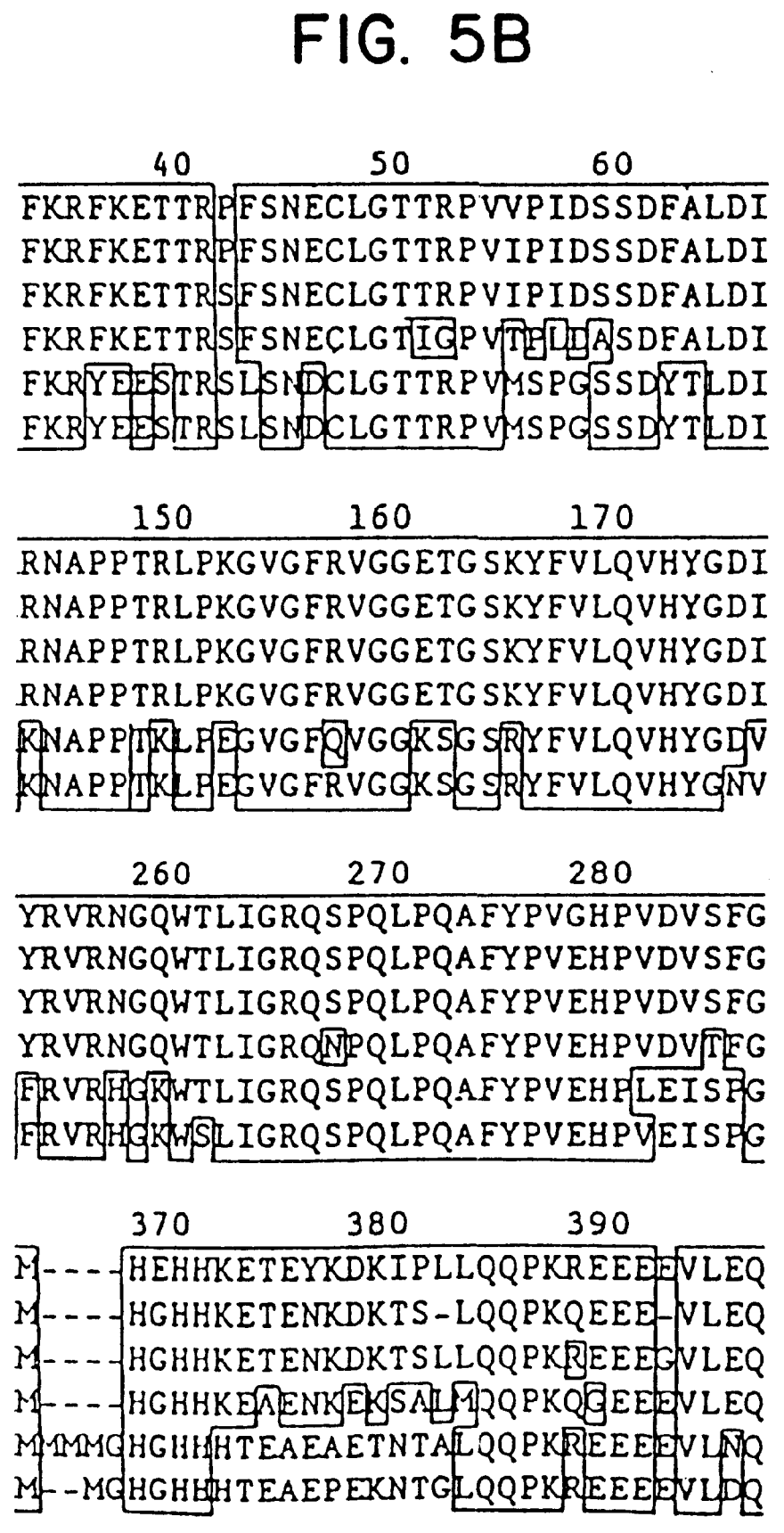

```
     40                  50                  60
FKRFKETTRPFSNECLGTTRPVVPIDSSDFALDI
FKRFKETTRPFSNECLGTTRPVIPIDSSDFALDI
FKRFKETTRSFSNECLGTTRPVIPIDSSDFALDI
FKRFKETTRSFSNECLGTIGPVTELDASDFALDI
FKRYEESTRSLSNDCLGTTRPVMSPGSSDYTLDI
FKRYEESTRSLSNDCLGTTRPVMSPGSSDYTLDI

     150                 160                 170
RNAPPTRLPKGVGFRVGGETGSKYFVLQVHYGDI
RNAPPTRLPKGVGFRVGGETGSKYFVLQVHYGDI
RNAPPTRLPKGVGFRVGGETGSKYFVLQVHYGDI
RNAPPTRLPKGVGFRVGGETGSKYFVLQVHYGDI
KNAPPTKLPEGVGFQVGGKSGSRYFVLQVHYGDV
KNAPPTKLPEGVGFRVGGKSGSRYFVLQVHYGNV

     260                 270                 280
YRVRNGQWTLIGRQSPQLPQAFYPVGHPVDVSFG
YRVRNGQWTLIGRQSPQLPQAFYPVEHPVDVSFG
YRVRNGQWTLIGRQSPQLPQAFYPVEHPVDVSFG
YRVRNGQWTLIGRQNPQLPQAFYPVEHPVDVTFG
FRVRHGKWTLIGRQSPQLPQAFYPVEHPLEISPG
FRVRHGKWSLIGRQSPQLPQAFYPVEHPVEISPG

     370                 380                 390
M----HEHHKETEYKDKIPLLQQPKREEEEVLEQ
M----HGHHKETENKDKTS-LQQPKQEEE-VLEQ
M----HGHHKETENKDKTSLLQQPKREEEGVLEQ
M----HGHHKEAENKEKSALMQQPKQGEEEVLEQ
MMMMGHGHHHTEAEAETNTALQQPKREEEEVLNQ
M--MGHGHHHTEAEPEKNTGLQQPKREEEEVLDQ
```

FIG. 5C

```
  70        80        90        100       110
RMPGVTPKQSDTYFCMSMRIPVDEEAFVIDFKPRASMDTVHHML
RHPGVTPKQSDTYFCMSMRLPMDEETFVIDFKPRASMDTVHHML
RMPGVTPKQSDTYFCMSVRLPMDEEAFVIDFKPRASMDTVHHML
RMPGVTPKESDTYFCMSMRLPVDEEAFVIDFKPRASMDTVHHML
RMPGVTPTESDTYLCKSYRLPVDDEAYVVDYRPHANMDTAHHML
RMPGVTPTESDTYLCKSYRLPVDDEAYVVDFRPHANMDTAHHML

 180       190       200       210       220
SAFRDNNKDCSGVSLHLTRLPQPLIAGMYLMMSVDTVIPAGEKV
SAFRDNHKDCSGVSLHLTRLPQPLIAGMYLMMALDTVIPAGEKV
SAFRDNHKDCSGVSLHLTRLPQPLIAGMYLMMSVDTVIPPGGKV
SAFRDNHKDCSGVSVHLTRVPQPLIAGMYLMMSVDTVIPPGEKV
KAFQDKHKDCTGVTVRITPEKQPLIAGIYLSMSLNTVVPPGQEV
KAFQDKHKDCTGVTVRVTPEKQPQIAGIYLSMSVDTVIPPGEEA

 290       300       310       320       330
DLLAARCVFIGEGRTEATHIGGTSSDEMCNLYIMYYMEAKHAVS
DILAARCVFTGEGRTEATHIGGTSSDEMCNLYIMYYMEAKHAVS
DILAARCVFTGEGRTEVTHIGGTSSDEMCNLYIMYYMEAKHAVS
DILAARCVFTGEGRTEATHIGGTSSDEMCNLYIMYYMEAKYALS
DIIATRCLFTGKGRMSATYIGGTAKDEMCNLYIMYYMDAAHATS
DIIATRCLFTGKGRTSATYIGGTSNDEMCNLYIMYYMDAAHATS

 400       410       420       430       440
GDFYSLLSKLLGEREDVVHVHKYNPTEKAESESDLVAEIANVVQ→Human
GDFYSLLSKLLGEREDVVHVHKYNPTEKAESESDLVAEIANVVQ→Horse
GDFYSLLSKLLGEREDVVHVHKYNPTEKAESESDLVAEIANVVQ→Bovine
GDFYSLLSKLLGERED-VHVHKYNPTEKTESGSDLVAEIANVVQ→Rat
--------------------------------------------→Frog II
GLITLGDSAV→Frog
```

FIG. 5D

```
                    450        460        470
Human    -KKDLGRSDAREGAE-HE-RGNAILVRDRIHKFH
Horse    -KKDLGRSDARESAE-HEDRGNAILVRDRIHKFH
Bovine   -KKDLGRSDIRESAE-QE-RGNAILVRDRIHKFH
Rat      -KKDLGRSDAREGAEHEE-WGNAILVRDRIHRFH
Frog II  ---------------------------------

                    560        570        580
          FDSKFVYQQIGLGPIEEDTILVIDPNNAAVLQS
          FDSKFVYQQRGLGPIEEDTILVIDPNNAAVLQS
          FDSKFVYQQRGLGPIEEDTILVIDPNNAAVLQS
          FDSKFVYQQRGLGPIEEDTILVIDPNNAEILQS
          FDRNFVYQQRGTGPIQESTILVVDPNTSKVLKS

                    670        680        690
          GYCNSRIVQFSPSGKFITQWGEESSGSSPLPGQ
          GYCNSRIVQFSPTGRFITQWGEESSESNPKPGQ
          GYCNSRLVQFSPSGKFITHWGEASQESSPKPGQ
          GYCNSRIVQFSPSGKFMTQWGEESSGSSPRPGQ
          GYCNSRIMQFSPNGMFIMQWGEETSSNLPRPGQ

                    780        790        800
          FVMNFSNGEIIDIFKPVRKHFDMPHDIVASEDG
          FVMNFSSGEIIDVFKPVRKHFDMPHDITASEDG
          FVMNFSSGEIIDVFKPVRKHFDMPHDIAASEDG
          FVMNFSSGEIIDVFKPVRKHFDMPHDIVASEDG
          FMINFSNGDILDTFTPARKNFEMPHDIAAGDDG

                    890        900        910
          VLITTLLVIPVVVLLAIAIFIRWKKSR-AFGDS
          VLITTLLVIPVVVLLAIAIFIRWKKSR-AFCES
          VLITTLLVIPVVVLLAIALFIRWKKSR-AFGDS
          VLITTLLVIPVLVLLAIVMFIRWKKSR-AFGDH
          VLIITLLIIPVVVLTAIAIFIRWRKVRMYGGDI
```

FIG. 5E

```
        480          490          500          510
RLVSTLRPPESRVFSLQQPPPGEGTWEPEHTGDFHMEEALDW
RLESTLRPTESRVISVPQPLPGEGTWEPEHTGDFHVEEALDW
RLVSTLRPAESRVLSLQQPLPGEGTWEPEHTGDFHVEEALDW
RLESTLRPAESRAFSFQQ--PGEGPWEPEPSGDFHVEEELDW
-----------------------------------DVHLEEDTDW

        590          600          610          620
SEKNLFYLPHGLSIDKDGNYWVTDVALHQVFKLDPNNKEGPV
SGKNLFYLPHGLSIDKDGNYWVTDVALHQVFKLDPNSKEGPL
SGKNLFYLPHGLSIDKDGNYWVTDVALHQVFKLDPKSKEGPL
SGKNLFYLPHGLSIDTDGNYWVTDVALHQVFKLDPHSKEGPL
TGQNLFFLPHGLTIDRDGNYWVTDVALHQVFK-VGAEKETPL

        700          710          720          730
FTVPHSLALVPLLGQLCVADRENGRIQCFKTDTKEEVREIKH
FRVPHSLALVPHLGQLCVADRENGRIQCFKTDTKEFVREIKH
FRVPHSLALVPPLGQLCVADRENGRIQCFKTDTKEFVREIKH
FSVPHSLALVPHLQQLCVADRENGRIQCFKTDTKEFVREIKH
FRIPHSLTMISDQGQLCVADRENGRIQCFHAKTGEFVKQIKH

        810          820          830          840
TVYIGDAHTNTVWKFTLTEKLEHRSVKKAGIEVQEIKEAEAV
TVYVGDAHTNTVWKFTSTERVEHRSVKKAGIEVQEIKESEAV
TVYVGDAHTNTVWKFTSTEKMEHRSVKKAGIEVQEIKESEAV
TVYIGDAHTNTVWKFTLTEKMEHRSVKKAGIEVQEIKEAEAV
TVYVGDAHANAVWKF-SPSKAEHRSVKKAGIEVEEIFETEFI

        920          930          940          950
EHKLETSSGRVLGRFRGKGSGGLNLGNFFASRKGYSRKGFDR
EHKVEASSGRVLGRLRGKGSGGLNLGNFFASRKGYSRKGFDR
ERKLEASSGRVLGRLRGKGGGGLNLGNFFASRKGYSRKGFDR
DRKLESSSGRVLGRFRGKGSGGLNLGNFFASRKGYSRKGFDR
GHKSESSSGGILGKLRGKGSGGLNLGTFFATHKGYSRKGFDR
```

FIG. 5F

```
  520         530         540         550
PGVYLLPGQVSGVALDPKNNLVIFHRGDHVWDGNS
PGVYLLPGQVSGVALDLQNNLVIFHRGDHVWDGNS
PGVYLLPGQVSGVALDPQNNLVIFHRGDHVWDGNS
PGVYLLPGQVSGVALDSKNNLVIFHRGDHVWDGNS
PGVNLKVGQVSGLALDPKNNLVIFHRGDHVWDENS

  630         640         650         660
LILGRSMQPGSDQNHFCQPTDVAVDPGTGAIYVSD
LILGRSMQPGSDQNHFCQPTDVAVDPNTGTIFVSD
LFLGRSMQPGSDQNHFCQPTDVAVDPDTGTIYVSD
LILGRSMQPGSDQNHFCQPTDVAVEPSTGAVFVSD
LVLGRAFQPGSDRKHFCQPTDVAVDPITGNFFVAD

  740         750         760         770
SSFGRNVFAISYIP-GLLFAVNGKPHFGDQEPVQG
ASFGRNVFAISYIP-GLLFAVNGKPYFGDQKPVQG
PSFGRNVFAISYIP-GLLFAVNGKPYFEDQEPVQG
ASFGRNVFAISYIP-GFLFAVNGKPYFGDQEPVQG
QEFGREVFAVSYAPGGVLYAVNGKPYFGDSTPVQG

  850         860         870         880
VETKM--ENKPTSSELQKMQEKQKLIKEPGSGVPV
VETKM--ENKPASSELQKMQEKQKLIKEPGSGVPV
VETKM--ENKPASSELQKIQEKQKLVKEPGSGVPA
VEPKV--ENKPTSSELQKMQEKQKLSTEPGSGVSV
FETHMRSRPKTNESVGQQTQEKPSVVQESSAGVSF

  960         970         980         990
LSTEGSDQEK--EDDGSESEEEYSAPLPALAPSSS → Human
LSTEGSDQEK-DEDDGSESEEEYSAPLPAPVPSSS → Horse
LSTEGSDQEK-DE-DASESEEEYSAPPPAPAPSS  → Bovine
VSTEGSDQEK-DEDDGTESEEEYSAPLPKPAPSS  → Rat
LSTEGSDQQKDDDDGSDSEEEYSAPPIPPV-SSS → Frog II
```

FIG. 6A

CATGGCCGGACGCGCCCGCAGCGGTCTGCTACTGCTGCTGCTGGGGCTG
MetAlaGlyArgAlaArgSerGlyLeuLeuLeuLeuLeuLeuGlyLeu
10
TCTGTCTTTAAGAGGTTTAAAGAAACTACCAGATCATTTTCCAATGAA
SerValPheLysArgPheLysGluThrThrArgSerPheSerAsnGlu
40
GATTTTGCGCTGGATATTCGCATGCCTGGGGTTACACCTAAAGAGTCT
AspPheAlaLeuAspIleArgMetProGlyValThrProLysGluSer
70
GAAGCCTTCGTGATTGACTTCAAGCCTCGTGCCAGCATGGATACTGTC
GluAlaPheValIleAspPheLysProArgAlaSerMetAspThrVal
100
GGAAGTTACTGGTTTTGTGATGAAGGAACCTGTACAGATAAAGCCAAT
GlySerTyrTrpPheCysAspGluGlyThrCysThrAspLysAlaAsn
130
CCGAAAGGTGTTGGATTCAGAGTTGGAGGAGAAACTGGAAGCAAATAC
ProLysGlyValGlyPheArgValGlyGlyGluThrGlySerLysTyr
160
GATAATCACAAAGACTGCTCTGGCGTGTCCGTACATCTCACACGTGTG
AspAsnHisLysAspCysSerGlyValSerValHisLeuThrArgVal
190

GACACTGTCATACCACCAGGAGAGAAAGTAGTGAATGCTGACATTTCG
AspThrValIleProProGlyGluLysValValAsnAlaAspIleSer
220
GTCCACACTCACCATTTAGGTAAGGTGGTGAGCGGATACAGAGTAAGA
ValHisThrHisHisLeuGlyLysValValSerGlyTyrArgValArg
250
CCACAGGCTTTCTACCCTGTGGAACACCCCGTTGATGTTACTTTTGGT
ProGlnAlaPheTyrProValGluHisProValAspValThrPheGly
280
ACAGAGGCCACCCACATCGGCGGCACTTCTAGTGACGAAATGTGTAAC
ThrGluAlaThrHisIleGlyGlyThrSerSerAspGluMetCysAsn
310

FIG. 6B

```
CTCGCCCTGCAGAGCAGCTGCCTGGCCTTCAGAAGCCCACTT        90
LeuAlaLeuGlnSerSerCysLeuAlaPheArgSerProLeu
            20                            30
TGCCTTGGTACCATTGGACCAGTCACCCCTCTTGATGCATCA       180
CysLeuGlyThrIleGlyProValThrProLeuAspAlaSer
            50                            60
GACACATACTTCTGCATGTCCATGCGTCTGCCTGTGGATGAG       270
AspThrTyrPheCysMetSerMetArgLeuProValAspGlu
            80                            90
CACCATATGCTGCTGTTTGGATGCAATATGCCCTCGTCCACT       360
HisHisMetLeuLeuPheGlyCysAsnMetProSerSerThr
           110                           120
ATTCTATATGCCTGGGCAAGGAATGCTCCCCCCACCCGGCTC       450
IleLeuTyrAlaTrpAlaArgAsnAlaProProThrArgLeu
           140                           150
TTCGTCCTTCAAGTTCACTATGGCGATATCAGTGCTTTTCGA       540
PheValLeuGlnValHisTyrGlyAspIleSerAlaPheArg
           170                           180
CCCCAGCCTTTAATTGCGGGCATGTACCTTATGATGTCTGTT       630
ProGlnProLeuIleAlaGlyMetTyrLeuMetMetSerVal
           200                           210

TGCCAATACAAAATGTATCCAATGCATGTGTTTGCCTACAGA       720
CysGlnTyrLysMetTyrProMetHisValPheAlaTyrArg
           230                           240
AACGGACAGTGGACACTGATTGGACGCCAGAACCCCCAGCTG       810
AsnGlyGlnTrpThrLeuIleGlyArgGlnAsnProGlnLeu
           260                           270
GATATACTGGCAGCCAGATGTGTGTTCACTGGTGAAGGGAGG       900
AspIleLeuAlaAlaArgCysValPheThrGlyGluGlyArg
           290                           300
CTGTACATCATGTATTACATGGAAGCCAAATATGCACTTTCC       990
LeuTyrIleMetTyrTyrMetGluAlaLysTyrAlaLeuSer
           320                           330
```

FIG. 6C

TTCATGACCTGTACAAAGAACGTGGCTCCAGATATGTTCAGAACTATC
PheMetThrCysThrLysAsnValAlaProAspMetPheArgThrIle
340
GTTATGATGCACGGGCATCACAAAGAAGCAGAAAACAAAGAAAAGAGT
ValMetMetHisGlyHisHisLysGluAlaGluAsnLysGluLysSer
A 370
GAGCAGGATTTCCATGTGGAAGAAGAACTGGACTGGCCTGGAGTGTAC
GluGlnAspPheHisValGluGluGluLeuAspTrpProGlyValTyr
Δ 400
AATAACCTRGTGATTTTCCACAGAGGTGACCATGTTTGGGATGGAAAC
AsnAsnLeuValIlePheHisArgGlyAspHisValTrpAspGlyAsn
430
CCAATTGAAGAAGACACCATCCTGGTCATTGACCCAAATAATGCTGAA
ProIleGluGluAspThrIleLeuValIleAspProAsnAsnAlaGlu
460
GGCTTGAGCATAGATACAGATGGAAATTATTGGGTCACAGATGTGGCT
GlyLeuSerIleAspThrAspGlyAsnTyrTrpValThrAspValAla
490
CCTCTCTTAATTCTGGGAAGGAGCATGCAACCTGGGAGTGACCAAAAT
ProLeuLeuIleLeuGlyArgSerMetGlnProGlySerAspGlnAsn
520
GGAGCTGTCTTCGTGTCAGACGGTTACTGTAACAGTCGGATTGTGCAG
GlyAlaValPheValSerAspGlyTyrCysAsnSerArgIleValGln
550
TCCTCTGGAAGCAGTCCTAGGCCAGGCCAGTTCAGTGTTCCTCACAGT
SerSerGlySerSerProArgProGlyGlnPheSerValProHisSer
580
AGGGAAAATGGCCGAATCCAATGCTTCAAAACTGACACCAAAGAATTT
ArgGluAsnGlyArgIleGlnCysPheLysThrAspThrLysGluPhe
610
GCCATTTCATATATACCAGGTTTCCTCTTTGCCGTAAACGGGAAGCCT
AlaIleSerTyrIleProGlyPheLeuPheAlaValAsnGlyLysPro
640

FIG. 6D

```
CCAGCAGAGGCCAATATCCCAATTCCTGTCAAACCGGACATG     1080
ProAlaGluAlaAsnIleProIleProValLysProAspMet
          350                            360
GCTTTAATGCAGCAGCCAAAACAGGGAGAGGAAGAAGTATTA     1170
AlaLeuMetGlnGlnProLysGlnGlyGluGluGluValLeu
          380                            390
TTGTTACCAGGCCAGGTTTCTGGGGTGGCCCTGGATTCTAAG     1260
LeuLeuProGlyGlnValSerGlyValAlaLeuAspSerLys
          410                            420
TCTTTTGACAGCAAGTTTGTTTACCAGCAAAGAGGTCTTGGG     1350
SerPheAspSerLysPheValTyrGlnGlnArgGlyLeuGly
          440                            450
ATCCTCCAGTCCAGTGGCAAGAACCTGTTTTATTTACCACAC     1440
IleLeuGlnSerSerGlyLysAsnLeuPheTyrLeuProHis
          470                            480
CTCCACCAGGTGTTCAAATTGGACCCGCATAGCAAAGAAGGC     1530
LeuHisGlnValPheLysLeuAspProHisSerLysGluGly
          500                            510
CATTTCTGCCAGCCCACCGATGTGGCTGTGGAGCCCAGTACT     1620
HisPheCysGlnProThrAspValAlaValGluProSerThr
          530                            540
TTTTCACCAAGCGGAAAGTTCGTCACCCAGTGGGGAGAAGAG     1710
PheSerProSerGlyLysPheValThrGlnTrpGlyGluGlu
          560                            570
TTGGCCCTTGTGCCTCATTTGGACCAGTTGTGTGTGGCAGAC     1800
LeuAlaLeuValProHisLeuAspGlnLeuCysValAlaAsp
          590                            600
GTGAGAGAGATTAAGCACGCATCATTTGGAAGGAATGTCTTT     1890
ValArgGluIleLysHisAlaSerPheGlyArgAsnValPhe
          620                            630
TACTTTGGAGACCAAGAGCCCGTGCAAGGATTTGTGATGAAC     1980
TyrPheGlyAspGlnGluProValGlnGlyPheValMetAsn
          650                            660
```

FIG. 6E

TTTTCCAGTGGGGAAATTATAGACGTCTTCAAGCCAGTACGCAAGCACT
PheSerSerGlyGluIleIleAspValPheLysProValArgLysHisP
670
GTGTACATTGGAGACGCACACACAAACACCGTGTGGAAGTTCACCCTGA
ValTyrIleGlyAspAlaHisThrAsnThrValTrpLysPheThrLeuT
700
GAAGTCCAGGAAATCAAAGAAGCCGAGGCAGTTGTTGAACCCAAAGTGG
GluValGlnGluIleLysGluAlaGluAlaValValGluProLysValG
730
AAACAGAAACTGAGCACAGAGCCCGGCTCGGGAGTGTCCGTGGTTCTCA
LysGlnLysLeuSerThrGluProGlySerGlyValSerValValLeuI
760
ATTGTCATGTTTATTCGGTGGAAAAAATCAAGGGCCTTTGGAGGAAAGG
IleValMetPheIleArgTrpLysLysSerArgAlaPheGlyGlyLysG
790
AAAGGCTACAGCAGAAAAGGGTTTGACCGAGTGAGCACAGAGGGGAGTG
LysGlyTyrSerArgLysGlyPheAspArgValSerThrGluGlySerA
820
GAGTACTCGGCCCCGCTGCCCAAGCCTGCACCTTCCTCCTGAGCTCCAG
GluTyrSerAlaProLeuProLysProAlaProSerSer
850
AGACTCCTTCCCCTTTAGCGCGTGTAAAGTTCTGTGCATTTGATTGTAA
TCATTTGGCTCCGTTGGCTTCTGTTTTCTAGGTGAGGAGTTCCCCACCA
AGAAGCCGCCCTCCTCTTCCAAGGTAGCGCTCCAACCCCCGAGGGAAGT
AAATAGCCCTATTCTCTGCTTGAACACAGTATTCTCCCAGTCCACACCC
CTCAGCCTGTGGCAGTGAAGAGAACCAACCTGCCACACGACGAAAAGCT
TTGCAATGAGAGAAATTTTAAAAAGTCTCTATTTAAATTCTTTTTTAA
AGATGGTTACACTGTTAGAACACTATTTTTCAGAATCTGAATGTAATTT

FIG. 6F

```
TCGACATGCCTCATGATATTGTGGCTTCTGAAGATGGGACT     2070
heAspMetProHisAspIleValAlaSerGluAspGlyThr
        680                           690
CTGAAAAAATGGAGCATCGGTCAGTTAAAAAGGCTGGCATT     2160
hrGluLysMetGluHisArgSerValLysLysAlaGlyIle
        710                           720
AGAACAAACCCACCTCCTCAGAATTGCAGAAGATGCAAGAG     2250
luAsnLysProThrSerSerGluLeuGlnLysMetGlnGlu
        740                           750
TTACAACCCTTCTGGTTATTCCTGTGCTGGTCCTGCTGGCC     2340
leThrThrLeuLeuValIleProValLeuValLeuLeuAla
        770                           780
GAAGCGGCGGCTTAAATCTGGGAAATTTCTTTGCAAGTCGA     2430
lySerGlyGlyLeuAsnLeuGlyAsnPhePheAlaSerArg
        800                           810
ACCAAGAGAAAGATGAGGACGACGGAAGTGAGTCTGAAGAG     2520
spGlnGluLysAspGluAspAspGlySerGluSerGluGlu
        830                           840
CCTTCGCCCGGGTAGCTGGACTGAGGTTTACCAGGATGCCC     2610


ACTGTACTCGTCAGTGTGGGACTGTACACACCTTATTTACT     2700
GTTCACTCCAGTGCCATTGTCTTTATATGAACTTAGCGTAG     2790
TTAGCTCATTCACATTTGGAGACGTTTTAGTTGGTGGATGT     2880
ATCGCCAGTGTCTTTCTTTGGTGCCTTTCCTGTTCAGCATT     2970
GCTAAATCTCCTTCTATTTTTTTAAAATCACTAACATTATA     3060
ATTTCTCCTCAGTTGGTGTGTTTCCGGGATGTCTTATTTTT     3150
GTGTAATAAAGTGTTTTCAGAGCATT                    3225
```

FIG. 6G

[Region A] (315bp)

GTGATTTCTATTCACTGCTTTCCAAGCTGCTAGGAGAAAGGGAAGATGTTCAT
GlyAspPheTyrSerLeuLeuSerLysLeuLeuGlyGluArgGluAspValHis

GGGTCAGACCTGGTAGCTGAGATTGCAAACGTGGTCCAGAAAAAGGACCTTGGT
GlySerAspLeuValAlaGluIleAlaAsnValValGlnLysLysAspLeuGly

TGGGGTAATGCTATCCTAGTCAGAGACAGGATCCACAGATTCCACCAGCTAGAG
TrpGlyAsnAlaIleLeuValArgAspArgIleHisArgPheHisGlnLeuGlu

TTCCAGCAGCCTGGCGAAGGCCCTTGGGAACCAGAACCCTCAGGAG
PheGlnGlnProGlyGluGlyProTrpGluProGluProSerGly

[Region C] (54bp)

ATCATGACCGCAAGCTCGAGTCAAGTTCTGGAAGAGTCCTGGGAAGATTCCGAC
AspHisAspArgLysLeuGluSerSerSerGlyArgValLeuGlyArgPheArg

FIG. 6H

GTGCACAAGTATAATCCTACAGAAAAGACAGAATCT
ValHisLysTyrAsnProThrGluLysThrGluSer

CGGTCTGACGCCAGAGAAGGTGCAGAGCATGAGGAA
ArgSerAspAlaArgGluGlyAlaGluHisGluGlu

TCAACTCTGAGGCCAGCTGAGAGCAGAGCTTTCTCG
SerThrLeuArgProAlaGluSerArgAlaPheSer

FIG. 13A

```
         10        20        30
CGGCGTGGACATGGCTGGCCTTCGTAGCCTGCTAGTT
           M  A  G  L  R  S  L  L  V

         120       130       140
CTACCAGACCATTTTCCAATGAATGTCTTGGTACCAC
  T  R  P  F  S  N  E  C  L  G  T  T

         230       240       250
TCTGATACATACTTCTGCATGTCGATGCGTTTGCCAA
S  D  T  Y  F  C  M  S  M  R  L  P  M

         340       350       360
TGGTTGCAATATGCCCTCATCCACTGGAAGTTACTGG
 G  C  N  M  P  S  S  T  G  S  Y  W

         450       460       470
GACTCCCCAAAGGTGTTGGATTCAGAGTTGGAGGAGA
  L  P  K  G  V  G  F  R  V  G  G  E

         560       570       580
TGTTCTGGTGTGTCCTTACACCTCACACGCCTGCCAC
C  S  G  V  S  L  H  L  T  R  L  P  Q

         670       680       690
TTCTGACCTTTCATGCCATTATAAAAAGTACCCAATG
 S  D  L  S  C  H  Y  K  K  Y  P  M
```

FIG. 13B

```
40        50        60        70
CTCCTCCTTGTTTTTCAGAGCAGCTGTTTGGGTTTCAGAA
L  L  L  V  F  Q  S  S  C  L  G  F  R  S

150       160       170       180
CAGACCAGTCATTCCTATTGATTCATCAGATTTTGCATTG
 R  P  V  I  P  I  D  S  S  D  F  A  L

260       270       280       290
TGGATGAGGAAACCTTCGTGATTGACTTCAAACCTCGTGC
  D  E  E  T  F  V  I  D  F  K  P  R  A

370       380       390       400
TTTTGTGATGAAGGCGTCTGTACAGACAAAGCCAATATTC
F  C  D  E  G  V  C  T  D  K  A  N  I  L

480       490       500       510
GACTGGAAGTAAATACTTCGTACTACAAGTACACTATGGG
 T  G  S  K  Y  F  V  L  Q  V  H  Y  G

590       600       610       620
AGCCTTTAATTGCTGGCATGTACCTTATGATGGCTCTTGA
  P  L  I  A  G  M  Y  L  M  M  A  L  D

700       710       720       730
CATGTCTTTGCCTATAGAGTTCACACTCACCATTTAGGTA
H  V  F  A  Y  R  V  H  T  H  H  L  G  K
```

FIG. 13C

```
 80         90        100        110
GCCCACTTTCTGTCTTTAAGAGGTTTAAAGAAA
  P  L  S  V  F  K  R  F  K  E  T

190        200        210        220
GATATTCGCATGCCTGGAGTCACACCTAAACAG
D  I  R  M  P  G  V  T  P  K  Q

300        310        320        330
CAGCATGGATACTGTCCATCATATGTTACTTTT
 S  M  D  T  V  H  H  M  L  L  F

410        420        430        440
TCTATGCCTGGGCAAGAAATGCTCCCCCCACCA
  Y  A  W  A  R  N  A  P  P  T  R

520        530        540        550
GATATTAGTGCTTTTAGAGATAATCACAAGGAC
D  I  S  A  F  R  D  N  H  K  D

630        640        650        660
CACTGTTATACCAGCAGGAGAGAAAGTGGTGAA
 T  V  I  P  A  G  E  K  V  V  N

740        750        760        770
AGGTAGTAAGTGGCTACAGAGTAAGAAATGGAC
  V  V  S  G  Y  R  V  R  N  G  Q
```

FIG. 13D

```
         780           790           800
AGTGGACACTGATTGGACGTCAGAGCCCCCAGCTGC
  W   T   L   I   G   R   Q   S   P   Q   L   P

         890           900           910
ACTGGTGAAGGAAGGACAGAAGCCACGCACATTGGT
T   G   E   G   R   T   E   A   T   H   I   G

        1000          1010          1020
GACCTGTACCCAGAATGTAGCTCCAGAAATGTTCAG
 T   C   T   Q   N   V   A   P   E   M   F   R

        1110          1120          1130
AAACAGAGAACAAAGATAAGACTTCACTACAACAGC
  T   E   N   K   D   K   T   S   L   Q   Q   P

        1220          1230          1240
GATGTTGTTCATGTGCATAAATATAACCCTACAGAA
D   V   V   H   V   H   K   Y   N   P   T   E

        1330          1340          1350
TGCCAGAGAGAGTGCAGAGCATGAGGACAGGGGCAA
 A   R   E   S   A   E   H   E   D   R   G   N

        1440          1450          1460
TTATCTCAGTACCGCAGCCCCTACCTGGTGAAGGCA
  I   S   V   P   Q   P   L   P   G   E   G   T
```

FIG. 13E

```
 810           820           830
CACAGGCTTTCTACCCTGTGGAACACCCAG
  Q   A   F   Y   P   V   E   H   P   V

 920           930           940
GGCACATCTAGTGATGAAATGTGCAACTTA
G   T   S   S   D   E   M   C   N   L

1030          1040          1050
AACCATCCCCCCAGAGGCCAATATTCCAAT
 T   I   P   P   E   A   N   I   P   I

1140          1150          1160
CAAAACAAGAAGAAGAAGTGTTAGAACAGG
  K   Q   E   E   E   V   L   E   Q   G

1250          1260          1270
AAGGCAGAATCAGAGTCAGACCTGGTAGCT
K   A   E   S   E   S   D   L   V   A

1360          1370          1380
TGCTATTCTTGTCAGAGACAGAATTCACAA
 A   I   L   V   R   D   R   I   H   K

1470          1480          1490
CCTGGGAACCAGAACACACAGGAGATTTCC
  W   E   P   E   H   T   G   D   F   H
```

FIG. 13F

```
 840          850          860          870          880
TAGATGTCAGTTTTGGTGACATACTGGCAGCAAGATGTGTGTTC
  D  V  S  F  G  D  I  L  A  A  R  C  V  F

 950          960          970          980          990
TACATTATGTATTACATGGAAGCCAAGCACGCAGTTTCTTTCAT
Y  I  M  Y  Y  M  E  A  K  H  A  V  S  F  M

1060         1070         1080         1090         1100
TCCTGTGAAGTCCGACATGGTTATGATGCATGGACATCACAAAG
 P  V  K  S  D  M  V  M  M  H  G  H  H  K  E

1170         1180         1190         1200         1210
GTGATTTCTATTCACTGCTTTCCAAGCTGCTAGGAGAAAGGGAA
  D  F  Y  S  L  L  S  K  L  L  G  E  R  E

1280         1290         1300         1310         1320
GAGATTGCAAATGTAGTCCAAAAGAAGGATCTCGGTCGATCTGA
E  I  A  N  V  V  Q  K  K  D  L  G  R  S  D

1390         1400         1410         1420         1430
ATTCCACAGACTAGAATCTACTTTGAGGCCAACAGAGAGCAGAG
 F  H  R  L  E  S  T  L  R  P  T  E  S  R  V

1500         1510         1520         1530         1540
ATGTAGAAGAGGCACTGGATTGGCCTGGAGTATACTTGTTACCA
  V  E  E  A  L  D  W  P  G  V  Y  L  L  P
```

FIG. 13G

```
        1550          1560          1570
GGCCAGGTTTCTGGGGTAGCTCTGGACCTTCAGAAT
G  Q  V  S  G  V  A  L  D  L  Q  N

        1660          1670          1680
AAGAGGACTCGGGCCAATTGAAGAAGATACTATTCT
 R  G  L  G  P  I  E  E  D  T  I  L

        1770          1780          1790
GCATAGACAAAGATGGAAATTATTGGGTCACAGACG
  I  D  K  D  G  N  Y  W  V  T  D  V

        2000          2010          2020
ACTGGAAGGTTCATCACACAGTGGGGAGAAGAGTCT
  G  R  F  I  T  Q  W  G  E  E  S

        2110          2120          2130
ATGTGTGGCCGACCGGGAAAATGGTCGGATCCAGTG
 C  V  A  D  R  E  N  G  R  I  Q  C

        2220          2230          2240
CGTATATACCAGGTTTGCTCTTTGCCGTAAATGGGA
  Y  I  P  G  L  L  F  A  V  N  G  K

        2330          2340          2350
TTCAAGCCAGTGCGCAAGCACTTTGACATGCCTCAT
F  K  P  V  R  K  H  F  D  M  P  H
```

FIG. 13H

```
1580          1590          1600          1610
AACCTGGTGATTTTCCACAGAGGTGACCATGTCTGGGATG
N   L   V   I   F   H   R   G   D   H   V   W   D   G

1690          1700          1710          1720
TGTCATAGATCCAAATAATGCTGCAGTCCTCCAGTCCAGT
 V   I   D   P   N   N   A   A   V   L   Q   S   S

1800          1930          1940          1950
TGGCAGATCCAAACACTGGGACCATCTTTGTATCAGATGG
  A   D   P   N   T   G   T   I   F   V   S   D   G

2030          2040          2050          2060
TCTGAGAGCAATCCTAAACCAGGCCAGTTCAGGGTTCCTC
S   E   S   N   P   K   P   G   Q   F   R   V   P   H

2140          2150          2160          2170
TTTTAAAACTGACACCAAAGAATTTGTGCGAGAGATTAAG
 F   K   T   D   T   K   E   F   V   R   E   I   K

2250          2260          2270          2280
AGCCTTACTTTGGGGACCAAAAACCAGTACAAGGATTTGT
  P   Y   F   G   D   Q   K   P   V   Q   G   F   V

2360          2370          2380          2390
GACATTACTGCATCTGAAGACGGGACTGTGTATGTTGGAG
D   I   T   A   S   E   D   G   T   V   Y   V   G   D
```

FIG. 13I

```
1620          1630          1640          1650
GAAACTCTTTTGACAGCAAGTTTGTGTACCAGCA
   N   S   F   D   S   K   F   V   Y   Q   Q

1730          1740          1750          1760
GGAAAAAATCTGTTTTACTTGCCACATGGCTTGA
G   K   N   L   F   Y   L   P   H   G   L   S

1960          1970          1980          1990
TTACTGCAACAGTCGGATCGTGCAGTTTTCACCA
 Y   C   N   S   R   I   V   Q   F   S   P   T

2070          2080          2090          2100
ACAGCTTGGCCCTTGTGCCTCATTTGGGCCAATT
   S   L   A   L   V   P   H   L   G   Q   L

2180          2190          2200          2210
CATGCATCATTTGGAAGAAATGTATTTGCAATTT
H   A   S   F   G   R   N   V   F   A   I   S

2290          2300          2310          2320
GATGAACTTTTCCAGTGGGGAAATTATAGATGTC
 M   N   F   S   S   G   E   I   I   D   V

2400          2410          2420          2430
ATGCTCACACCAACACCGTGTGGAAGTTCACTTC
   A   H   T   N   T   V   W   K   F   T   S
```

FIG. 13J

```
       2440      2450      2460      2470      2480
GACTGAAACAGCCCAGGTCTGGTTCCCGGGTGTGGACCTACATCACTCGTCAGTG
 T  E  T  A  Q  V  W  F  P  G  V  D  L  H  H  S  S  V

       2550      2560      2570      2580      2590
ATCTCAGGGCCAATCTTCCTCAGCAAATGAAAAAAAAAAGAGTGGAGCATCGATC
  L  R  A  N  L  P  Q  Q  M  K  K  K  R  V  E  H  R  S

       2660      2670      2680      2690      2700
GAAACCAAAATGGAGAACAAACCCGCCTCCTCAGAATTGCAGAAGATGCAAGAGA
E  T  K  M  E  N  K  P  A  S  S  E  L  Q  K  M  Q  E  K

       2770      2780      2790      2800      2810
CCTTCTGGTTATTCCGGTGGTTGTCCTGCTGGCCATTGCCATATTTATTCGGTGG
 L  L  V  I  P  V  V  V  L  L  A  I  A  I  F  I  R  W

       2880      2890      2900      2910      2920
GAGTACTGGGAAGACTTAGAGGAAAAGGAAGTGGAGGCTTAAACCTCGGAAATTT
  V  L  G  R  L  R  G  K  G  S  G  G  L  N  L  G  N  F
```

FIG. 13K

```
2490      2500      2510      2520      2530      2540
GCCATGCTGTGGTGGCAGCTCACATACAAAAAGAGGAAGATTGACAACAGATGTT
A  M  L  W  W  Q  L  T  Y  K  K  R  K  I  D  N  R  C  Y

2600      2610      2620      2630 (C) 2640      2650
AGTTAAAAAGGCTGGCATTGAGGTCCAGGAAATCAAAG|AATCCGAGGCAGTTGTT
 V  K  K  A  G  I  E  V  Q  E  I  K  E| S  E  A  V  V

2710      2720      2730      2740      2750      2760
AACAGAAACTGATCAAAGAGCCAGGCTCGGGAGTGCCCGTTGTTCTCATTACAAC
  Q  K  L  I  K  E  P  G  S  G  V  P  V  V  L  I  T  T

2820      2830     | 2840      2850      2860      2870
AAAAAATCAAGGGCCTTTGG|AGAGTCTGAACACAAAGTCGAGGCAAGTTCAGGAA
K  K  S  R  A  F  G| E  S  E  H  K  V  E  A  S  S  G  R

2930      2940      2950      2960      2970      2980
CTTTGCGAGCCGTAAAGGCTACAGTCGGAAAGGGTTTGACCGGCTCAGCACCGAG
 F  A  S  R  K  G  Y  S  R  K  G  F  D  R  L  S  T  E
```

FIG. 13L

```
        2990      3000      3010
GGGAGTGACCAGGAGAAAGATGAGGATGACGGAAGT
G  S  D  Q  E  K  D  E  D  D  G  S

        3100      3110      3120
AGTTGATGAGATTTACCAAGAATGCCAGGTTCCTTT

        3210      3220      3230
TTTACTTCGTTTTGGTTTAGTTGGCTTCTGTTTCTG

        3320      3330      3340
TCTTCCATCACGTTACTAATTTAATGATGGAAGCTT

        3430      3440      3450
ATAGCACTTCCATTGCCAGTGTCTTTCTTTGGTGCC

        3540      3550      3560
TTCTTCTATTTTTTTAAAATCACTAACATTATATTG

        3650      3660      3670
GATGTCTTATTTTTAGATGGTTACACTGTTAGAACA
```

FIG. 13M

```
3020          3030          3040          3050
GAATCAGAAGAAGAATATTCAGCACCTCTGCCCGCACCTG
E   S   E   E   E   Y   S   A   P   L   P   A   P   V

3130          3140          3150          3160
CCCTTTAGCACGATTAGAGTTTTGTGTATTTAATTGTAAA

3240          3250          3260          3270
GTTGAGGAGTTTCCTAAAAGTTCATAACAGTGCCATTGTC

3350          3360          3370          3380
TGCTCATTTACATTTTGAGACTTTTCTGTAGGTGTAAATA

3460          3470          3480          3490
TTTCCTGTTCAGCATTCTCAGCCTGTGGCAGTAAAGAGAA

3570          3580          3590          3600
CAACAAGGGAAAGAAAAAAGTCTCTATTTAAATTCTTTTT

3680          3690          3700          3710
CTATTTTCAGAATCTGAATGTAATTTGTGTAATAAAGTGT
```

FIG. 13N

```
3060      3070      3080      3090
TACCTTCCTCCTCCTGAAAACTGGGCTTTGATTT
  P   S   S   S

3170      3180      3190      3200
CTGTACTAGTCTGTGTGGGACTGTACACATTTTA

3280      3290      3300      3310
TTTATCTGAACATAGAATAGAGAAACAGTCCTCT

3390      3400      3410      3420
GCCCCATTCTCTGCTTGGACACAGTCTTTTCCCA

3500      3510      3520      3530
ACTTTGTGCTACACGACGACGAAGCTGCTAAATC

3610      3620      3630      3640
TTTAAATTTTCTTCTTTAGTTGGTGTGTTTTTGG

3720      3730      3740      3750
TTTCAGAGCATTAGCTGTCAGAGTGTATTTTGCC
```

FIG. 130

```
      3760      3770      3780      3790      3800
AATTTTTGCATATGTCCAGGGTTTTGTATACTTTTGTAATAATTACATAAACCACA

      3870      3880      3890      3900      3910
TTAAAATCAAGAAGATATTTTGTTATGTAGCTGATACAAATTAAAAACCAGCCTAA

      3980      3990      4000      4010      4020
GCCTGTATATCAATCAGAAGGTAAATACTTGAATAAAAGGTGATCATAGCTGAGAG
```

FIG. 13P

```
3810       3820       3830       3840       3850       3860
GATTGAGTGAAACCTACTCAATGTCTTCAACCAAAAGAAATGTGTTGTATTGTA

3920       3930       3940       3950       3960       3970
GAGCTTACATACATGTGTAAAATCAGGCTCTCTGATGATTCAACGAGAGTGTTT

4030       4040
GAAAAAAAAAAAAAAAAAA
```

FIG. 14A

```
          10         20         30
ATGGCCGGACGCGCCCGCAGCGGTCTGCTACTGCTGC

         120        130        140
AGAAACTACCAGATCATTTTCCAATGAATGCCTTGGT

         230        240        250
AAGAGTCTGACACATACTTCTGCATGTCCATGCGTCT

         340        350        360
CTGTTTGGATGCAATATGCCCTCGTCCACTGGAAGTT

         450        460        470
CACCCGGCTCCCGAAAGGTGTTGGATTCAGAGTTGGA

         560        570        580
AAGACTGCTCTGGCGTGTCCGTACATCTCACACGTGT
```

FIG. 14B

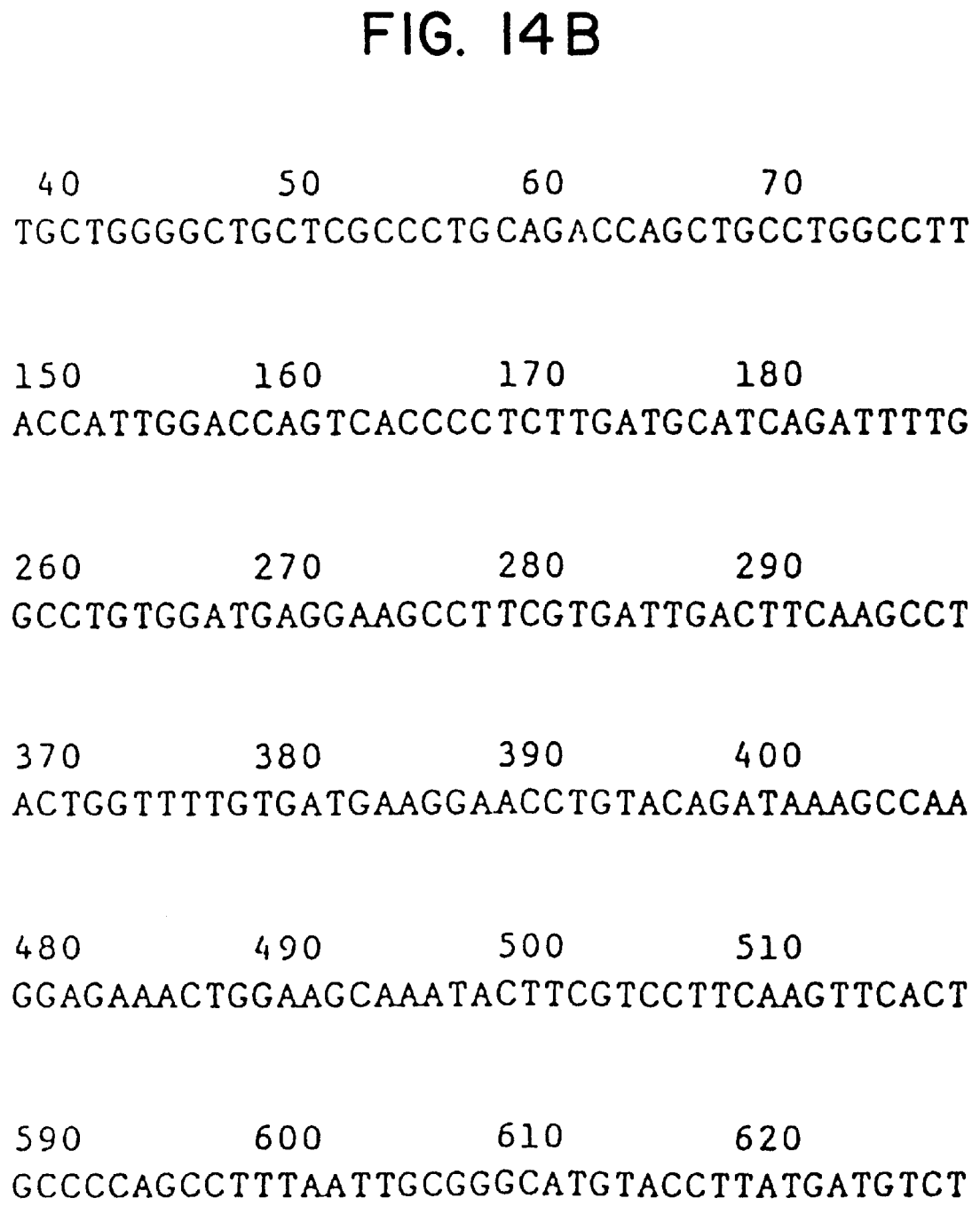

```
 40            50            60            70
TGCTGGGGCTGCTCGCCCTGCAGACCAGCTGCCTGGCCTT

150           160           170           180
ACCATTGGACCAGTCACCCCTCTTGATGCATCAGATTTTG

260           270           280           290
GCCTGTGGATGAGGAAGCCTTCGTGATTGACTTCAAGCCT

370           380           390           400
ACTGGTTTTGTGATGAAGGAACCTGTACAGATAAAGCCAA

480           490           500           510
GGAGAAACTGGAAGCAAATACTTCGTCCTTCAAGTTCACT

590           600           610           620
GCCCCAGCCTTTAATTGCGGGCATGTACCTTATGATGTCT
```

FIG. 14C

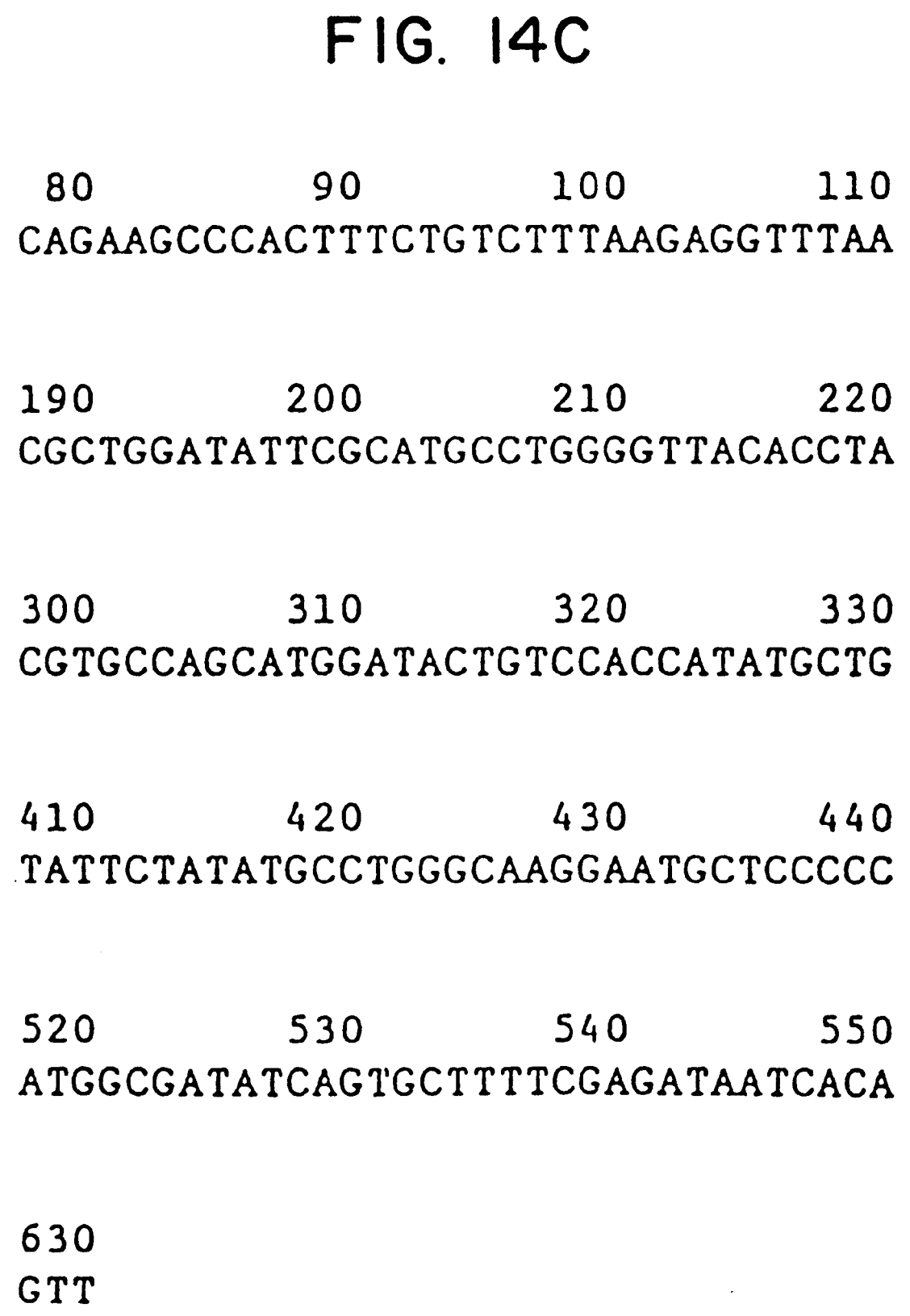

```
 80               90               100              110
CAGAAGCCCACTTTCTGTCTTTAAGAGGTTTAA

190              200              210              220
CGCTGGATATTCGCATGCCTGGGGTTACACCTA

300              310              320              330
CGTGCCAGCATGGATACTGTCCACCATATGCTG

410              420              430              440
TATTCTATATGCCTGGGCAAGGAATGCTCCCCC

520              530              540              550
ATGGCGATATCAGTGCTTTTCGAGATAATCACA

630
GTT
```

FIG. 15A

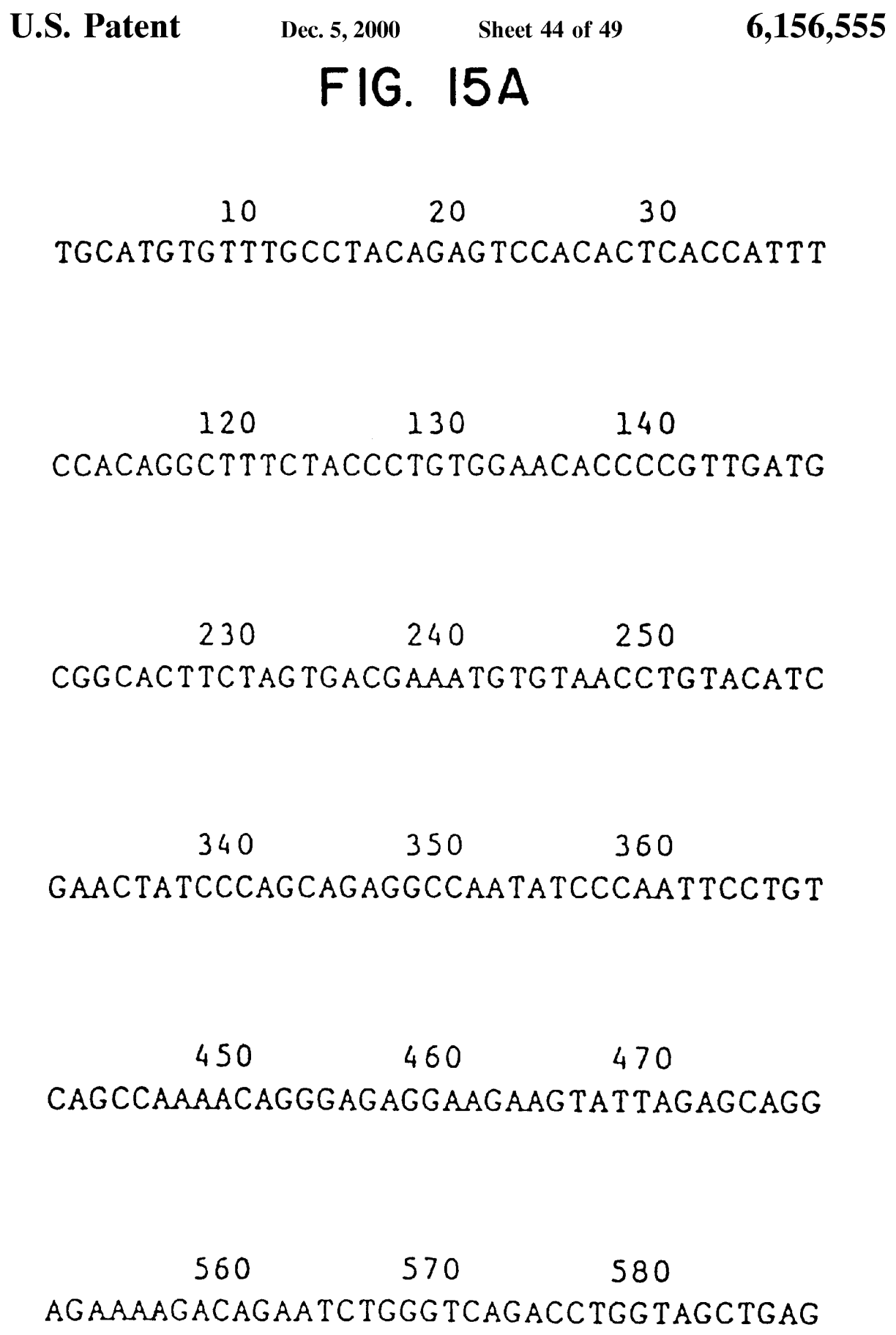

```
        10         20         30
TGCATGTGTTTGCCTACAGAGTCCACACTCACCATTT

       120        130        140
CCACAGGCTTTCTACCCTGTGGAACACCCCGTTGATG

       230        240        250
CGGCACTTCTAGTGACGAAATGTGTAACCTGTACATC

       340        350        360
GAACTATCCCAGCAGAGGCCAATATCCCAATTCCTGT

       450        460        470
CAGCCAAAACAGGGAGAGGAAGAAGTATTAGAGCAGG

       560        570        580
AGAAAAGACAGAATCTGGGTCAGACCTGGTAGCTGAG
```

FIG. 15B

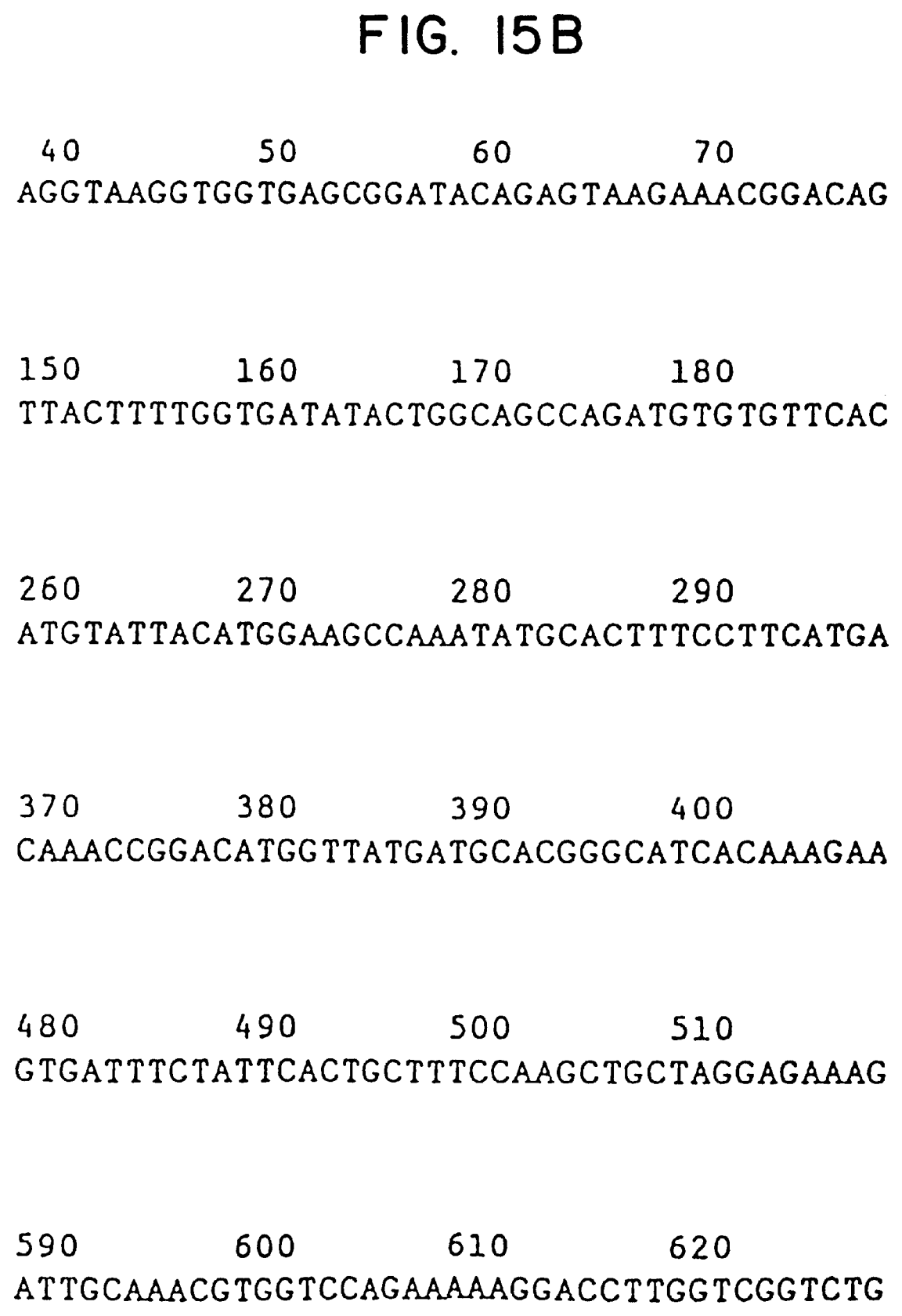

```
 40         50         60         70
AGGTAAGGTGGTGAGCGGATACAGAGTAAGAAACGGACAG

150        160        170        180
TTACTTTTGGTGATATACTGGCAGCCAGATGTGTGTTCAC

260        270        280        290
ATGTATTACATGGAAGCCAAATATGCACTTTCCTTCATGA

370        380        390        400
CAAACCGGACATGGTTATGATGCACGGGCATCACAAAGAA

480        490        500        510
GTGATTTCTATTCACTGCTTTCCAAGCTGCTAGGAGAAAG

590        600        610        620
ATTGCAAACGTGGTCCAGAAAAAGGACCTTGGTCGGTCTG
```

Figure 15C:
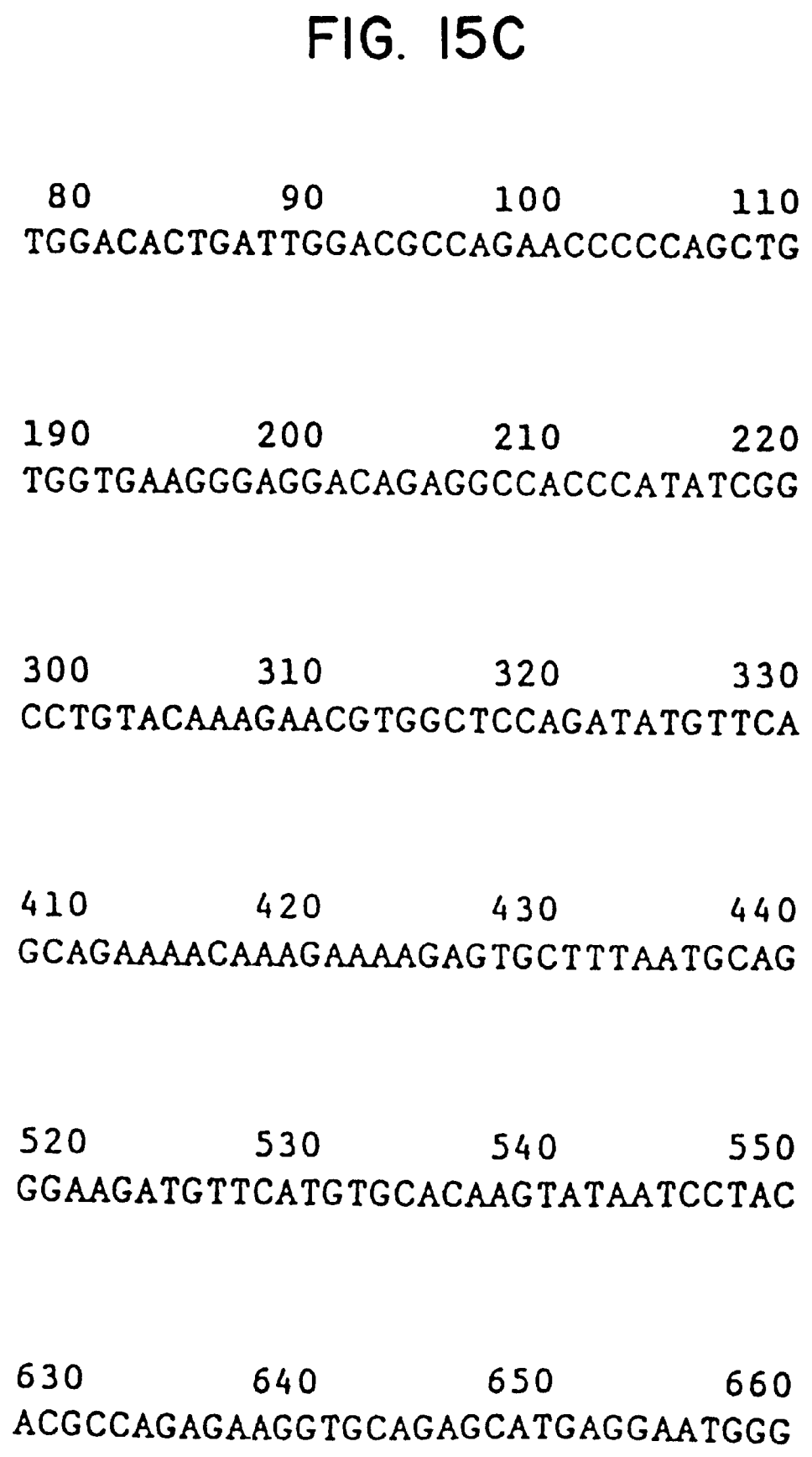

FIG. 15C 80 90 100 110
TGGACACTGATTGGACGCCAGAACCCCCAGCTG 190 200 210 220
TGGTGAAGGGAGGACAGAGGCCACCCATATCGG 300 310 320 330
CCTGTACAAAGAACGTGGCTCCAGATATGTTCA 410 420 430 440
GCAGAAAACAAAGAAAAGAGTGCTTTAATGCAG 520 530 540 550
GGAAGATGTTCATGTGCACAAGTATAATCCTAC 630 640 650 660
ACGCCAGAGAAGGTGCAGAGCATGAGGAATGGG

FIG. 15D

```
      670        680        690
GTAATGCTATCCTAGTCAGAGACAGGATCCACAGAT

      780        790        800
TGGGAACCAGAACCCTCAGGAGATTTCCATGTGGAA

      890        900        910
CCTAGTGATTTTCCACAGAGGTGACCATGTTTGGGA

     1000       1010       1020
TCATTGACCCAAATAATGCTGAAATCCTCCAGTCCA

     1110       1120       1130
GCTCTCCACCAGGTGTTCAAATTGGACCCGCATAGC
```

FIG. 15E

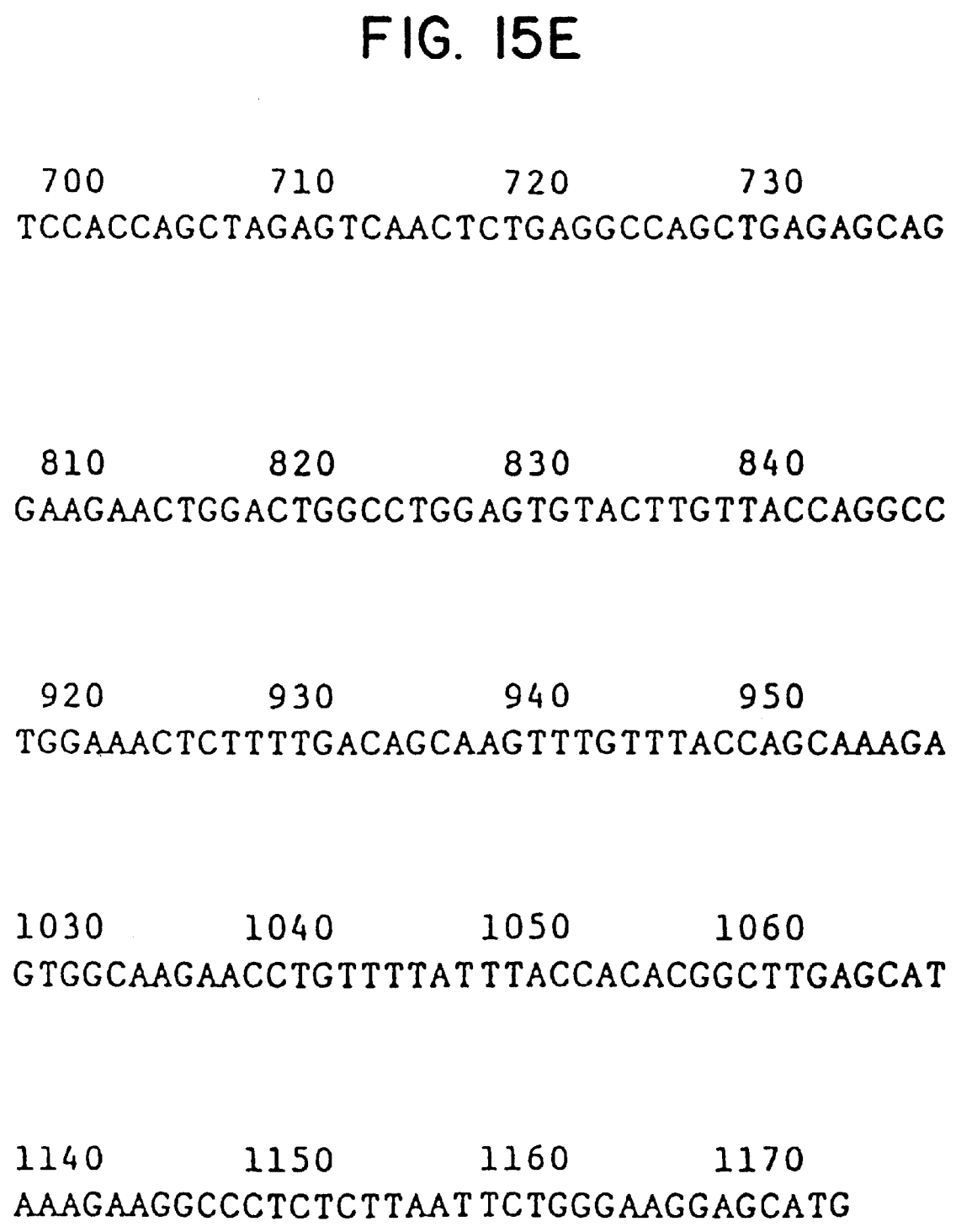

```
       700         710         720         730
     TCCACCAGCTAGAGTCAACTCTGAGGCCAGCTGAGAGCAG

       810         820         830         840
     GAAGAACTGGACTGGCCTGGAGTGTACTTGTTACCAGGCC

       920         930         940         950
     TGGAAACTCTTTTGACAGCAAGTTTGTTTACCAGCAAAGA

      1030        1040        1050        1060
     GTGGCAAGAACCTGTTTTATTTACCACACGGCTTGAGCAT

      1140        1150        1160        1170
     AAAGAAGGCCCTCTCTTAATTCTGGGAAGGAGCATG
```

FIG. 15F

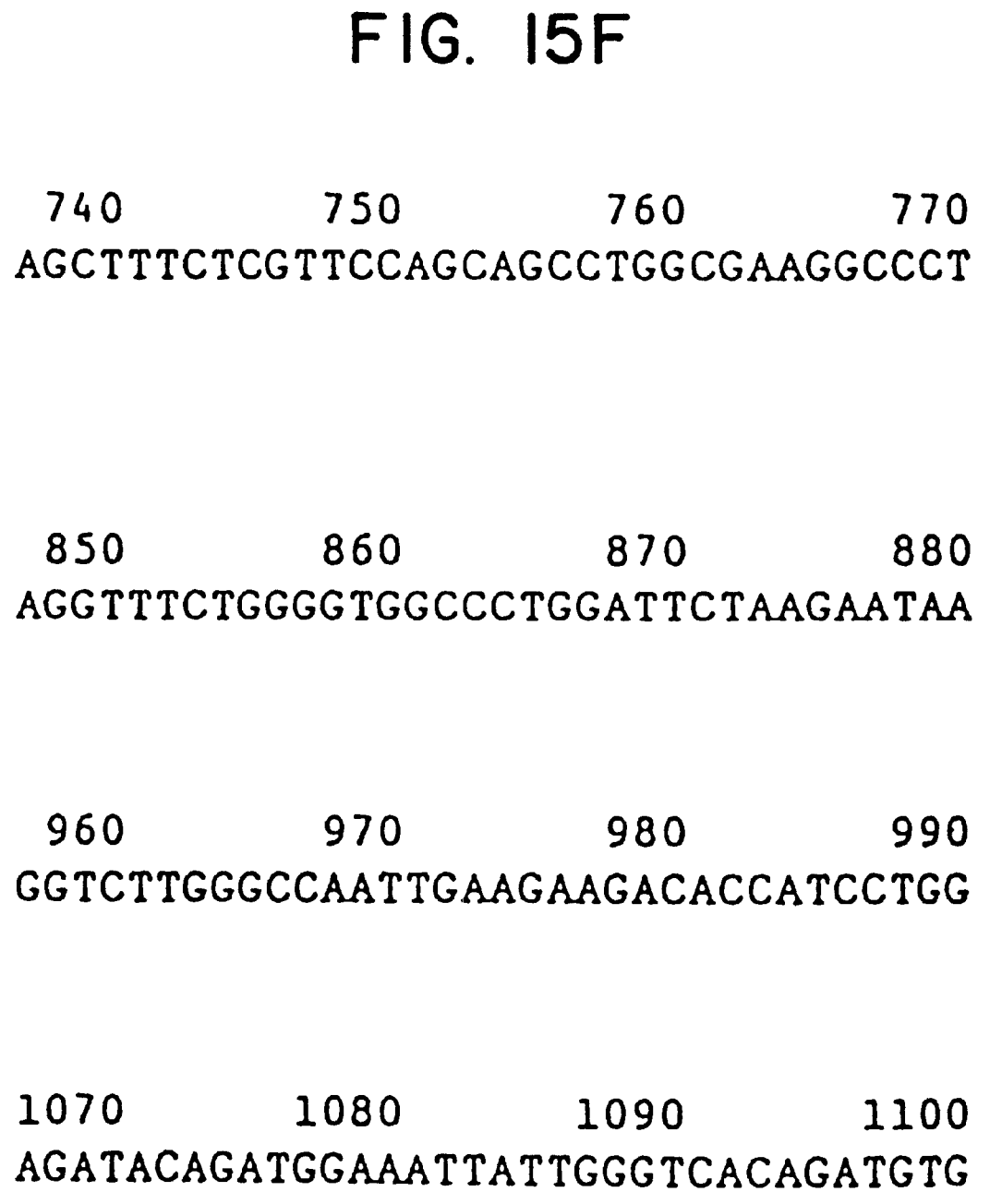

```
 740       750       760       770
AGCTTTCTCGTTCCAGCAGCCTGGCGAAGGCCCT

 850       860       870       880
AGGTTTCTGGGGTGGCCCTGGATTCTAAGAATAA

 960       970       980       990
GGTCTTGGGCCAATTGAAGAAGACACCATCCTGG

1070      1080      1090      1100
AGATACAGATGGAAATTATTGGGTCACAGATGTG
```

METHOD OF PREPARING AN ENZYME PARTICIPATING IN C-TERMINAL AMIDATION

This application is a division of application Ser. No. 08/070,301, filed May 24, 1991, now U.S. Pat. No. 5,871, 995, which is a 371 of Application No. PCT/JP90/01036, filed Aug. 14, 1990.

TECHNICAL FIELD

This invention relates to a novel enzyme participating in a C-terminal amidation of a peptide C-terminal glycine adduct, a method of preparing same, and the use thereof. The term "participating in a C-terminal amidation" as used herein means possessing an action promoting any step for converting a peptide C-terminal glycine adduct into its peptide C-terminal amidated compound.

BACKGROUND ART

In the past, the enzyme participating in the enzymatic reaction in vivo, i.e., a C-terminal amidation of a C-terminal glycine adduct of peptides (compound in which glycine is peptide-bonded to C-terminal residue) is called peptidylglycine-α-amidating monooxygenase (C-terminal amidating enzyme) (EC.1.14.17.3) (Bradbury et. al., Nature, 298, 686, 1982: Glembotski et. al., J. Biol. Chem., 259. 6385, 1984), and is considered to catalyze the following reaction:

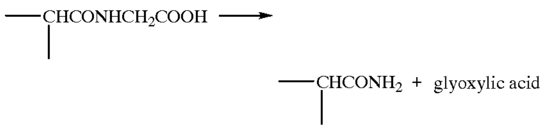

To clarify the amidation mechanism in vivo and utilize the enzyme for the method of converting the peptides which exhibit a physilogical activity for the first time by an amidation of the C-terminal with the peptide produced by the recombinant DNA technique, for example, calcitonin and gastrin, in vitro, attempts have been made to purify this enzyme. For example, there have been reported those derived from bovine pituitary gland middle lobe (Murthy et. al., J. Biol. Chem., 261, 1815, 1986), porcine pituitary gland (Kizer et. al., Endocrinology, 118, 2262, 1986; Bradbury et. al., Eur. J. Biochem., 169, 579, 1987), porcine heart atrium (Kojima et. al., J. Biochem., 105, 440, 1989), Xenopus body skin (Mizuno et. al., Biochem., Biophys. Res. Commun., 137, 984, 1986), rat thyroid gland tumor (Mehta et. al., Arch. Biochem., Biophys., 261, 44, 1988).

On the other hand, since it is difficult to procure a large amount of these purified enzymes, attempts have been made to isolate the cDNA's necessary for expression of these enzymes by use of the recombinant DNA technique generally practiced in recent years, and the production of the enzymes by utilizing same. For example, Eipper B. A, et. al. in Mol. Endocrinol. 1, 777–790, 1987, Ohsuye K. et. al. in Biochem. Biophys. Res. Commun., 150, 1275–1281, 1988, Stoffers, D. A. et. al. in Proc. Natl. Acad. Sci., USA, 86, 735–739, 1989, and Glauder, J. et. al. in Biochem. Biophys. Res. Commun., 169, 551–558, 1990, have reported peptide C-terminal amidating enzyme cDNA's derived from bovine pituitary gland, frog skin, rat atrium and human thyroid gland cell, respectively. Further, although not necessarily having a satisfactory productivity, there are also known examples of peptide C-terminal amidating enzymes produced by using of the recombinant DNA technique utilizing the cDNA derived from frog and bovine (e.g., see Japanese Unexamined Patent Publication (Kokai) No. 1-104168, Published International Application: WO89/02460, and Perkins et. al., Mol. Endocrinol., 4, 132–139, 1990).

On the other hand, these proteins have been reported to have molecular weights of 38, 42 or 54 kDa in bovine, 39 kDa in frog, and 41, 50, or 75 kDa in rat, which are very different from each other, depending on the collecting methods, etc. For example, the literature of Bradbury et. al., described above, Ramer et. al., 110, 8526–8532 (1988) and Young et. al., J. Am. Chem. Soc. 111, 1933–1934 (1989) suggest the existence of reaction intermediatesm, but there are no current examples which clarify the isolation of an intermediate, and the relationship between the intermediate and the amidating enzyme.

As described above, the peptide C-terminal amidating enzyme exhibits a very interesting action in vivo, and a composition having a constant purity derived from a specific living body organ is known. Nevertheless, these compositions cannot be used for the production of a peptide C-terminal amidated compound in vivo, as the purity and stability as well as to production costs thereof are not satisfactory. To solve these problems, on the premise that it is necessary to collect basic knowledge concerning the enzyme, i.e., clarify the reaction mechanism when carrying out the C-terminal amidation reaction, the present inventors attempted to isolate the intermediate product, and consequently successfully isolated the intermediate and determined the structure thereof. From this result it was found that the enzymatic active substance called the C-terminal amidating enzyme of the prior art is not a one-step reaction as considered in the prior art, but is a two-step reaction through the intermediate (corresponding to C-terminal α-hydroxylglycine adduct).

Since it is predicted that an efficient conversion of a peptide C-terminal glycine adduct into the corresponding amidated compound can be carried out by the single or combined use of enzymes catalyzing the respective reaction under adequate conditions, it will become necessary to provide these enzymes. Further, where the existence of these enzymes can be confirmed, it will become necessary to provide an efficient method of preparing same.

DISCLOSURE OF THE INVENTION

According to the present invention, there are provided an enzyme participating in a C-terminal amidation which acts on a C-terminal glycine adduct represented by the following formula (I):

(I)

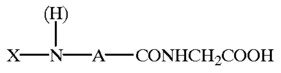

(wherein A represents a residue other than α-amino group or imino group and α-carboxylic group derived from naturally occurring α-amino acid, X represents a hydrogen atom or a residue of an amino acid derivative which is bonded to an N atom through a carbonyl group) to form a C-terminal α-hydroxylglycine adduct represented by the following formula (II):

(II)

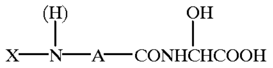

(wherein A and X have the same meanings as above, hereinafter sometimes called "Enzyme-I"), and an enzyme participating in a C-terminal amidation of a C-terminal glycine adduct which acts on a C-terminal α-hydroxylglycine adduct represented by the above formula (II) to form a C-terminal amidated compound represented by the following formula (III):

(III)

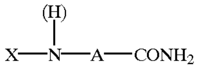

(wherein A and X have the same meanings as above) (hereinafter sometimes called "Enzyme-II").

In the formulae (I), (II), and the formula (III), the hydrogen atom in the bracket (H) means no hydrogen atom exists when A is derived from an α-amino acid having an α-imino group.

By using each of these enzymes or a combination thereof, the peptide C-terminal glycine adduct represented by the formula (I) can be efficiently converted into the corresponding peptide C-terminal amidated compound represented by the formula (III).

According to the present invention, there are also provided a method of producing these enzymes from the above-mentioned enzyme activity-containing compound, by the use of a specific ligand, and a method of efficiently producing these enzymes by the use of a cDNA coding these enzyme activity-containing peptides.

Further, according to present invention, there are provided a method of assaying the activity of the above-mentioned enzyme and a method of screening said enzyme-containing compounds.

Furthermore, according to the present invention, a cDNA encoding said enzyme activity derived from horse.

BRIEF DESCRIPTION OF THE DRAWINGS

In the description and drawings, letters which are used in an amino acid sequence by one letter mean those which are usually used in the art, and "hyG" means α-hydroxyglycine.

FIGS. 5(A)–5(F) show the amino acid sequences estimated from the peptide C-terminal amidating enzyme cDNA's cloned from human, horse, bovine, rat, frog, as a one letter representation;

FIGS. 6(A)–6(H) show the nucleotide sequence of the C-terminal amidating enzyme cDNA cloned from the rat pituitary mRNA and the amino acid sequence estimated therefrom;

B (Bam HI), N (Nsi I), RI (EcoRI), RV (EcoRV), S (SphI), X (XmaI).

Figure 8:
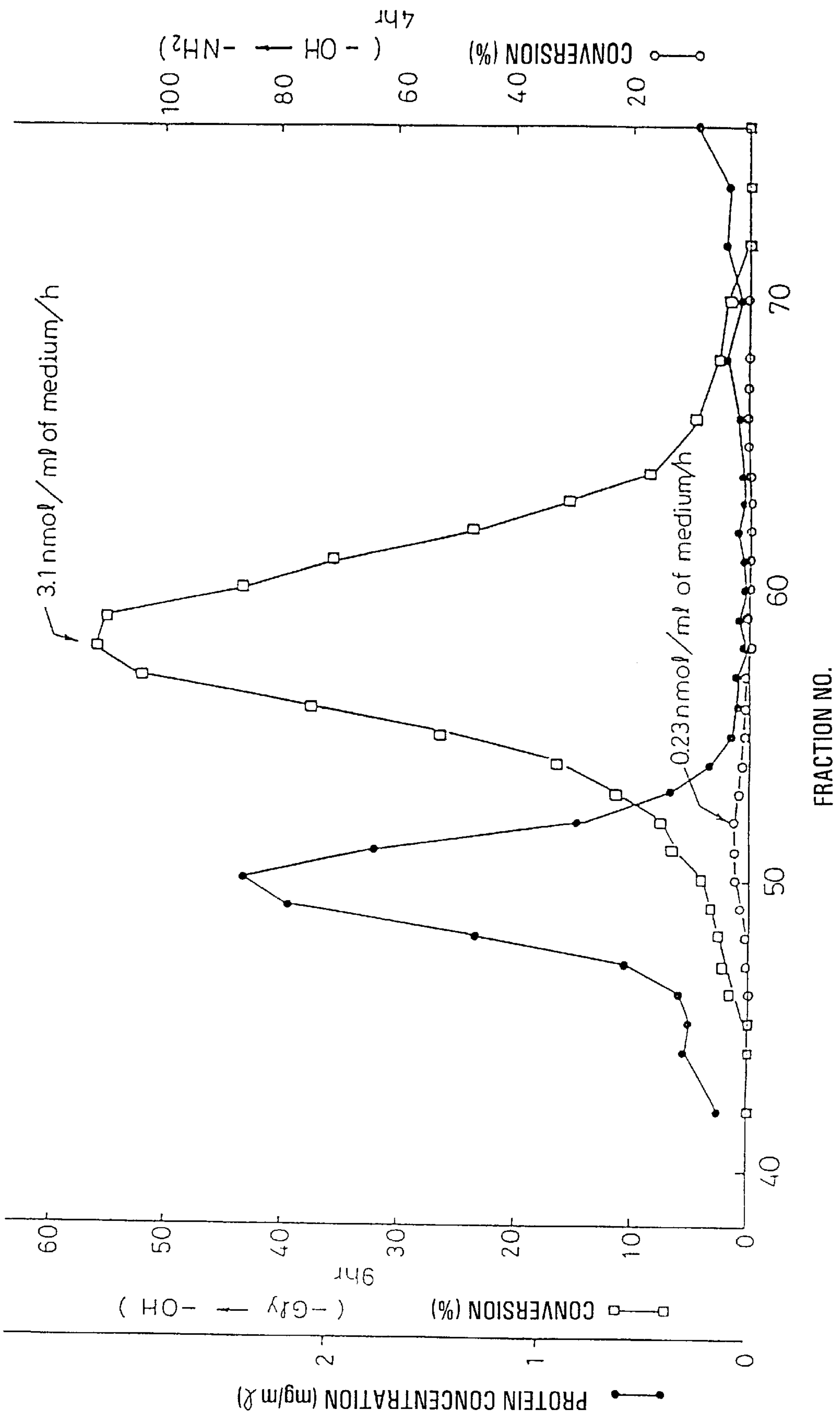
Figure 9:
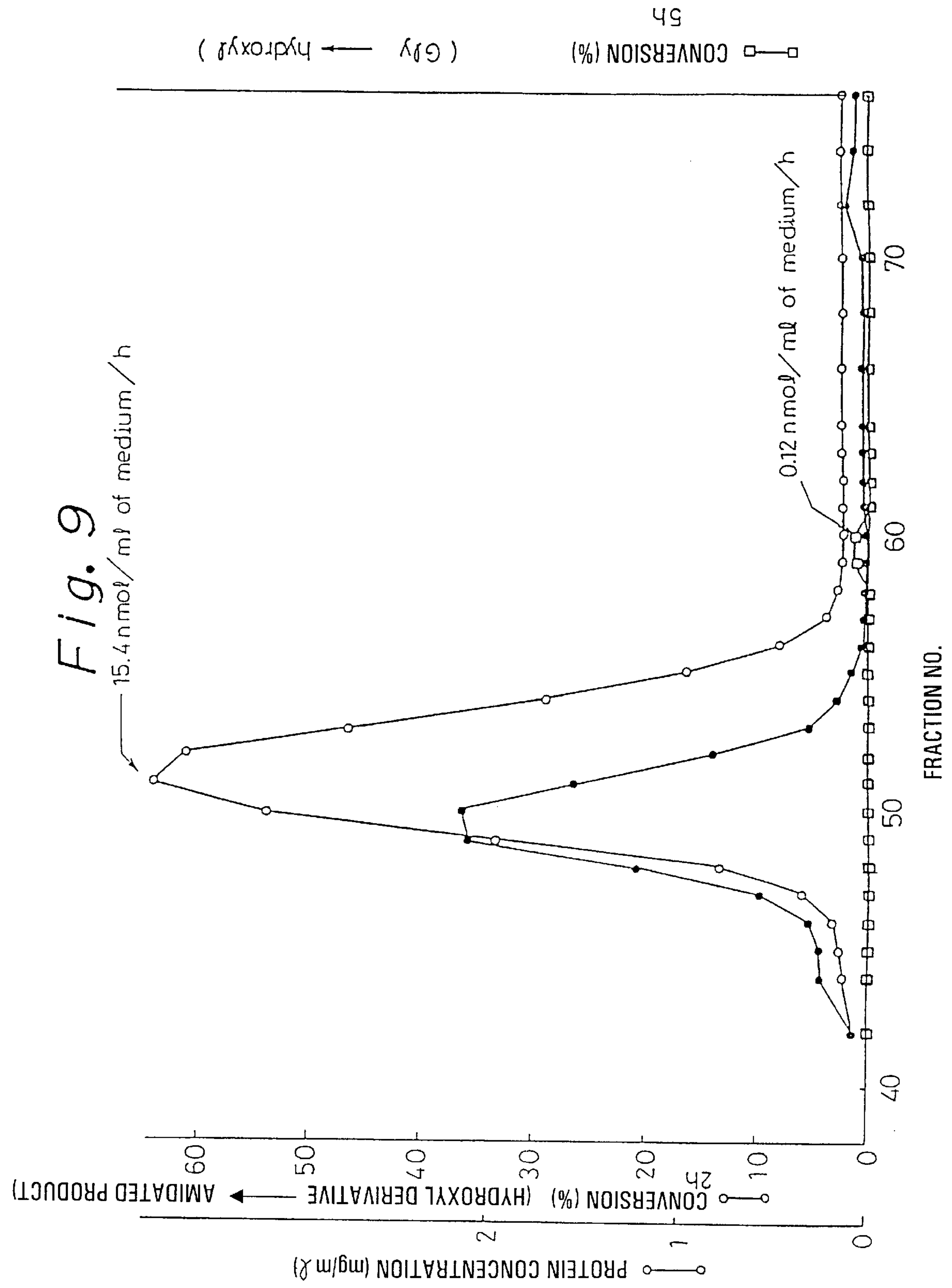
Figure 10:
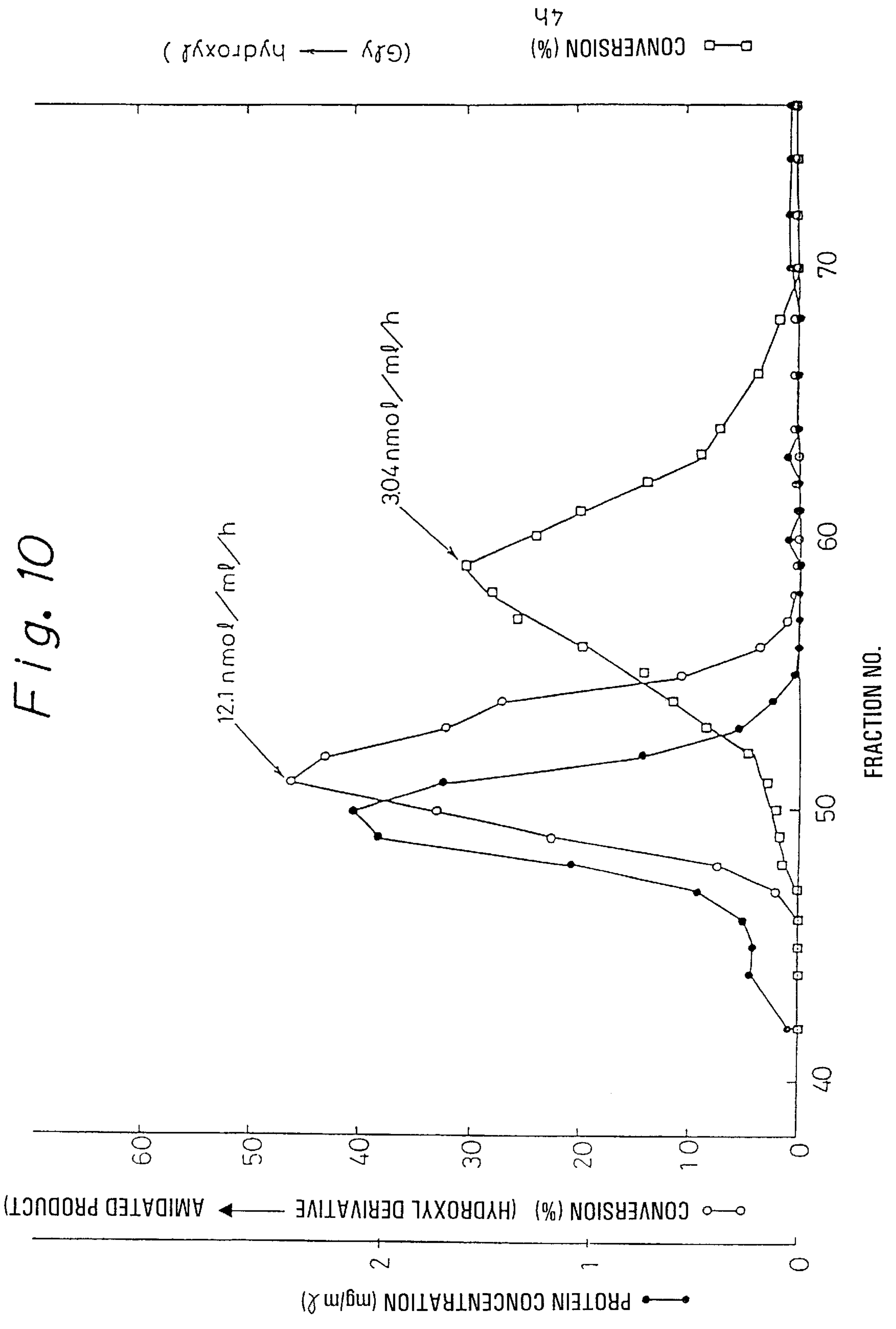
Figure 11:
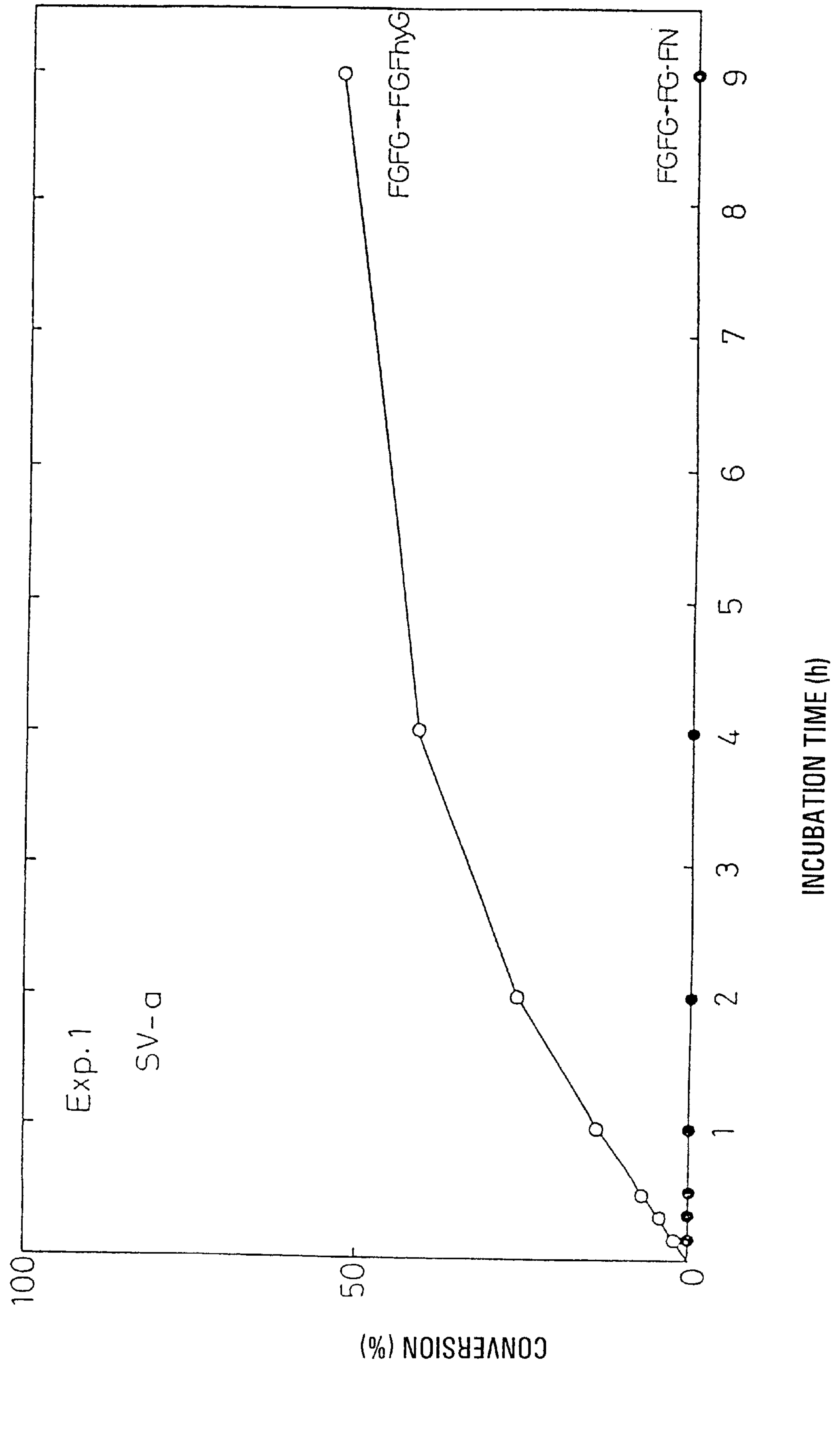
Figure 12:
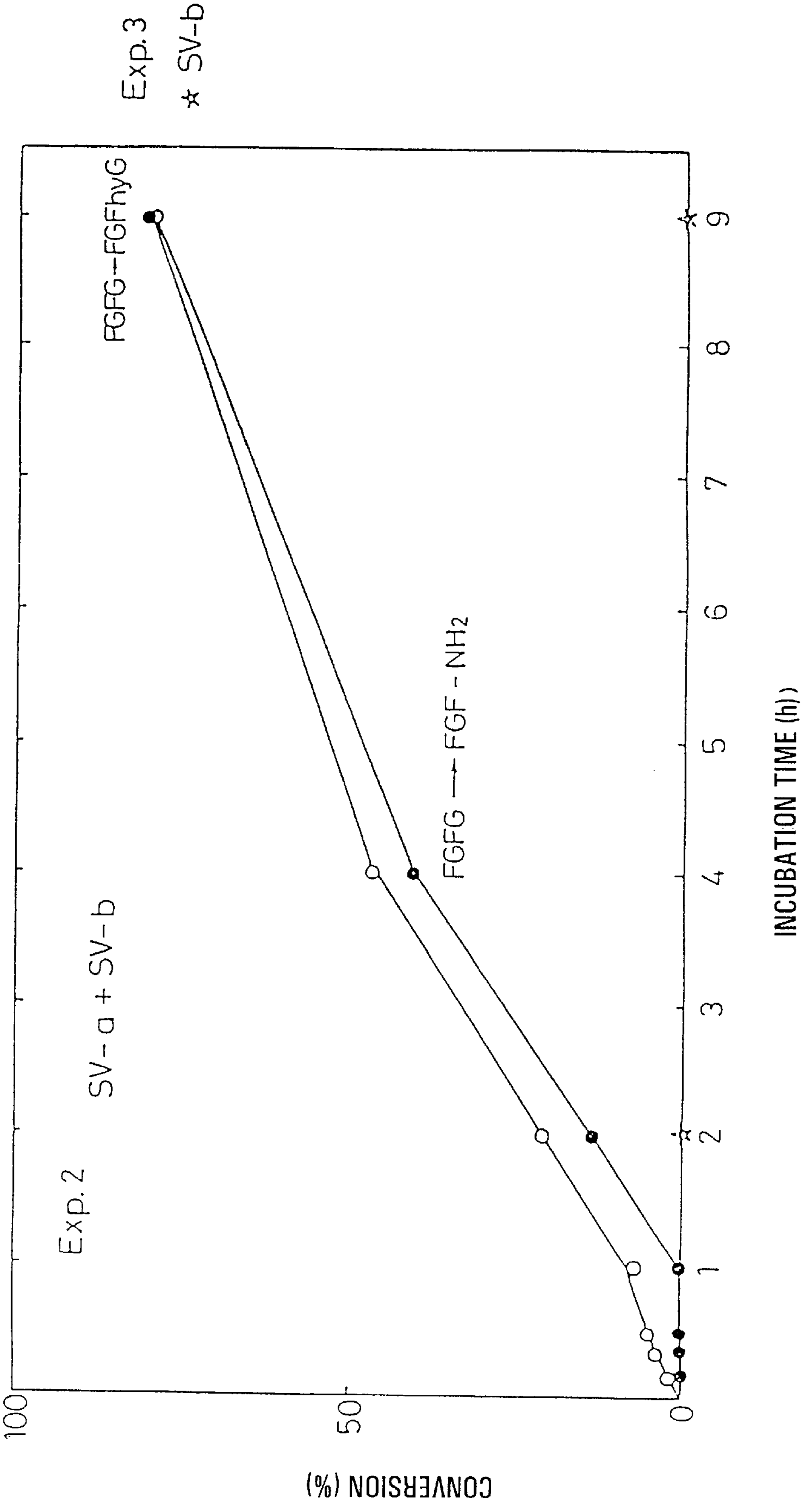

FIG. 8, FIG. 9, and FIG. 10 show the Sephacryl S-200 column chromatography patterns of the enzymes expressed by the plasmids SV-a, SV-b, SV-203, respectively;

FIG. 11 and FIG. 12 show the changes in production of the α-hydroxylglycine adduct, and the C-terminal amidated compound over a lapse of time when using PheGlyPheGly as the substrate;

FIGS. 13(A)–13(P) show the nucleotide sequence of the longest CDNA fragment among the cDNA's coding for the polypeptide having a peptide C-terminal amidating enzyme activity derived from isolated horse and the amino acid sequence coded for thereby as a one letter representation; and FIGS. 14(A)–14(C) and FIGS. 15(A)–15(F) respectively show a part of the base sequence of cDNA's coding for the peptide C-terminal amidating enzymes derived from rat used as the probe, which were digested with different restriction endonucleases, respectively.

BEST MODE OF CARRYING OUT THE INVENTION

The C-terminal glycine adduct represented by the formula (I) of the present invention, i.e., the substrate of the enzyme composition of the present invention, may generally include compounds derived from amino acid derivatives wherein the

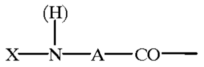

moiety in the above formula is natural or synthetic, particularly the compounds derived from peptides or proteins, with glycine being bonded to the C-terminal acid residue thereof [represented by —N(H)—A—CO—]. As the C-terminal amino acid residue, a residue derived from naturally occurring α-amino acid, particularly an amino acid constituting proteins, for example, an aliphatic amino acid such as glycine or alanine; branched amino acid such as valine, leucine or isoleucine; hydroxylated amino acid such as serine or threonine; acidic amino acid such as aspartic acid or glutamic acid; amide such as asparagine or glutamine; basic amino acid such as lysine, hydroxylysine, arginine; sulfur containing amino acid such as cysteine, cystine or methionine; aromatic amino acid such as phenylalanine or tyrosine; heterocyclic amino acid such as tryptophan or histidine; and imino acid such as proline or 4-hydroxyproline may be included. The hydrogen atom or the residue of the amino acid derivative bonded to the α-amino group or imino group of the amino acid residue

[represented by X-] is not particularly limited with respect to the kind and chain length of the peptide of the constituent amino acid residue, provided that it is a peptide bonded through a single amino acid or α-amino group, and further, phosphoric acid, sugar or other substituent may be covalently bonded to the constituent amino acid residue and it may form a conjugate with a lipid. Specific examples of the above-mentioned substituents include, corresponding to the respective amino acid residues, the substituents on the guanidino group of arginine residue, for example, alkyl groups such as methyl, ethyl, etc., the residues derived from adenosine diphosphate ribose, citrulline or ornithine; substituents derived from ε-amino group of lysine residue, for example, the substituents derived from compounds having glycosyl group, pyridoxyl group, biotinyl group, lipoyl group, acetyl group, phosphoric acid or δ-hydroxyl group, compounds having δ-glycosyl group, residue derived from glutaraldehyde or citraconic anhydride, etc.; substituents on the imidazole group of hystidine residue, for example, methyl group, the substituents derived from phosphoric acid, iodine atom or flavin; substituents on proline residue, for example, hydroxyl group, dihydroxyl group, glycosyloxy group; substituents on the benzene ring of phenylalanine residue, for example, hydroxyl group or glycosyloxy group; substituents on the hydroxyl group of tyrosine residue, for example, glycosyloxy group, sulfonic acid group, iodine atom, bromine atom or chlorine atom, or a compound having hydroxyl group, bisether, adenine, residue derived from uridine or RNA (ribonucleic acid), etc.; substituents on the hydroxyl group of serine residue, for example, methyl group, glycosyl group, phosphopanteteic acid, adenosine diphosphoric acid ribosyl or phosphoric acid; substituents on the hydroxyl group of threonine residue, for example, glycosyl group, methyl group or phosphoric acid group; substituents on the SH group of cysteine residue, for example, glycosyl group, the substituents derived from cystinyl, dehydroalanyl group, selenium atom, or residue derived from heme or flavin; substituents on the carboxyl group of aspartic acid or glutamic acid residue, for example, methyl group, phosphoric acid group or γ-carboxyl group; substituents on asparagine or glutamine residue, for example, glycosyl group, pyrrolidonyl group or imino group, etc.

The peptide having glycine peptide bonded to the C-terminal residue as in the above substrate, or its derivative may be either naturally extracted or produced by chemical synthesis, or produced by a recombinant DNA technique. Therefore, as the substrate of the present invention, the compound represented by the formula (I) may include C-terminal glycine adducts (i.e., amide bonded compounds of C-terminal carboxyl group and glycine), for example, peptides with amino acid residues of about 2 to 100, phosphate peptides as represented by casein, protein kinase, adenovirus EIA protein, RAS 1 protein, etc. and hydrolyzates thereof, lipoproteins such as thromboplastin, $\alpha_1$-lipoprotein, lipovitellin, etc. and hydrolyzates thereof, metal proteins as represented by hemoglobin, myoglobin, hemocyanin, chlorophyil, phycocyanin, flavin, rhodopsin, etc., and hydrolyzates thereof, glycoproteins as represented by collagen, laminin, interferon α, seroglycoide, avidin, etc., and hydrolyzates thereof, as well as other physiologically active peptides of the maturation type with amidated C-terminal carboxyl group, for example, calcitonin, secretin, gastrin, vasoactive intestinal peptide (VIP), cholecystokinin, caerulein, pancreatic polypeptide, growth hormone-releasing factor, corticotropin-releasing factor, calcitonin gene related peptide, etc. Of these, a preferable substrate for identifying the enzyme activity of the enzyme composition of the present invention includs D-tyrosyl-valyl-glycine, D-tyrosyl-tryptophanyl-glycine, glycyl-phenylalanyl-glycine, phenylalanyl-glycyl-phenylalanyl-glycine, D-tyrosyl-leucyl-asparaginyl-glycine, arginyl-phenylalanyl-arginyl-alanyl-arginyl-leusyl-glycine, leucyl-methionyl-glycine, glycyl-leucyl-methionyl-glycine, phenylalanyl-glycyl-leucy]-methionyl-glycine, asparaginyl-arginyl-phenylalanyl-glycine, tryptophanyl-asparaginyl-arginyl-phenylalanyl-glycine, alanyl-phenylalanyl-glycine, glysyl-alanyl-phenylalanyl-glycine, seryl-lysyl-alanyl-phenylalanyl-glycine, arginyl-tyrosyl-glycine, glycyl-methionyl-glycine, glycyl-tyrosyl-glycine, glycyl-histidyl-glycine, histidyl-glycyl-glycine, tryptophanyl-glycyl-glycine and glycyl-cysteinyl-glycine and the like (except for glycine, L-form is shown unless otherwise particularly noted as D-). On the other hand, a preferable substrate for effectively utilizing the present enzyme composition includs the peptides with glycine peptide bonded to the C-terminal carboxyl group thereof, which form a physiologically active peptide of the maturation type by amidation of the above-mentioned C-terminal carboxyl group.

Acting on the substrate as mentioned above, the enzyme-I of the present invention can form a C-terminal α-hydroxylglycine adduct represented by the following formula (II):

(II)

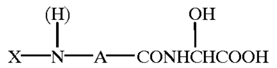

[wherein specific examples of the

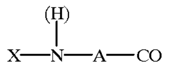

moiety have the meanings as defined for the above formula (I)].

The compound represented by the formula (II) can be converted by hydrolyzing under conditions whereby no deleterious influence is exerted on the moiety

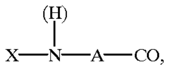

or by treating with the second enzyme of the present invention, as described below, to be converted to the corresponding C-terminal amidated compound.

The above-mentioned enzyme-I has a molecular weight of about 25 kilo-dalton (kDa) in horse and of about 36 kDa in rat according to the molecular weight determination method by use of gel filtration. More specifically, the molecular weight can be measured according to the gel filtration method known per se [e.g., "Seikagaku Jikken Kouza 5, Enzyme Study Method, Former vol., p. 283–298", Tokyo Kogaku Dojin (1975)]. Specifically by use of a 50 mM Tris-HCl (pH 7.4) containing 100 mM potassium chloride as the equilibration and eluting solution, gel filtration was effected on Toyopearl HW-55S (produced by Toso), and the molecular weight was determined with β-amylase (M.W. 200,000), alcohol dehydrogenase (M.W. 150,000), BSA (M.W. 66,000), carbonic anhydrolase (M.W. 29,000) and cytochrome C (M.W. 15,400) as the indices.

The enzyme-I of the present invention is further specified by the following physicochemical properties, namely:

(a) the optimum pH is about 5 to 7 and the stable pH is 4 to 9;

(b) the acting optimum temperature is from about 25 to 40° C;

(c) metal ions and ascorbic acid act as the cofactor.

The above properties (a) and (b) are measured by the use of conventional buffers, specifically, Tris-HCl, Mes-potassium hydroxide, Tes-sodium hydroxide, Hepes-potassium hydroxide buffers. The enzyme composition of the present invention can catalyze the above reaction within the temperature range of 1° C. to 55° C., but will be inactivated at 56° C. within about 10 minutes; a slight inactivation is also seen at around 40° C.

As the metal ion, $Cu^{2+}$, $Zn^{2+}$, $Ni^{2+}$, $Co^{2+}$, $Fe^{3+}$ etc. are suitable, but particularly preferably $Cu^{2+}$ and $Zn^{2+}$ are used.

The present invention further provides another kind of enzyme, as follows. More specifically, there is provided an enzyme participating in a C-terminal amidation of a C-terminal glycine adduct which acts on a C-terminal α-hydroxylglycine adduct represented by the above formula (II) to form a C-terminal amidated compound represented by the following formula (III):

(III)

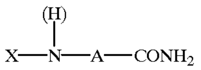

(wherein A and X have the same meanings as defined above) and glyoxylic acid.

The molecular weight of this enzyme also depends on the origin thereof. When separated from the enzyme activity-containing compound described below, followed by purification, the enzyme-II is an enzyme participating in a C-terminal amidation of glycine adduct, which has a molecular weight of about 40 kDa when derived from horse, or about 43 kDa when derived from rat according to the molecular weight determination method by gel filtration. The molecular weight of the enzyme-II produced by utilizing cDNA is sometimes large and similar to the case of the enzyme-I. The significance and molecular weight determination of the moiety

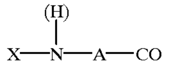

used for specifying this enzyme are the same as used for specifying the enzyme-I. As preferable substrates for identification of the enzyme activity of the enzyme-II, α-hydroxyglycine compounds corresponding to the substrates specifically enumerated above for the enzyme-I may be included.

Specific examples include D-tyrosyl-valyl-α-hydroxyglycine, D-tyrosyl-tryptophanyl-α-hydroxyglycine, glycyl-phenylalanyl-α-hydroxyglycine, phenylalanyl-glycyl-phenylalanyl-α-hydroxyglycine, D-tyrosyl-leucyl-asparaginyl-α-hydroxyglycine, arginyl-phenylalanyl-α-hydroxyglycine, arginyl-alanyl-arginyl-leusyl-α-hydroxyglycine, leucyl-methionyl-α-hydroxyglycine, glycyl-leucyl-methionyl-α-hydroxyglycine, phenylalanyl-glycyl-leucyl-methionyl-α-hydroxylglycine, asparaginyl-arginyl-phenylalanyl-α-hydroxyglycine, tryptophanyl-asparaginyl-arginyl-phenylalanyl-α-hydroxyglycine, alanyl-phenylalanyl-α-hydroxyglycine, Lysyl-alanyl-phenylalanyl-α-hydroxyglycine, seryl-lysyl-alanyl-phenylalanyl-α-hydroxyglycine, arginyl-tyrosyl-α-hydroxyglycine, glycyl-methionyl-α-hydroxyglycine, glycyl-tyrosyl-α-hydroxyglycine, glycyl-histidyl-α-hydroxyglycine, histidyl-glycyl-α-hydroxyglycine, triptophanyl-glycyl-α-hydroxyglycine, and glycyl-cysteinyl-α-hydroxyglycine and the like.

The enzyme-II is also specified by having substantially the same properties as the enzyme-I, as other physicochemical properties, namely:

(a) the optimum pH is about 5 to 6 and the stable pH is 4 to 9; and (b) the acting optimum temperature is from about 15 to 35° C.

The above properties (a) and (b) are measured by the use of conventional buffers, specifically, Tris-HCl, Mes-potassium hydroxide, Tes-sodium hydroxide, Hepes-potassium hydroxide buffers. The enzyme composition of the present invention can catalyze the above reaction within the temperature range of 1° C. to 55° C., but will be inactivated at 56° C. within about 10 minutes, a slight inactivation is also seen at around 40° C.

Preparation of enzyme

The enzyme-I and the enzyme-II of the present invention as described above can be prepared according to the separation purification method of enzyme known per se, but preferably are obtained according to the preparation method of the present invention disclosed in the present specification. More specifically, it is possible to utilize the preparation method of the enzyme-I or the enzyme-II characterized by treating the enzyme activity containing compound of the enzyme-I or the enzyme-II with the substrate affinity chromatography by use of the C-terminal glycine adduct represented by the above formula (I) as the ligand and the anion exchange chromatography.

The enzyme activity-containing compound to be used in this method can include all of those containing the enzyme of the present invention, and may be either those derived from an organism or those provided artificially. Generally speaking, as the organism having these enzyme activities, there may be included preparations derived from mammals such as human, bovine, horse, porcine, sheep, rabbit, goat, rat, mouse, etc.; avian such as chicken, jungle fowl, rock-dove, etc.; reptiles such as stone-turtle, viper, rattling snake and cobra; tatrachian such as newt, xenopus, bullfrog, toad, etc.; fish such as lamprey, hagfish, oil shark, electric ray, sturgeon, herring, salmon, eel, Tetrodon rubripes, bream; insects such as coakroach, silkworm, drosophila and bee. As the suitable material to be extracted, there may be included homogenates derived from such organs as the brain, pituitary gland, stomach, heart and liver, as well as biological fluids containing body fluids such as blood and lymph.

More specifically, the enzyme of the present invention (enzyme-I or enzyme-II) can be obtained from the biological fluid having the present enzyme as mentioned above, by substrate affinity chromatography using the C-terminal glycine adduct represented by the following formula (I):

(I)

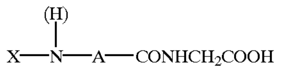

(wherein A and X have the meanings as defined above) as the ligand, used optionally in combination with the conventional method, such as:

(1) fractionation by precipitation;

(2) heparin affinity chromatography;

(3) molecular weight fractionation method by dialysis, gel filtration, etc.; and/or (4) ion-exchange chromatography.

As the above-mentioned ligand, all of the peptide C-terminal glycine adducts represented by the above formula (I) can be used, but preferably they include the peptides comprising 2 to 6 amino acid residues including glycine as specifically a preferable substrate for identification of the above-mentioned enzyme activity. Among them, D-Tyr-Trp-Gly, Phe-Gly-Phe-Gly and Gly-Phe-Gly are more preferable, but that using Phe-Gly-Phe-Gly as the ligand is particularly preferred as having a strong affinity for the enzyme composition of the present invention (also called the present enzyme).

These ligands are generally used as bound to a water-insoluble carrier, and it is important that the carboxyl group of the C-terminal glycine residue of the peptide to be used as the ligand should be in a free state or bondable to the carrier through the amino group of the amino acid residue at the N-terminal. In other words, the carrier may be any one which can be bound to the amino group of the peptide, and an active group reactive with the amino group may be chemically introduced into the carrier, or alternatively a commercially available carrier having the active group already introduced wherein may be used. The method of introducing chemically may be any method generally employed. For example, as described in "Seikagaku Jikkenhou, Vol. 5, Former vol., p. 257–281" written by Kasai, Tokyo Kagaku Dojin (1975), imidocarboxyl group is introduced into agarose by the use of cyanogen bromide. Commercially available activated carriers may include agarose type, cellulose type, hydrophilic polyvinyl type, etc. with the substrate as the index, but any of these may be employed. As the agarose type carrier, there may be included CNBr activated Sepharose 4B (produced by Pharmacia) in which the CNBr method is used for binding the ligand with the amino group, CH-Sepharose 4B, ECH-Sepharose 4B (all produced by Pharmacia) by the carbodiimide method, Affigel 10, Affigel 15 (all are produced by Biorad), the tresyl activated Sepharose 4B (produced by Pharmacia) by use of the tresyl chloride method, etc. As the cellulose type carrier, Formylcellulofine (produced by Chisso) by using the formyl method may be included. As the hydrophilic polyvinyl type carrier, there may be included AF-carboxyltoyopearl 650 by using the carbodiimide method, AF-formyltoyopearl 650 by use of the formyl method, AF-tresyltoyopearl 650 by use of the tresyl chloride method, AF-epoxytoyopearl 650 by use of the epoxy activation method (all are produced by Toso), etc. The binding reaction with the ligand may be carried out according to the instructions for each carrier.

Of these, the method of preparing Affigel 10 is described. The reaction between Affigel 10 and the peptide is carried out in a buffer such as Mopspotassium hydroxide, etc. of 0.001 to 1 M, preferably 0.1 M. The reaction conditions can be 0 to 20° C., 10 minutes to 24 hours and about pH 3 to 11, but preferably are 4° C., 4 to 24 hours and pH 5 to 9. The mixing ratio of Affigel 10 to the peptide to be used for binding may be within the range of up to 25 μmol per 1 ml of Affigel, because more will be bound as the peptide is added in a larger amount within this range, but conveniently about 1 to 20 μmol may be used with respect to the binding efficiency. After the reaction, the mixture is thoroughly washed with the buffer used during the reaction, and then Tris-HCl (pH 8.0) is added to the final concentration of 50 mM, and the unreacted active groups are blocked according to the shaking method, at 4° C. for one hour, etc., whereby the substrate affinity gel is prepared.

The substrate affinity chromatography may be carried out either batchwise or continuously with the gel packed in a column. The time for contacting the sample with the gel may be such that the present enzyme can be sufficiently adsorbed, but may be generally 20 minutes to 24 hours. Nonadsorbed components are washed away with a buffer having the same composition as that used for equilibration of the gel with a low ionic strength and pH of 6.0 to 11.0, preferably 7.0 to 9.0, for example, 10 mM Hepes-potassium hydroxide (pH 7.0). Among them, the fractions in which the present enzyme activity exists are eluted. The eluting solution may have any composition which can give the present enzyme with a good efficiency, but preferable examples include buffers with a pH of between 7.0 to 9.0 containing about 1 to 40% of acetonitrile together with 0.1 to 1 M sodium chloride, such as 10 mM Hepes-sodium hydroxide (pH 7.0) containing 20% acetonitrile and 0.4 M sodium chloride. Also, when filled in the column, elution may be carried out with application of the concentration gradient.

In some cases, before or after practicing the above substrate affinity chromatography [hereinafter represented by (5)], or both before and after, the fractionation by way of precipitation as mentioned above [hereinafter represented by (1)], heparin affinity chromatography [hereinafter represented by (2)] dialysis, molecular weight fractionation by gel filtration, etc. [hereinafter represented by (3)] and/or ion-exchange chromatography [hereinafter represented by (4)] may be also practiced. Thus, the present enzymes (enzyme-I and enzyme-II) can be separated form other intervening matters, and for separation of the enzyme-I and enzyme-II, it is effective to practice the steps of (3) and/or (4). Generally speaking, it is preferable to practice the total number of 1 to 6 steps, and further, the above step (5) or (3) as the final step. Specific examples of the combinations of the respective steps may include only (5), (1)→(5), (5)→(3), (2)→(5), (1)→(3)→(5), (2)→(3)→(5), (1)→(5)→(3), (2)→(5)→(3), (2)→(1)→(5), (1)→(2)→(3)→(5), (1)→(2)→(5)→(3), (1)→(3)→(5)→(3), (1)→(2)→(1)→(5), (1)→(2)→(1)→(3)→(5), (2)→(1)→(5)→(3), (2)→(1)→(3)→(5), (2)→(1)→(3)→(5)→(3), (1)→(2)→(3)→(5)→(3), (1)→(3)→(2)→(3)→(5), (1)→(3)→(2)→(3)→(5)→(3), (4)→(3)→(5), (5)→(3)→(5)→(3), (1)→(5)→(3)→(5)→(3), (4)→(5), (1)→(3)→(5)→(4)→(3), (1)→(3)→(4)→(3)→(5), (1)→(2)→(3)→(5)→(3)→(4), (1)→(2)→(3)→(5)→(4)→(3), or (4)→(5)→(3). Among them, it is preferred that the steps should proceed in the order of (1)→(2)→(3)→(5), (1)→(2)→(3)→(5)→(3), (1)→(3)→(2)→(3)→(5) or (1)→(3)→(2)→(3)→(5)→(3), (1)→(2)→(3)→(5)→(4)→(3).

In the following, the above steps (1) to (4) are described. These steps are all carried out at 0° C. to 10° C., preferably 4° C.

As the substance to be used for fractionation according to precipitation of (1), there may be included salts such as ammonium sulfate, etc., organic solvents such as ethanol, acetone, etc., polymers such as polyethylene glycol, etc. The concentration added is not particularly limited, but it is preferable to use the conditions under which the present enzyme can be recovered with a good efficiency, and can be separated from other protein components. For example, when 30 to 50% of saturated ammonium sulfate, 10 to 15% (w/v) of polyethylene glycol 6000 are added, the present enzyme comes into the precipitated fraction, while many proteins exist in the supernatant portion, whereby purification can be effected with a good efficiency. Addition may be preferably done gradually while stirring with a stirrer. After the mixture is left to stand for at least one hour after completion of the addition, the fractions in which the present enzyme exists are recovered by centrifugation. When the precipitated fraction is recovered, this is dissolved in an appropriate buffer. The buffer, provided that it has pH 6.0 to 11.0, preferably 7.0 to 9.0, may have any composition, for example, Tris-HCl, Hepes-potassium hydroxide, Tes-sodium hydroxide, etc. The concentration is not particularly limited within the range which can maintain the buffering ability, but is preferably about 5 to 50 mM.

The active fraction obtained according to (1) may be subjected again to (1) or proceed to any step of (2) to (5), but when proceeding to (2), (4) or (5) by using a salt such as ammonium sulfate for fractionation of (1), it is necessary to lower the salt concentration to a level at which the present enzyme can be bound to the gel used in the step of (3) or in the subsequent step with addition of an appropriate buffer. On the other hand, when the precipitates are dissolved and left to stand for one hour or longer, or when dialysis is performed, insoluble substances may be formed, which are removed by centrifugation or filtration.

As for heparin affinity chromatography of (2), it may be carried out either batchwise or continuously by filling the gel in a column. Commercially available gels having heparin as the ligand may include heparin Sepharose CL-6B (produced by Pharmacia), Affigel heparin (produced by Biorad), heparin agarose (produced by Sigma), AF-heparintoyopearl 650 (produced by Toso).

The biological extract is contacted directly, or after the treatment of the fraction by precipitation as shown in (1), with the heparin affinity gel. The contact time may be such that the present enzyme can be sufficiently adsorbed, but generally 20 minutes to 12 hours. The components having no affinity for heparin are removed with a buffer having a low ionic strength to the extent that no present enzyme is eluted with pH of 6.0 to 11.0, preferably 7.0 to 9.0, for example, 10 mM Hepes-potassium hydroxide (pH 7.0). Thereafter, the fractions containing the present enzyme are eluted. As the eluting solution, one having a higher recovery of the present enzyme activity is preferred. For example, one having a pH of 6.0 to 11.0 containing a salt generally used for enzyme purification such as 0.5 M–2 M sodium chloride, potassium chloride, ammonium sulfate, etc. Elution may be performed according to the salt concentration gradient when packed in column, but one-step elution may be also practiced. For example, elution may be effected with 10 mM hepes-potassium hydroxide buffer (pH 7.0) containing 0.3 to 2.0 M sodium chloride.

The active fraction obtained in the step (2) may be also provided for any of the steps (1) to (4), or when performing again the step (2), proceeding to the step (4) or (5), the step (3) may be previously conducted, or the ionic strength lowered to a level at which the present gel can be adsorbed to the gel used in (2), (4) or (5) by addition of a large amount of a buffer of 50 mM or lower having a low ionic strength and pH 6.0 to 11.0, preferably 7.0 to 9.0, for example 5 mM Hepes-potassium hydroxide (pH 7.0).

As for the step of removing low molecular weight substances by dialysis, gel filtration, etc. of (3), in the case of dialysis, the membrane to be used may have a cut-off molecular weight to the extent that the present enzyme cannot pass therethrough, but is preferably 1,000 to 10,000. The method of dialysis may be one generally employed as described in, for example, "Seikagaku Jikken Kouza, Vol. 5, Former Vol., p. 252–253" written by Soda, Tokyo Kagaku Dojin (1975), and may be carried out for several hours to several days, against a buffer with low ionic strength having pH 6.0 to 11.0, preferably pH 7.0 to 9.0, such as 10 mM Hepes-potassium hydroxide (pH 7.0), 10 mM Tris-HCel (pH 7.5), etc. Also, during dialysis, when insoluble substances are precipitated, they are removed by, for example, centrifugation, filtration, etc.

Concerning gel filtration, any carrier generally used for gel filtration may be employed. It is preferable that, for example, Sephadex G-10, G-15, G-25, G-50, G-75, G-100, Sephacryl S-200, S-300 (all produced by Pharmacia), Toyopearl HW-40, HW-55 (produced by Toso), Biogel P-2, P-4, P-6, P-10, P-30, P-60, P-100 (all produced by Biorad), etc. The buffer to be used may have the same composition as that used during dialysis. If the ionic strength is too low, however, it may be considered that adsorption of the present enzyme onto the gel well occur, and therefore, the concentration is made 5 to 200 mM, preferably 10 to 20 mM. The method of gel filtration may be practiced as described in, for example, "Seikagaku Jikken Kouza, Vol. 5, Former vol., p. 283–298", written by Soda, Tokyo Kagaku Dojin (1975). After a sample is added in an amount sufficient to obtain separation capacity relative to the bed volume of the gel filtration carrier, elution is effected and the fraction in which the present enzyme activity exists is recovered.

The active fraction obtained by the step of (3) can be permitted to proceed to the respective steps of (1) to (5) without any particular treatment.

For the ion-exchange chromatography, any carriers commercially available for ion-exchange chromatography in general may be used. For example, Aminex, Dowex, Amberlite, SP-Sephacryl M, Asahipak, DEAE-Toyopearl, DEAE-Sephadex, CM-Sepharose, DEAE Bio-Gel A, CM-Cellulose, DEAE-Cellulofine, Partisil SCY, Mono Q and Mono S, etc. are preferred. The buffer to be used and the use method may follow the method as described in the heparin affinity gel item. The basic operational methods may follow those described in general in "Shinkiso Seikagaku Jikkenho 2, Extraction-Purification-Analysis I" (Maruzen, 1988), etc.

The active fractions obtained in the step of (4) may be subjected to any of the steps (1) to (5), but when carrying out again (4) or proceeding to (2) to (5), it (3) must be previously conducted, or a large amount of a buffer of pH 5.0 to 11.0, preferably 6.0 to 8.0, with low ionic strength of 50 mM or lower, for example, Hepes-sodium hydroxide (pH 7.0), etc. must be added to lower the ionic strength to a level at which the present enzyme can be adsorbed onto the gel used in (2), (4) or (5). By passing through the purification steps as mentioned above, the crude product of the enzyme of the present invention can be obtained. Such a crude enzyme of product can be further isolated as fractions having peaks at a molecular weight of about 25,000 and at a molecular weight of 40,000, respectively, by protein separation means using the gel filtration step (3) to give a preparation of the present enzyme.

The respective steps as described above may be practiced by monitoring the activity of the enzyme-I and/or the enzyme-II by use of the compound of the formula (I) or the formula (II) as the substrate following the assaying method of the activity of enzyme which is another present invention as described below, respectively, to obtain the active fraction.

The enzyme-I and the enzyme-II of the present invention also can be prepared by culturing host cells transformed with a plasmid containing a CDNA coding for these enzyme, which can express the cDNA, and collecting either or both of the enzymes from the cultured product produced and accumulated thereby.

The CDNA coding for the enzyme of the present invention which can be used in this method may be any one regardless of its origin, provided that it is derived from a DNA coding for the amino acid sequence a peptide C-terminal amidating enzyme existing in mammals such as human, bovine, horse, porcine, sheep, rabbit, goat, rat, mouse, etc.; avian such as chicken, turkey, etc.; tatrachian such as frog, etc.; reptiles such as snake, etc.; fish such as sardine, mackerel, eel, salmon, etc., and the sequence of Lys-Lys exists at approximately the central portion of the cDNA, but may be preferably one derived from a mammal. More specifically, it is a DNA fragment coding for the amino acid sequence as shown in FIGS. 5(A)–5(F) obtained by inserting the amino acid sequence of a peptide C-terminal amidating enzyme presently known by one letter representation of the amino acid and yet the deficient portion (represented by –) as desired so as to enhance homology between the species, and the CDNA with the portion corresponding to the hydrophobic amino acid region in the vicinity of the C-terminal thereof being removed can be advantageously used. The respective cDNA's are described, for human, horse, bovine, rat, frog I and frog II, respectively in Biochem. Biophys. Res. Commun. 169, 551–558, 1990; Japanese Patent Application No. 2 (1990)-76331; Mol. Endocrinol, 1, p. 777–790, 1987; Proc. Natl. Acad. Sci. USA, 86, p. 735–739, 1989; Biochem. Biophys. Res. Commun., 148, p. 546–552, 1987; and Biochem. Biophys. Res. Commun., 150, 1275–1281, 1988. Of these, for example, according to the sequence of horse in FIGS. 5(A)–5(F), the 441st and the 442th K (lysine) and K (lysine) sequences are correspondent. The sequences are well stored in the cDNA's of human, horse, bovine, rat. The cDNA at the former half portion (5' side) than these sequences codes for the protein having the activity of acting on a peptide C-terminal glycine adduct represented by the formula (I) to produce a peptide C-terminal α-hydroxylglycine represented by the formula (II), while the cDNA at the latter half portion (3' side) than the KK sequences codes for the protein having the activity of acting on a C-terminal glycine adduct to form a C-terminal amidated compound represented by the formula (III) and glyoxylic acid. At the site in the vicinity of such KK sequences, the cDNA can be separated into the former half portion and the latter half portion by use of a restriction endonuclease known per se.

For example, according to the sequence of horse in FIGS. 5(A)–5(F), the region from V (valine) of the 880th to I (isoleucine) of the 901th corresponds to the above-mentioned hydrophobic amino acid region. Therefore, the membrane transport region as mentioned in the present invention refers to the above-mentioned hydrophobic amino acid region of the desired cDNA. Surprisingly, since the cDNA from which the region mentioned above is removed will not only secrete the enzyme produced out of the host all, but also markedly increase the whole amount produced; such a CDNA is particularly preferred for use in the present invention. Since the enzyme-I and the enzyme-II are coded on cDNA mutually adjacent to each other as described above, but these enzymes are released separately by processing in the secretion process in the cells, it is preferable to use the cDNA from which the above-mentioned membrane-transport region is removed. Such a cDNA may be prepared by cutting the portion by using a known restriction endonuclease known per se from the known cDNA, or also can be chosen from various cDNA's formed by difference in splicing of mRNA at the stage of cloning of said cDKA. A CDNA coding for the enzyme-I and the enzyme-II independently which is separated as described above also may be used.

Cloning of the cDNA utilized in the present invention can be practiced according to the method known per se by the use of a diversity of tissues of various animals as mentioned above. Specifically, it is practiced according to the method generally employed, such as the +, – method, hybridization method, PCR method, etc. (see, for example, Methods in Enzymology, Vol. 152; Guide to Molecular Cloning Techniques, S. L. Berger and A. R. Kimmel, editors, 1987, Acadamic Press, INC.; Methods in Molecular Biology, vol. 4; New Nucleic Acid Techniques, J. M. Walker, editor, 1988, The Humana Press Inc.; Molecular Cloning A Laboratory Manual 2nd Ed., J. Sambrook, E. F. Fritsch, T. Maniatis, editors, 1989, Cold Spring Harbor Laboratory Press), the cDNA region coding for the protein is determined by determining the base sequence of the cDNA clone obtained, and the desired cDNA can be obtained by dividing the cDNA at around the KR sequence portion at the central portion as described above.

Referring to an example of rat, a tissue which forms abundantly a peptide C-terminal amidating enzyme, for example, a pituitary of rat is homogenized together with guanidyl thiocyanate to crush the cells, and RNA fraction is obtained by cecium chloride equilibration density gradient ultra-centrifugation. Subsequently, by affinity chromatography having an oligo-dT-cellulose carried thereon, an RNA having a poly-A (poly-$A^+$RNA) is isolated from the above-mentioned RNA fraction.

By use of the poly-ARNA as the template, a cDNA library is obtained according to the method known in the art, preferably the method of Okayama-Berg (Mol. Cell. Biol. 2, 161, 1982). From these cDNA libraries, an appropriate probe can be used to screen a positive clone, a positive cDNA clone obtained by rescreening by use of an appropriate probe from the amplified cDNA libraries isolated, and the structure of the desired cDNA can be determined by mapping and sequencing these restriction endonuclease. Also, by incorporating the above-mentioned CDNA into an expression vector, and evaluating the productivity of the peptide C-terminal amidating enzyme of the host transformed therewith, a plasmid containing the desired cDNA can be selected.

The host for expressing the cDNA may be cells of microorganisms such as *E. coli., Bacillus subtilis*, yeast, etc., cultured cells derived from insects, animals, etc., conventionally used. The expression plasmid may be any plasmid which can express efficiently the cDNA in these cells. For example, it can be appropriately chosen from those described in the textbooks as shown below.

Zoku Seikagaku Jikken Koza I, Idenshi Kenkyuho II—Recombinant DNA technique—Chapter 7 Expression of Recombinant (1986), edited by Society of Biochemical Society of Japan, Tokyo Kagaku Dojin; Recombinant DNA, Part D, Section II, Vectors for Expression of Cloned Genes, (1987) edited by Raywu and Lawrence Grossman, Academic Press, INC.; Molecular Cloning, A Laboratory Manual 2nd Ed. Book 3, (1989) edited by J. Sambrook, E. F. Fritsch and T. Maniatis, Cold Spring Harbor Laboratory Press; etc.

For example, when CV-1 conventionally used as the animal culturing cells is used as the host, a promotor of the type pSV, pL2n, pCol and having optionally formulated a selection marker therewith can be used. As for *E. coli*, a vector of the type pGH, pKYP, pHUB, while for yeast, a type of YRp, YEp can be used. Recombination with these cDNA's of these vectors, and transformations, transfections of the host cells with the recombinant plasmids can be practiced according to the procedures of the methods known per se described in the literatures as mentioned above. The transformed cells -thus obtained can be cultured in a medium and under cultural conditions conventionally used for proliferation of the cells derived.

The peptide C-terminal amidating enzyme produced and accumulated from such cultured product can be collected easily from the culture broth after removal of the cells in the case of, for example, using animal cultured cells, because the produced enzyme is excreted out of the cells, but may be also collected from the cell lyzate, if necessary. Such collection and purification can be practiced by conventional enzyme purification methods, such as combination of fractionation by precipitation, heparin affinity chromatography and dialysis, etc., but further preferably by joint use of the substrate affinity chromatography with the use of the peptide C-terminal glycine adduct as the ligand.

According to FIGS. 5(A)–5(F), the enzyme-I of the present invention corresponds to the amino acid sequence from the 42th residue P or S to the 442th residue K in the case of human, horse, bovine and rat, and corresponds to the amino acid sequence from the 42th residue P or S to the 231th residue K in the case of horse and bovine. On the other hand, the enzyme-II obtained corresponds to the amino acid sequence from the 443th residue D to the 830th residue K in the case of human, horse, bovine and rat respectively. The term "ucorresponding" as used herein includes those to which a saccharide is bonded through N-acetylglucosamine.

Use of enzyme

The present invention provides the use of the enzyme of the present invention as described below, i.e., a method of producing a peptide C-terminal α-hydroxylglycine adduct represented by the above formula (II), which comprises treating a peptide C-terminal glycine adduct represented by the above formula (I) with the above enzyme-I, and a method of producing a peptide C-terminal amidated compound represented by the above formula (III) which comprises treating the above adduct represented by the formula (II) with the enzyme-II. Also, by use of these enzyme-I and enzyme-II in combination, the compound of the formula (I) can be converted to the compound of the formula (III) in a single reaction composition. The use of the enzyme-II in the step of converting the compound from the formula (I) to the formula (III) would be clearly understood to be significant, because the above-mentioned conversion can be accomplished under milder enzyme reaction conditions compared with the case under the presence only of the enzyme of the enzyme-I type where it must be subjected to chemical hydrolysis conditions in converting the compound from the formula (II) to the formula (III). Particularly, these methods are suitable for a treatment of unstable substrates under alkaline conditions.

The preparation methods can be used, provided they contain the enzyme of the present invention, regardless of the concentration, purity, but it is advantageous to use the enzyme containing product from which the intervening proteins are removed to great extent, in view of isolation purification the product from the reaction mixture of the compound of the formula (II).

As the compounds of the formula (I) and (II), all of those described above are included, the corresponding compounds represented by the formula (I) or the formula (II) which can be converted according to the present preparation method to the compound of the formula (III), for example, arginine vasotocin (AVT), lutenizing hormone-release hormone (LH-RH), oxytocin, gastrin, gastrin secretion promoting peptide (GGRP), calcitonin (CT), vasoactive intestinal polypeptide (VIP), throtropin-releasing hormone (TRH), melanophore stimulating hormone (MSH), MSH release inhibiting hormone (MIH), cholecystokinin-octapeptide (CCK-8), substance P (SP), adipokinin, pancreatic polypeptide (PP) growth hormone releasing factor, secretin, caerulein, mollusk cardiostimulant neuropeptide, vasopressin, adrenocoricotropic hormone (ACTH), allochroic hormone, bombesin, light adaptation hormone, motilin, apamin, allitecine, eredoicin, catcinin, granulibelline R, scotophobin, hyranbatecaerulein, obesity cell degranulation peptide, physaremin, phyllocaerulein, phyllomezcin, promellitin, bombinin, mastoballan, manitoballan-X, mellitin-1, lanatensin, lanatensin-R.

The above-mentioned treatment can be practiced in a common buffer, particularly with addition of ascorbic acid and catalase in the reaction mixture in the reaction by use of the enzyme-I, but it is preferable to practice the reaction in view of the conditions of the assaying method of enzyme activity as shown below.

Assaying method of enzyme activity and screening method of novel enzyme by use thereof The enzyme-I and the enzyme-II of the present invention as described above can be monitored according to the assaying method of activity as described below, and the assaying method is useful for practicing the preparation method of the present enzymes as described above.

These assaying methods are based on the finding that the peptide C-terminal amidating reaction is not a one-step reaction as considered in the prior art, but a two-step reaction through an intermediate (peptide C-terminal α-hydroxylglycine adduct).

Initially, the activity of the enzyme-I is assayed according to the method comprising step (a) of buffering a sample to be tested expected to have its activity to pH 5 to 8, and step (b) of adding a peptide C-terminal glycine adduct represented by the above formula (I), L-ascorbic acid and catalase to the buffer followed by incubation, and then measuring the product represented by the formula (II), which has been isolated by chromatography described later, or measuring the product, which has been converted from the compound (II) into the compound (III) under alkaline conditions and then isolated. As a preferable isolation measurement, there may be used the step of detecting the reaction product by HPLC with the use of an acetonitrile-containing buffer (pH 6–10).

The activity of the enzyme-II is assayed according to the method comprising the step (a) of buffering a sample to be tested expected to have its activity to pH 4 to 8, the step (b) of adding a C-terminal α-hydroxylglycine adduct represented by the formula (II) to the buffer followed by incubation, and then detecting the reaction product of the formula (III) or glyoxylic acid by the method known per se. The activity of the enzyme-II is also preferably detected by the above HPLC.

As the sample to be tested as mentioned in the present invention, there may be included any fluid having those activities, particularly biological fluids having those activities, namely homogenates of biological organs, as well as body fluids, such as blood and lymph, and further treated solutions of these obtained by purification treatment, etc. Also, treated solutions derived from microorganism cells are included in the biological fluid.

The buffering agent to be used for the buffering these samples to be tested is not particularly limited, but those conventionally used may be employed. For example, tris-hydrochloric acid and hepes-potassium hydroxide may be included. The concentration of the buffering agent in the buffer may be any concentration, provided that the buffering action can be accomplished, with a concentration of 20 to 200 mM being suitable in general.

The respective buffers may be controlled to pH 6 to 8, preferably pH 6.5, for the former method, while pH 4 to 8, preferably around pH 6 for the latter method. As the peptide C-terminal glycine adduct to be added to the buffer thus prepared in the former, it is preferable to use one which is a substrate for said enzyme, and represented by the formula (I) enumerated as preferable substrate for identifying the activity of the enzyme-I as described above. The concentration of the compound should be suitably about 0.1 $\mu$M to 2 mM. Further, it is required to add L-ascorbic acid which is considered to function as the cofactor, and catalase as the activating agent. Generally speaking, the concentration of L-ascorbic acid may be preferably 0.5 to 2 mM, and the concentration of catalase suitably 40 to 100 $\mu$g/ml. A metal ion may be also added in the buffer, but this addition is not particularly required for the present activity assay, which addition however is preferable because higher activity may be sometimes obtained as compared in the case of no addition. As the metal ion to be employed, $Zn^{2+}$, $Cu^{2+}$, $Ni^{2+}$, $Ni^{2+}$, $Co^{2+}$, $Fe^{3+}$, etc. is appropriate, particularly preferably $Cu^{+}$ and $Zn^{2+}$ The concentration of the metal ion in the buffer may be suitably 0 to 1000 $\mu$M, preferably 0 to 10 $\mu$M. The compounds for providing such metal ions are not particularly limited, but may include $CuSO_4$, $CuCl_2$ $ZnCl_2$, $NiCi_2$, $CoCi_2$, $FeCl_3$, etc.

For a specific example of such reaction composition, reference may be made to the reaction composition A of Example 7 as described below. On the other hand, the reaction composition in the latter is prepared by use of the corresponding compound of the formula (II) in place of the above formula (I). In this case, no cofactor such as ascorbic acid, catalase, etc. is required.

In these both assaying methods, the amount of the test sample employed is not particularly limited and can be varied, but preferably is suitably adjusted to contain a pmol/hr or more, more preferably 10× a pmol/hr or more, most preferably 10× a pmol/hr to a mol/hr, based on the amount of the substrate existing in the reaction system (defined as a nanomol (nmol)) [unit indicates enzyme activity, represented in the substrate amount which can be reacted at 37° C. for one hour (e.g., picomol (pmol)].

Incubation may be carried out at 1 to 55° C., particularly in the former preferably 25 to 40° C., particularly preferably around 30° C. with stirring for 2 to 24 hours, while in the latter preferably at 15 to 35° C., most preferably around 25° C. stationarily for one minute to 48 hours.

For detection of the compound of the formula (II) and the compound of the formula (III) formed respectively in the steps as described above, there can be employed and method which can measure by separation those substrate and the product, for example, the compound of the formula (I) and the compound of the formula (II) in the former, while the compound of the formula (II) and the compound of the formula (III) in the latter. Generally speaking, separation measurement can be conducted by separation, purification by chromatography as mentioned below. As the chromatography which can be used for the above treatment, there may be included ion-exchange chromatography, reverse phase chromatography, gel filtration, affinity chromatography, high performance liquid chromatography (HPLC), thin layer chromatography (TLC), etc. The substrate represented by the formula (II) and the amidated product represented by the formula (III) in the reaction system of the latter have peptide C-terminals of carboxyl group and amide group, respectively, with the charges being different. Ion-exchange chromatography, reverse phase chromatography, etc. using this property are preferred. Affinity chromatography by use of the antibody of the product may be also effectively used. However, although separation of the substrate represented by the formula (I) and the product represented by the formula (II) in the reaction system of the former, according to the high performance liquid chromatography (HPLC) with the use of an acetonitrile containing buffer (pH 6 to 10, preferably pH 9) as the eluate attempted for the first time by the present inventors, separation measurement can be done advantageously. The eluate should be particularly preferably applied with a straight line concentration gradient of acetonitrile concentration. As the column for HPLC, any kind of commercially available columns suited for the present object can be used, but it is particularly advantageous to use Capcell Pak C18SG, 300 Å (produced by Shiseido).

The substrate and the product thus separated may be assayed for either the chemical or physical labels (optionally bound) of them. For such measurement, known labels, known assaying methods can be used, and it would be generally convenient to utilize the UV-absorption derived from the amino acid constituting the substrate peptide.

Since the assaying methods as described are correct and simple, by applying these to the biological fluids as mentioned above, the enzymes having the respective activities of the enzyme-I and the enzyme-II, can be searched. Such searching methods are provided as the eighth and the ninth inventions of the present application, respectively.

The biological fluid to be searched is inclusive of those of which enzymatic activity can be expected as described above, as a matter of course, and also all of living body cells, tissues, extracts of other animals and vegetables. For example, extracts may be prepared according to the extraction methods in general, as described in "Jikken Seibutsugaku Koza 6, Saibo Bunkakuho" (Maruzen, 1984), "Seikagaku Jikken Koza 5, Kosokenkyuho (Former)" (Tokyo Kagaku Dojin, 1975), "Kiso Seikagaku Jikkenho 1, Seibutsu Zairyo no Toriatsukaikata" (Maruzen, 1974).

DNA Sequences for Enzyme-I and Enzvme-II Derived from Horse

According to the present invention, there is provided a CDNA sequence coding for a polypeptide having a peptide C-terminal activities of enzyme-I and the enzyme-II. Since these enzymes provide the possibility of an excellent activity and stability in comparison with those of peptide C-terminal amidating enzymes known in the art (see Published International Application: WO89/1209), the reasons for providing the above DNA sequences will be clear. For the source of the enzyme, any kind may be available, provided that it is an organ or a tissue where the such enzyme exists, but primarily those derived from atrium, pituitary gland, brain or stomach are to be used.

The CDNA coding for the peptide having the C-terminal amidating enzyme activity according to the present invention is specifically shown in FIGS. 13(A) –13(P). In this Figure, the base sequence of the longest cDNA fragment and the amino acid sequence coded for thereby is shown by one letter representation. The content within the [ ] FIGS. 13(A)–13(P) (No. 4) is a cDNA deleted portion which appears to be formed through the difference in mRNA splicing found as the result of analysis of some cDNA's. Therefore, several kinds of the CDNA according to the present invention exist also for the amino acid sequences of the polypeptide to be coded for thereby. For example, as for the amino acid sequence of the polypeptide having the peptide C-terminal amidating enzyme activity derived from horse as described in the present invention, there exist 4 kinds having at least the common sequence up to a certain chain length and the 4 kinds of sequences, respectively, upstream thereof.

| Common amino acid sequence |
|---|
| 10 20 |
| MetAlaGlyLeuArgSerLeuLeuValLeuLeuLeuValPheGlnSerSerCysLeuGly |
| 30 40 |
| PheArgSerProLeuSerValPheLysArgPheLysGluThrThrArgProPheSerAsn |
| 50 60 |
| GluCysLeuGlyThrThrArgProValIleProIleAspSerSerAspPheAlaLeuAsp |
| 70 80 |
| IleArgMetProGlyValThrProLysGlnSerAspThrTyrPheCysMetSerMetArg |
| 90 100 |
| LeuProMetAspGluGluThrPheValIleAspPheLysProArgAlaSerMetAspThr |
| 110 120 |
| ValHisHisMetLeuLeuPheGlyCysAsnMetProSerSerThrGlySerTyrTrpPhe |
| 130 140 |
| CysAspGluGlyValCysThrAspLysAlaAsnIleLeuTyrAlaTrpAlaArgAsnAla |
| 150 160 |
| ProProThrArgLeuProLysGlyValGlyPheArgValGlyGlyGluThrGlySerLys |
| 170 180 |
| TyrPheValLeuGlnValHisTyrGlyAspIleSerAlaPheArgAspAsnHisLysAsp |
| 190 200 |
| CysSerGlyValSerLeuHisLeuThrArgLeuProGlnProLeuIleAlaGlyMetTyr |
| 210 220 |
| LeuMetMetAlaLeuAspThrValIleProAlaGlyGluLysValValAsnSerAspLeu |
| 230 240 |
| SerCysHisTyrLysLysTyrProMetHisValPheAlaTyrArgValHisThrHisHis |
| 250 260 |
| LeuGlyLysValValSerGlyTyrArgValArgAsnGlyGlnTrpThrLeuIleGlyArg |
| 270 280 |
| GlnSerProGlnLeuProGlnAlaPheTyrProValGluHisProValAspValSerPhe |
| 290 300 |
| GlyAspIleLeuAlaAlaArgCysValPheThrGlyGluGlyArgThrGluAlaThrHis |
| 310 320 |
| IleGlyGlyThrSerSerAspGluMetCysAsnLeuTyrIleMetTyrTyrMetGluAla |
| 330 340 |
| LysHisAlaValSerPheMetThrCysThrGlnAsnValAlaProGluMetPheArgThr |
| 350 360 |
| IleProProGluAlaAsnIleProIleProValLysSerAspMetValMetMetHisGly |
| 370 380 |
| HisHisLysGluThrGluAsnLysAspLysThrSerLeuGlnGlnProLysGlnGluGlu |
| 390 400 |
| GluValLeuGluGlnGlyAspPheTyrSerLeuLeuSerLysLeuLeuGlyGluArgGlu |
| 410 420 |
| AspValValHisValHisLysThrAsnProThrGluLysAlaGluSerGluSerAspLeu |
| 430 440 |
| ValAlaGluIleAlaAsnValValGlnLysLysAspLeuGlyArgSerAspAlaArgGlu |
| 450 460 |
| SerAlaGluHisGluAspArgGlyAsnAlaIleLeuValArgAspArgIleHisLysPhe |
| 470 480 |
| HisArgLeuGluSerThrLeuArgProThrGluSerArgValIleSerValProGlnPro |
| 490 500 |
| LeuProGlyGluGlyThrTrpGluProGluHisThrGlyAspPheHisValGluGluAla |
| 510 520 |
| LeuAspTrpProGlyValTyrLeuLeuProGlyGlnValSerGlyValAlaLeuAspLeu |
| 530 540 |
| GlnAsnAsnLeuValIlePheHisArgGlyAspHisValTrpAspGlyAsnSerPheAsp |
| 550 560 |
| SerLysPheValTyrGlnGlnArgGlyLeuGlyProIleGluGluAspThrIleLeuVal |
| 570 580 |
| IleAspProAsnAsnAlaAlaValLeuGlnSerSerGlyLysAsnLeuPheTyrLeuPro |
| 590 600 |
| HisGlyLeuSerIleAspLysAspGlyAsnTyrTrpValThrAspValAlaLeuHisGln |
| 610 620 |
| ValPheLysLeuAspProAsnSerLysGluGlyProLeuLeuIleLeuGlyArgSerMet |
| 630 640 |
| GlnProGlySerAspGlnAsnHisPheCysGlnProThrAspValAlaValAspProAsu |
| 650 660 |
| ThrGlyThrIlePheValSerAspGlyTyrCysAsnSerArgIleValGlnPheSerPro |
| 670 680 |
| ThrGlyArgPheIleThrGlnTrpGlyGluGluSerSerGluSerAsnProLysProGly |
| 690 700 |
| GlnPheArgValProHisSerLeuAlaLeuValProHisLeuGlyGlnLeuCysValAla |
| 710 720 |
| AspArgGluAsnGlyArgIleGlnCysPheLysThrAspThrLysGluPheValArgGlu |
| 730 740 |
| IleLysHisAlaSerPheGlyArgAsnValPheAlaIleSerTyrIleProGlyLeuLeu |
| 750 760 |
| PheAlaValAsnGlyLysProTyrPheGlyAsnGlnLysProValGlnGlyPheValMet |
| 770 780 |

-continued

| Common amino acid sequence |
|---|
| AsnPheSerSerGlyGluIleIleAspValPheLysProValArgLysHisPheAspMet |
| 790 800 |
| ProHisAspIleThrAlaSerGluAspGlyThrValTyrValGlyAspAlaHisThrAsn |
| ThrValTrpLysPheThrSerThrGlu |

| Amino acid sequences in different regions |
|---|
| (i) |
| 810 820 |
| ThrAlaGlnValTrpPheProGlyValAspLeuHisHisSerSerValAlaMetLeuTrp |
| 830 840 |
| TrpGlnLeuThrTyrLysLysArgLysIleAspAsnArgCysTyrLeuArgAlaAsnLeu |
| 850 860 |
| ProGlnGlnMetLysLysLysArgValGluHisArgSerValLysLysAlaGlyIleGlu |
| 870 880 |
| ValGlnGluIleLysGluSerGluAlaValValGluThrLysMetGlyAsnLysProAla |
| 890 900 |
| SerSerGluLeuGlnLysMetGlnGluLysGlnLysLeuIleLysGluProGlySerGly |
| 910 920 |
| ValProValValLeuIleThrThrLeuLeuValIleProValValValLeuLeuAlaIle |
| 930 940 |
| AlaIlePheIleArgTrpLysLysSerArgAlaPheGlyGluSerGluHisLysValGlu |
| 950 960 |
| AlaSerSerGlyArgValLeuGlyArgLeuArgGlyLysGlySerGlyGlyLeuAsnLeu |
| 970 980 |
| GlyAsnPhePheAlaSerArgLysGlyTyrSerArgLysGlyPheAspArgLeuSerThr |
| 990 1000 |
| GluGlySerAspGlnGluLysAspGluAspAspGlySerGluSerGluGluGluTyrSer |
| 1010 1020 |
| AlaProLeuProAlaProValProSerSerSer |
| (ii) |
| 810 820 |
| ArgValGluHisArgSerValLysLysAlaGlyIleGluValGlnGluIleLysGluSer |
| 830 840 |
| GluAlaValValGluThrLysMetGluAsnLysProAlaSerSerGluLeuGlnLysMet |
| 850 860 |
| GlnGluLysGlnLysLeuIleLysGluProGlySerGlyValProValValLeuIleThr |
| 870 880 |
| ThrLeuLeuValIleProValValValLeuLeuAlaIleAlaIlePheIleArgTrpLys |
| 890 900 |
| LysSerArgAlaPheGlyGluSerGluHisLysValGluAlaSerSerGlyArgValLeu |
| 910 920 |
| GlyArgLeuArgGlyLysGlySerGlyGlyLeuAsnLeuGlyAspPhePheAlaSerArg |
| 930 940 |
| LysGlyTyrSerArgLysGlyPheAspArgLeuSerThrGluGlySerAspGlnGluLys |
| 950 960 |
| AspGluAspAspGlySerGluSerGluGluGluTyrSerAlaProLeuProAlaProVal |
| 970 |
| ProSerSerSer |
| (iii) |
| 810 820 |
| ThrAlaGlnValTrpPheProGlyValAspLeuHisHisSerSerValAlaMetLeuTrp |
| 830 840 |
| TrpGlnLeuThrTyrLysLysArgLysIleAspAsnArgCysTyrLeuArgAlaAsnLeu |
| 850 860 |
| ProGlnGlnMetLysLysLysArgValGluHisArgSerValLysLysAlaGlyIleGlu |
| 870 880 |
| ValGlnGluIleLysAlaGluSerGluHisLysValGluAlaSerSerGlyArgValLeu |
| 890 900 |
| GlyArgLeuArgGlyLysGlySerGlyGlyLeuAsnLeuGlyAsnPhePheAlaSerArg |
| 910 920 |
| LysGlyTyrSerArgLysGlyPheAspArgLeuSerThrGluGlySerAspGlnGluLys |
| 930 940 |
| AspGluAspAspGlySerGluSerGluGluGluTyrSerAlaProLeuProAlaProVal |
| 950 |
| ProSerSerSer, and |
| (iv) |
| 810 820 |
| ArgValGluHisArgSerValLysLysAlaGlyIleGluValGlnGluIleLysAlaGlu |
| 830 840 |
| SerGluHisLysValGluAlaSerSerGlyArgValLeuGlyArgLeuArgGlyLysGly |
| 850 860 |

-continued

| Amino acid sequences in different regions |
|---|
| SerGlyGlyLeuAsnLeuGlyAsnPhePheAlaSerArgLysGlyTyrSerArgLysGly |
| 870 880 |
| PheAspArgLeuSerThrGluGlySerAspGlnGluLysAspGluAspAspGlySerGlu |
| 890 900 |
| SerGluGluGluTyrSerAlaProLeuProAlaProValProSerSerSer |

The polypeptides having these amino acid sequences can be translated not merely by the 4 kinds of CDNA sequences, but also by use of a DNA comprising a combination of different codons coding for the same amino acid, and the DNA sequences of the present invention are inclusive of all of those. Further, it may be interpreted that, even if a part of the amino acid sequence may be modified by replacement, addition or removal to the extent that the C-terminal admidating enzyme activity is not lost, such a modified sequence can be suitable for the purpose of the present invention. Specific examples of these may include those having the common base sequence shown below and the respective different base sequence portions downstream thereof.

Common base sequence

CGGCGTGGA CATGGCTGGC CTTCGTAGCC TGCTAGTTCT CCTCCTTGTT
TTTCAGAGCA GCTGTTTGGG TTTCAGAAGC CCACTTTCTG TCTTTAAGAG
GTTTAAAGAA ACTACCAGAC CATTTTCCAA TGAATGTCTT GGTACCACCA
GACCAGTCAT TCCTATTGAT TCATCAGATT TTGCATTGGA TATTCGCATG
CCTGGAGTCA CACCTAAACA GTCTGATACA TACTTCTGCA TGTCGATGCG
TTTGCCAATG GATGAGGAAA CCTTCGTGAT TGACTTCAAA CCTCGTGCCA
GCATGGATAC TGTCCATCAT ATGTTACTTT TTGGTTGCAA TATGCCCTCA
TCCACTGGAA GTTACTGGTT TTGTGATGAA GCCGTCTGTA CAGACAAAGC
CAATATTCTC TATGCCTGGG CAAGAAATGC TCCCCCCACC AGACTCCCCA
AAGGTGTTGG ATTCAGAGTT GGAGGAGAGA CTGGAAGTAA ATACTTCGTA
CTACAAGTAC ACTATGGGGA TATTAGTGCT TTTAGAGATA ATCACAAGGA
CTGTTCTGGT GTGTCCTTAC ACCTCACACG CCTGCCACAG CCTTTAATTG
CTGGCATGTA CCTTATGATG GCTCTTGACA CTGTTATACC AGCAGGAGAG
AAAGTGGTGA ATTCTGACCT TTCATGCCAT TATAAAAAGT ACCCAATGCA
TGTCTTTGCC TATAGAGTTC ACACTCACCA TTTAGGTAAG GTAGTAAGTG
GCTACAGAGT AAGAAATGGA CAGTGGACAC TGATTGGACG TCAGAGCCCC
CAGCTGCCAC AGGCTTTCTA CCCTGTGGAA CACCCAGTAG ATGTCAGTTT
TGGTGACATA CTGGCAGCAA GATGTGTGTT CACTGGTGAA GGAAGGACAG
AAGCCACGCA CATTGGTGGC ACATCTAGTG ATGAAATGTG CAACTTATAC
ATTATGTATT ACATGGAAGC CAAGCACGCA GTTTCTTTCA TGACCTGTAC
CCAGAATGTA GCTCCAGAAA TGTTCAGAAC CATCCCCCCA GAGGCCAATA
TTCCAATTCC TGTGAAGTCC GACATGGTTA TGATGCATGG ACATCACAAA
GAAACAGAGA ACAAAGATAA GACTTCACTA CAACAGCCAA AACAAGAAGA
AGAAGTGTTA GAACAGGGTG ATTTCTATTC ACTGCTTTCC AAGCTGCTAG
GAGAAAGGGA AGATGTTGTT CATGTGCATA AATATAACCC TACAGAAAAG
GCAGAATCAG AGTCAGACCT GGTAGCTGAG ATTGCAAATG TAGTCCAAAA
GAAGGATCTC GGTCGATCTG ATGCCAGAGA GAGTGCAGAG CATGAGGACA
GGGGCAATGC TATTCTTGTC AGAGACAGAA TTCACAAATT CCACAGACTA
GAATCTACTT TGAGGCCAAC AGAGAGCAGA GTTATCTCAG TACCGCAGCC
CCTACCTGGT GAAGGCACCT GGGAACCAGA ACACACAGGA GATTTCCATG
TAGAAGAGGC ACTGGATTGG CCTGGAGTAT ACTTGTTACC AGGCCAGGTT
TCTGGGGTAG CTCTGGACCT TCAGAATAAC CTGGTGATTT TCCACAGAGG
TGACCATGTC TGGGATGGAA ACTCTTTTGA CAGCAAGTTT GTGTACCAGC
AAAGAGGACT CGGGCCAATT GAAGAAGATA CTATTCTTGT CATAGATCCA
AATAATGCTG CAGTCCTCCA GTCCAGTGGA AAAAATCTGT TTTACTTGCC
ACATGGCTTG AGCATAGACA AAGATGGAAA TTATTGGGTC ACAGACGTGG
CTCTCCATCA GGTGTTCAAA CTGGATCCAA ACAGTAAAGA AGGCCCTCTG
TTGATCCTGG GAAGAAGCAT GCAACCAGGC AGTGACCAGA ATCACTTCTG
TCAACCCACC GATGTGGCTG TAGATCCAAA CACTGGGACC ATCTTTGTAT
CAGATGGTTA CTGCAACAGT CGGATCGTGC AGTTTTCACC AACTGGAAGG
TTCATCACAC AGTGGGGAGA AGAGTCTTCT GAGAGCAATC CTAAACCAGG
CCAGTTCAGG GTTCCTCACA GCTTGGCCCT TGTGCCTCAT TTGGGCCAAT
TATGTGTGGC CGACCGGGAA AATGGTCGGA TCCAGTGTTT TAAAACTGAC
ACCAAAGAAT TTGTGCGAGA GATTAAGCAT GCATCATTTG GAAGAAATGT
ATTTGCAATT TCGTATATAC CAGGTTTGCT CTTTGCCGTA AATGGGAAGC
CTTACTTTGG GGACCAAAAA CCAGTACAAG GATTTGTGAT GAACTTTTCC
AGTGGGGAAA TTATAGATGT CTTCAAGCCA GTGCGCAAGC ACTTTGACAT
GCCTCATGAC ATTACTGCAT CTGAAGACGG GACTGTGTAT GTTGGAGATG
CTCACACCAA CACCGTGTGG AAGTTCACTT CGACTGAA

Different base sepuence portions (i)

AC AGCCCAGGTC
TGGTTCCCGG GTGTGGACCT ACATCACTCG TCAGTGGCCA TGCTGTGGTG
GCAGCTCACA TACAAAAAGA GGAAGATTGA CAACAGATGT TATCTCAGGG

-continued

CCAATCTTCC TCAGCAAATG AAAAAAAAAA GAGTGGAGCA TCGATCAGTT
AAAAAGGCTG GCATTGAGGT CCAGGAAATC AAAGAATCCG AGGCAGTTGT
TGAAACCAAA ATGGAGAACA AACCCGCCTC CTCAGAATTG CAGAAGATGC
AAGAGAAACA GAAACTGATC AAAGAGCCAG GCTCGGGAGT GCCCGTTGTT
CTCATTACAA CCCTTCTGGT TATTCCGGTG GTTGTCCTGC TGGCCATTGC
CATATTTATT CGGTGGAAAA AATCAAGGGC CTTTGGAGAG TCTGAACACA
AAGTCGAGGC AAGTTCAGGA AGAGTACTGG GAAGACTTAG AGGAAAAGGA
AGTGGAGGCT TAAACCTCGG AAATTTCTTT GCGAGCCGTA AAGGCTACAG
TCGGAAAGGG TTTGACCGGC TCAGCACCGA GGGGAGTGAC CAGGAGAAAG
ATGAGGATGA CGGAAGTGAA TCAGAAGAAG AATATTCAGC ACCTCTGCCC
GCACCTGTAC CTTCCTCCTC CTGAAAACTG GGCTTTGATT TAGTTGATGA
GATTTACCAA GAATGCCAGG TTCCTTTCCC TTTAGCACGA TTAGAGTTTT
GTGTATTTAA TTGTAAACTG TACTAGTCTG TGTGGGACTG TACACATTTT
ATTTACTTCG TTTTGGTTTA GTTGGCTTCT GTTTCTGGTT GAGGAGTTTC
CTAAAAGTTC ATAACAGTGC CATTGTCTTT ATCTGAACAT AGAATAGAGA
AACAGTCCTC TTCTTCCATC ACGTTACTAA TTTAATGATG GAAGCTTTGC
TCATTTACAT TTTGAGACTT TTCTGTAGGT GTAAATAGCC CCATTCTCTG
CTTGGACACA GTCTTTTCCC AATAGCACTT CCATTGCCAG TGTCTTTCTT
TGGTGCCTTT CCTGTTCAGC ATTCTCAGCC TGTGGCAGTA AAGAGAAACT
TTGTGCTACA CGACGACGAA GCTGCTAAAT CTTCTTCTAT TTTTTTAAAA
TCACTAACAT TATATTGCAA CAAGGGAAAG AAAAAAGTCT CTATTTAAAT
TCTTTTTTTT AAATTTTCTT CTTTAGTTGG TGTGTTTTTG GGATGTCTTA
TTTTTAGATG GTTACACTGT TAGAACACTA TTTTCAGAAT CTGAATGTAA
TTTGTGTAAT AAAGTGTTTT CAGAGCATTA GCTGTCAGAG TGTATTTTGC
CAATTTTTGC ATATGTCCAG GGTTTTGTAT ACTTTTGTAA TAATTACATA
AACCACAGAT TGAGTGAAAC CTACTCAATG TCTTCAACCA AAAGAAATGT
GTTGTATTGT ATTAAAATCA AGAAGATATT TTGTTATGTA GCTGATACAA
ATTAAAAACC AGCCTAAGAG CTTACATACA TGTGTAAAAT CAGGCTCTCT
GATGATTCAA CGAGAGTGTT TGCCTGTATA TCAATCAGAA GGTAAATATC
TGAATAAAAG GTGATCATAG CTGAGAGGAA AAAAAAAAAA AAAAAA (ii)

AG AGTGGAGCAT
CGATCAGTTA AAAAGGCTGG CATTGAGGTC CAGGAAATCA AAGAATCCGA
GGCAGTTGTT GAAAGCAAAA TGGAGAACAA ACCCGCCTCC TCAGAATTGC
AGAAGATGCA AGAGAAACAG AAACTGATCA AAGAGCCAGG CTCGGGAGTG
CCCGTTGTTC TCATTACAAC CCTTCTGGTT ATTCCGGTGG TTGTCCTGCT
GGCCATTGCC ATATTTATTC GGTGGAAAAA ATCAAGGGCC TTTGGAGAGT
CTGAACACAA AGTCGAGGCA AGTTCAGGAA GAGTACTGGG AAGACTTAGA
GGAAAAGGAA GTGGAGGCTT AAACCTCGGA AATTTCTTTG CGAGCCGTAA
AGGCTACAGT CGGAAAGGGT TTGACCGGCT CAGCACCGAG GGGAGTGACC
AGGAGAAAGA TGAGGATGAC GGAAGTGAAT CAGAAGAAGA ATATTCAGCA
CCTCTGCCCG CACCTGTACC TTCCTCCTCC TGAAAACTGG GCTTTGATTT
AGTTGATGAG ATTTACCAAG AATGCCAGGT TCCTTTCCCT TTAGCACGAT
TAGAGTTTTG TGTATTTAAT TGTAAACTGT ACTAGTCTGT GTGGGACTGT
ACACATTTTA TTTACTTCGT TTTGGTTTAG TTGGCTTCTG TTTCTGGTTG
AGGAGTTTCC TAAAAGTTCA TAACAGTGCC ATTGTCTTTA TCTGAACATA
GAATAGAGAA ACAGTCCTCT TCTTCCATCA CGTTACTAAT TTAATGATGG
AAGCTTTGCT CATTTACATT TTGAGACTTT TCTGTAGGTG TAAATAGCCC
CATTCTCTGC TTGGACACAG TCTTTTCCCA ATAGCACTTC CATTGCCAGT
GTCTTTCTTT GGTGCCTTTC CTGTTCAGCA TTCTCAGCCT GTGGCAGTAA
AGAGAAACTT TGTGCTACAC GACGACGAAG CTGCTAAATC TTCTTCTATT
TTTTTAAAAT CACTAACATT ATATTGCAAC AAGGGAAAGA AAAAAGTCTC
TATTTAAATT CTTTTTTTTA AATTTTCTTC TTTAGTTGGT GTGTTTTTGG
GATGTCTTAT TTTTAGATGG TTACACTGTT AGAACACTAT TTTCAGAATC
TGAATGTAAT TTGTGTAATA AAGTGTTTTC AGAGCATTAA AAAAAAAAAA
AAAAAAAAAA AAAAAAAAAA AAAAAAAAAA A (iii)

AC AGCCCAGGTC
TGGTTCCCGG GTGTGGACCT ACATCATCG TCAGTGGCCA TGCTGTGGTG
GCAGCTCACA TACAAAAAGA GGAAGATTGA CAACAGATGT TATCTCAGGG
CCAATCTTCC TCAGCAAATG AAAAAAAAAA GAGTGGAGCA TCGATCAGTT
AAAAAGGCTG GCATTGAGGT CCAGGAAATC AAAGCAGAGT CTGAACACAA
AGTCGAGGCA AGTTCAGGAA GAGTACTGGG AAGACTTAGA GGAAAAGGAA
GTGGAGGCTT AAACCTCGGA AATTTCTTTG CGAGCCGTAA AGGCTACAGT
CGGAAAGGGT TTGACCGGCT CAGCACCGAG GGGAGTGACC AGGAGAAAGA
TGAGGATGAC GGAAGTGAAT CAGAAGAACA ATATTCAGCA CCTCTGCCCG
CACCTGTACC TTCCTCCTCC TGAAAACTGG GCTTTGATTT AGTTGATGAG
ATTTACCAAG AATGCCAGGT TCCTTTCCCT TTAGCACGAT TAGAGTTTTG
TGTATTTAAT TGTAAACTGT ACTAGTCTGT GTGGGACTGT ACACATTTTA
TTTACTTCGT TTTGGTTTAG TTGGCTTCTG TTTCTGGTTG AGGAGTTTCC
TAAAAGTTCA TAACAGTGCC ATTGTCTTTA TCTGAACATA GAATAGAGAA
ACAGTCCTCT TCTTCCATCA CGTTACTAAT TTAATGATGG AAGCTTTGCT
CATTTACATT TTGAGACTTT TCTGTAGGTG TAAATAGCCC CATTCTCTGC
TTGGACACAG TCTTTTCCCA ATAGCACTTC CATTGCCAGT GTCTTTCTTT
GGTGCCTTTC CTGTTCAGCA TTCTCAGCCT GTGGCAGTAA AGAGAAACTT
TGTGCTACAC GACGACGAAG CTGCTAAATC TTCTTCTATT TTTTTAAAAT
CACTAACATT ATATTGCAAC AAGGGAAAGA AAAAAGTCTC TATTTAAATT
CTTTTTTTTA AATTTTCTTC TTTAGTTGGT GTGTTTTTGG GATGTCTTAT
TTTTAGATGG TTACACTGTT AGAACACTAT TTTCAGAATC TGAATGTAAT

-continued

```
TTGTGTAATA AAGTGTTTTC AGAGCATTAG CTGTCAGAGT GTATTTTGCC
AATTTTTGCA TATGTCCAGG GTTTTGTATA CTTTTGTAAT AATTACATAA
ACCACAGATT GAGTGAAACC TACTCAATGT CTTCAACCAA AAGAAATGTG
TTGTATTGTA TTAAAATCAA GAAGATATTT TGTTATGTAG CTGATACAAA
TTAAAAACCA GCCTAAGAGC TTACATACAT GTGTAAAATC AGGCTCTCTG
ATGATTCAAC GAGAGTGTTT GCCTGTATAT CAATCAGAAG GTAAATACTT
GAATAAAAGG TGATCATAGC TGAGAGGAAA AAAAAAAAAA AAAAA
(iv)
                                                   AG AGTGGAGCAT
CGATCAGTTA AAAAGGCTGG CATTGAGGTC CAGGAAATCA AAGCAGAGTC
TGAACACAAA GTCGAGGCAA GGTCAGGAAG AGTACTGGGA AGACTTAGAG
GAAAAGGAAG TGGAGGCTTA AACCTCGGAA ATTTCTTTGC GAGCCGTAAA
GGCTACAGTC GGAAAGGGTT TGACCGGCTC AGCACCGAGG GGAGTGACCA
GGAGAAAGAT GAGGATGACG GAAGTGAATC AGAAGAAGAA TATTCAGCAC
CTCTGCCCGC ACCTGTACCT TCCTCCTCCT GAAAACTGGG CTTTGATTTA
GTTGATGAGA TTTACCAAGA ATGCCAGGTT CCTTTCCCTT TAGCACGATT
AGAGTTTTGT GTATTTAATT GTAAACTGTA CTAGTCTGTG TGGGACTGTA
CACATTTTAT TTACTTCGTT TTGGTTTAGT TGGCTTCTGT TTCTGGTTGA
GGAGTTTCCT AAAAGTTCAT AACAGTGCCA TTGTCTTTAT CTGAACATAG
AATAGAGAAA CAGTCCTCTT CTTCCATCAC GTTACTAATT TAATGATGGA
AGCTTTGCTC ATTTACATTT TGAGACTTTT CTGTAGGTGT AAATAGCCCC
ATTCTCTGCT TGGACACAGT CTTTTCCCAA TAGCACTTCC ATTGCCAGTG
TCTTTCTTTG GTGCCTTTCC TGTTCAGCAT TCTCAGCCTG TGGCAGTAAA
GAGAAACTTT GTGCTACACG ACGACGAAGC TGCTAAATCT TCTTCTATTT
TTTTAAAATC ACTAACATTA TATTGCAACA AGGGAAAGAA AAAAGTCTCT
ATTTAAATTC TTTTTTTTAA ATTTTCTTCT TTAGTTGGTG TGTTTTTGGG
ATGTCTTATT TTTAGATGGT TACACTGTTA GAACACTATT TTCAGAATCT
GAATGTAATT TGTGTAATAA AGTGTTTTCA GAGCATTAAA AAAAAAAAAA
AAAAAAAAAA AAAAAAAAAA AAAAAAAAAA
```

The cloning of the CDNA of the present invention can be practiced according to the method known per se by the use of various tissues of horse as in the description concerning rat.

In the following, the CDNA preparation method of the present invention is described in more detail.

A tissue which forms abundantly a peptide C-terminal amidating enzyme in horse (hereinafter called "plus tissue"), for example, an atrium of horse is homogenized together with guanidyl thiocyanate to crush the cells, and RNA fraction is obtained by cecium chloride equilibration density gradient ultracentrifugation. Subsequently, by affinity chromatography having an oligo-dT-cellulose carried thereon, an RNA having a poly-A (poly-$A^+$RNA) is isolated from the above-mentioned RNA fraction.

By use of the poly-$A^+$RNA as the template, a cDNA library is obtained according to the method known in the art, preferably the method of Okayama-Berg (Mol. Cell. Biol. 2, 161, 1982). The method of Okayama-Berg is practiced as described below. That is, the poly-A portion of poly-$A^+$RNA is adsorbed onto the poly-T portion of the Okayama-Berg vector, whereby the reaction of the reverse transcriptase is carried out to synthesize a cDNA. After addition of an oligodC to the 3'-end of the cDNA with a terminal deoxynucleotidyl transferase, the vector DNA is cleaved with a restriction endonuclease HindIII. After ligation of an oligodG linker, the vector is cyclized and then the RNA portion is replaced with DNA with a DNA polymerase to obtain a cDNA containing plasmid. By the use of these plasmids, *E. coli* is transformed according to such method as the calcium chloride method (Strik, P. et. al., J. Bacteriol. 138, 1033, 1979). By selecting an ampicillin-resistant strain with an ampicillin-added flat plate medium, a plasmid-accepting microorganism is procured.

On the other hand, the above-mentioned plus tissue, namely a tissue of producing abundantly a C-terminal amidating enzyme, and a tissue of producing not so much a C-terminal amidating enzyme (hereinafter called "minus tissue"), for example, liver of horse, are prepared, and poly-$A^+$RNA is isolated according to the methods as described above from the respective cells. The 5'-OH of RNA is labelled with $^{32}$P by use of polynucleotide kinase and [$\gamma$-$^{32}$]PATP, and this is used as the probe.

Next, according to the colony hybridization method (Hanahan, D. et. al., Gene, 10, 63, 1980), a colony complimentary to the probe derived from the plus tissue but not complimentary to the minus tissue is selected from among the cDNA library as described above. Thus, a plasmid DNA is procured from the colony thus selected, and the base sequence determined according to the dideoxynucleotide method (Messing, J. Methods in Enzymology 101, 20, 1983), etc.

Whether or not these are cDNA's of the peptide C-terminal amidating enzyme can be identified by incorporating the region coding or its amino acid sequence into an expression vector system of *E. coli., Bacillul substilis*, yeast, animal culture cells, etc., producing the protein coded for by the cDNA, and then assaying the amidating enzyme activity (see e.g., PCT/JP89/00521). The cDNA obtained may be also chosen by comparison of the homology with a known C-terminal amidating enzyme CDNA. Further, a partial amino acid sequence of the enzyme purified by use of the purification method of horse C-terminal amidating enzyme described in International Published Application WO89/12096 may be also determined by a peptide sequencer, etc. and identified to be the same amino acid sequence estimated from the CDNA. Still further, antibodies with the purified enzyme as the antigen may be prepared with rabbit, rat, etc., and then identification may be made by carrying out the antigen-antibody reaction with the protein expressed in *E. coli*, etc. with the cDNA as described above.

These identification means can be also used as the cDNA cloning method utilizing those characteristics. More specifically, there may be included the method in which among the known different kinds of C-terminal amidating enzyme cDNA's, the region with high homology between those kinds is considered to be also high in the CDNA derived from horse, and the cDNA library DNA is screened as the DNA in such region as the probe; the screening method with the use of an antibody by a cDNA cloning system by use of $\lambda$gt11 phage as the probe; the screening method of cDNA library of preparing from a part of amino acid sequences of the purified enzyme a synthetic DNA (several kinds) having the codons corresponding thereto by a DNA synthesizer, etc., and preparing this as the probe by use of a plasmid, phage, etc.

The DNA sequence coding for the protein having the peptide C-terminal amidating enzyme activity of the present invention thus prepared can produce the peptide C-terminal amidating enzyme in a large amount by linking its DNA to an appropriate expression vector, thereby expressing the enzyme with *E. coli, Bacillus subtilis*, yeast, animal cells, etc. as the host.

EXAMPLES

The present invention is described in detail with reference to Examples, which is no way limit, the present invention.

Example 1

Preparation of gel for substrate affinity chromatography

An amount of 5 ml of Affigel 10 was measured into a 10 ml volume Econocolumn (produced by Biorad) filled with isopropanol. After isopropanol was washed out, the gel was washed with 50 ml of 10 mM sodium acetate buffer (pH 4.5) and then with 10 ml of 0.1 M Mops-sodium hydroxide buffer (containing 80 mM calcium chloride, pH 7.5). After the gel was transferred into a bottle of 20 ml volume, it was mixed with 10 ml of the above Mops-sodium hydroxide buffer containing 40 mg (about 100 μmol) of phenylalanyl-glycyl-phenylalanyl-glycine (Phe-Gly-Phe-Gly, produced by Sigma) dissolved therein and a shaking reaction was carried out at 4° C. for 18 hours. Then, 0.5 ml of 1 M Tris-HCl buffer (pH 8.0) was added and a shaking reaction was carried out at 4° C. for one hour to deactivate the unreacted active groups. After the gel was washed with the above Mops-sodium hydroxide buffer, then, with deionized water, it was suspended in 0.02% $NaN_3$ filled in a column and stored at 4° C. From the amount of the peptide (Phe-Gly-Phe-Gly) provided for the reaction and the peptide amount in the solution, about 10 μmol per 1 ml of gel was calculated to be bound.

Example 2

Preparation of phenylalanyl-glycyl-phenylalanyl-hydroxylglycine as substrate

Figure 1:
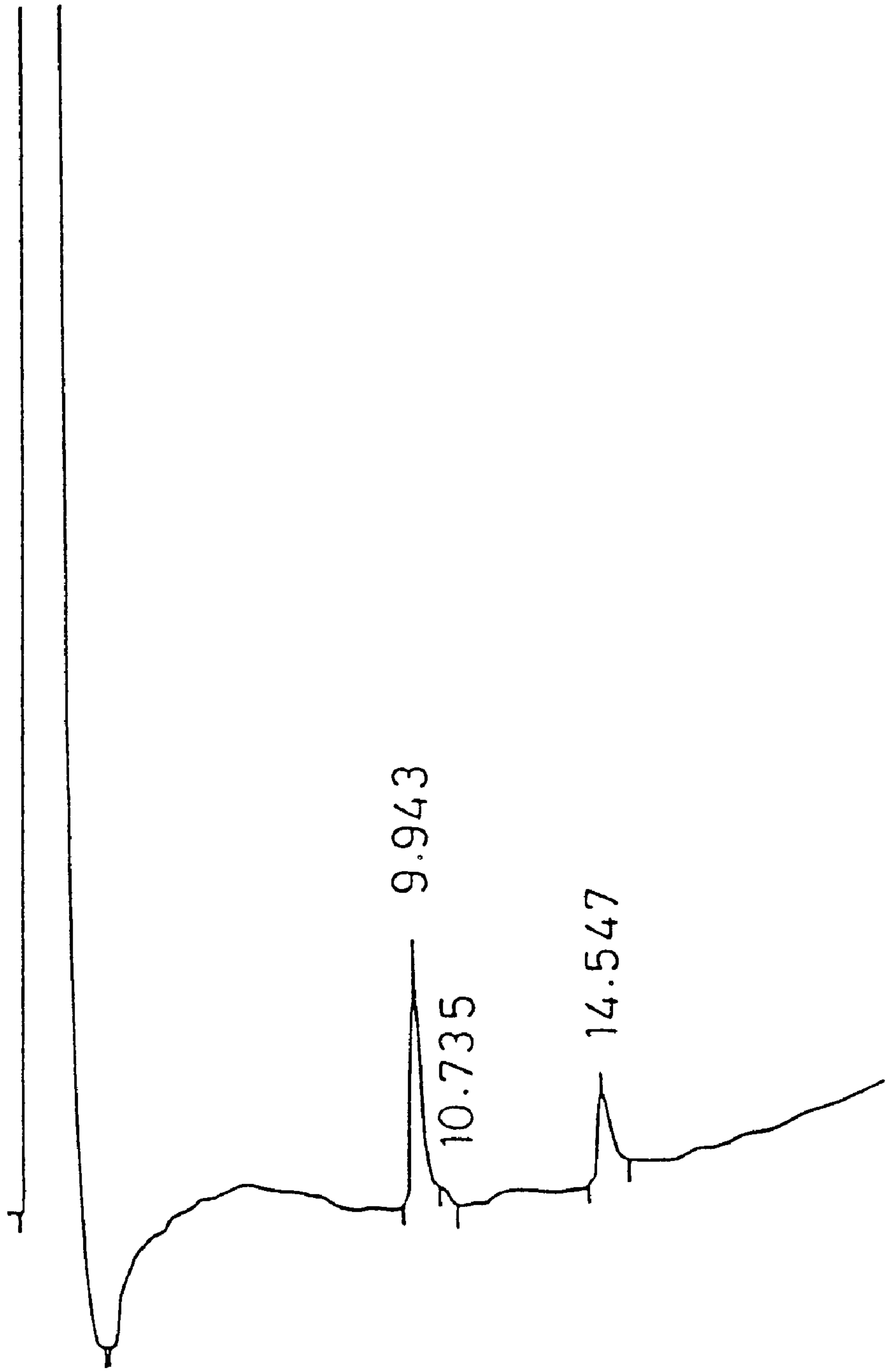
FIG. 1 is an HPLC pattern when preparing FGFhyG by using the enzyme-I of the present invention, with FGFG as the substrate.
Figure 2:
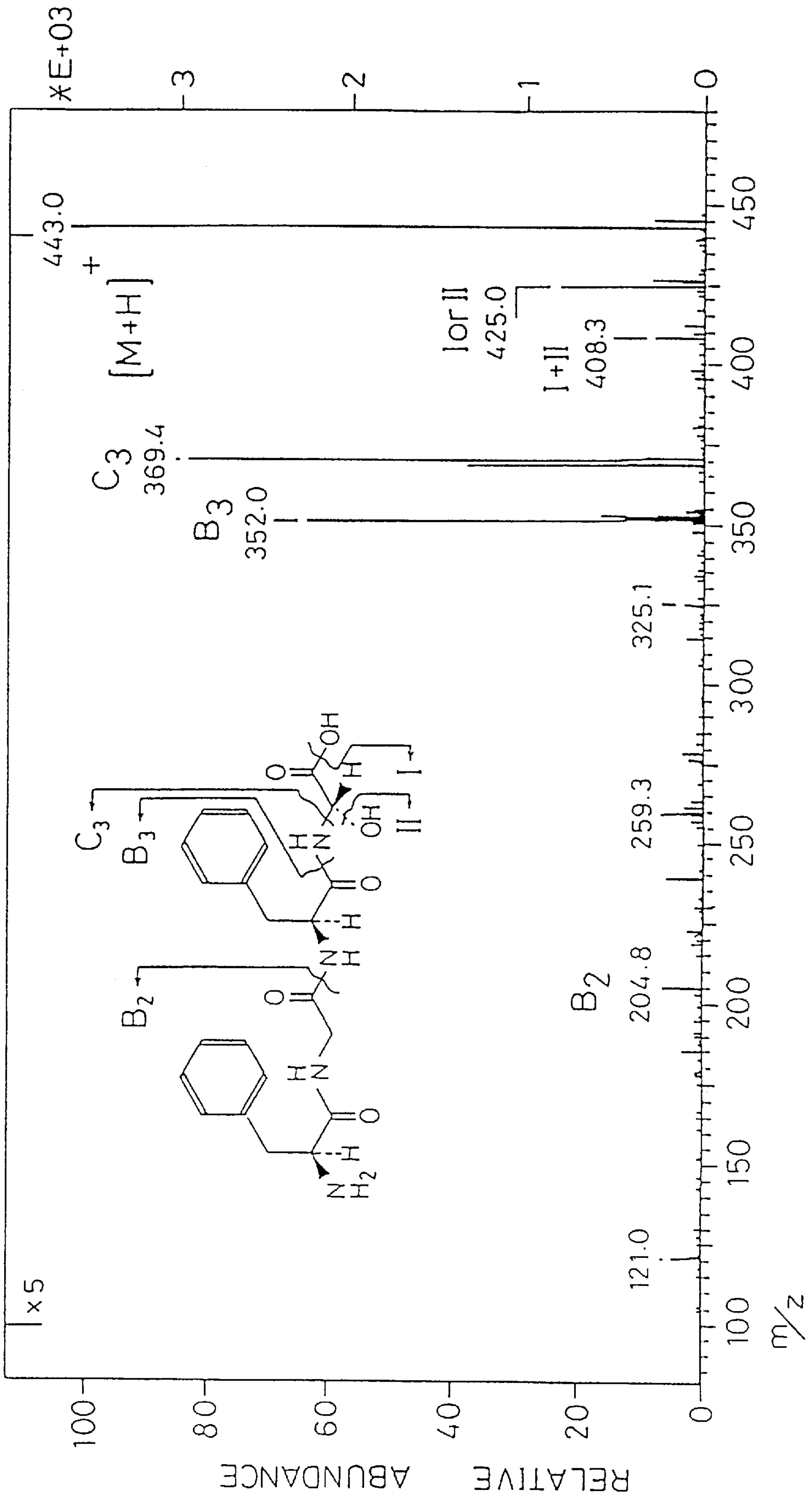
FIG. 2 shows the results of an FAB-MS spectrum analysis conducted for confirmation of the molecular structure of FGFhyG prepared.

An amount of 3 mg of phenylalanyl-glycyl-penylalanylglycine (FGFG) (produced by Sigma) was weighed, and 50 mM Hepes-KOH buffer (pH 5.5), 3 mM ascorbic acid, 10 mM potassium iodide, 0.25 mg/ml catalase, 0.25 mM cupric sulfate, 7.5% acetonitrile and 200 μl of an amidated enzyme composition derived from horse serum as described in Example 2 in International Patent Application JP89-00521 to make up the total amount to 10 ml, followed by aerobic amidation reaction at 30° C. for 20 hours. The reaction was stopped by addition of 10% formic acid, and phenylalanyl-glycyl-phenylalanyl-hydroxylglycine (FGFhyG) was separated by high performance liquid chromatography (HPLC). The column of HPLC used was Capscell Pack C18SG, 300 Å (manufactured by Shiseido). The eluting solvent used was 1 mM ammonium dicarbonate (pH 9.0) and acetonitrile, and a linear gradient of increasing acetonitrile from 0% to 40% for 30 minutes applied. The peptide was detected by the absorption at 214 nm. The results are shown in FIG. 1. The peak of phenylalanyl-glycyl-phenylalanyl-glycine at 10.7 minute was substantially extinguished after the C-terminal amidating reaction. As accompanied therewith, the peaks of the α-hydroxyglycine derivative at 9.9 minute and the amidated compound at 14.5 minute were observed. The structures of these substances were identified by FAB-MS spectrum analysis and NMR analysis. FIG. 2 shows the results of the FAB-MS spectrum in glycerine solution. The parent peak represents the molecular weight of 442, and as the result of its fragmentation, fragments of 425 and 408 m/z with one or two —OH groups existing at C-terminal being cleaved off were identified, thus indicating that it is α-hydroxylglycine adduct. The peak at 9.9 min. was separated, formed swiftly into a 10% formic acid solution, which was then lyophilized to prepare the substrate for the enzyme II of the present invention. The substrate could be similarly prepared even when the enzyme-I containing product of the present invention was used in place of the above amidating enzyme composition. As described above, the α-hydroxylglycine derivative is stable under acidic conditions, but unstable under alkaline conditions and will be decomposed into the amidated compound and glyoxylic acid irrespectively of the enzyme reaction. Therefore, the C-terminal amidation reaction initially conducted in this Example was practiced under acidic conditions. At this time, if the reaction is carried out at pH 7.5 or higher, it becomes impossible to identify the α-hydroxylglycine derivative. The known C-terminal amidating enzyme has been considered to be converted from the C-terminal glycine adduct represented by the formula (I) as described above to the C-terminal amidated compound represented by the formula (III) and glyoxylic acid, because non-enzymatic conversion under the alkaline conditions was included, and the catalytic reaction of the enzyme itself is the conversion reaction from the C-terminal glycine adduct represented by the formula (I) to the C-terminal α-hydroxylglycine adduct represented by the formula (II). Therefore, conversion of the amidating reaction under acidic conditions by the C-terminal amidating enzyme in the prior art has been generally low.

Example 3

Preparation of enzyme-I from horse serum (1) To 100 ml of a commercially available horse serum (produced by Gibco) was gradually added under stirring 100 ml of a 25% aqueous polyethylene glycol 6000 (w/v) (produced by Wako Junyaku), namely to a final concentration of 12.5%. The following operations were all conducted at 4° C. After standing for 12 hours, the mixture was centrifuged (10,000× g, 10 min.) and the resultant precipitates were dissolved in 120 ml of Hepes-potassium hydroxide buffer (pH 7.0). Further after standing for 2 hours, the insoluble substance formed was again removed by centrifugation (10,000× g, 10 min.) to obtain a supernatant containing the C-terminal amidating enzyme activity (127 ml).

Figure 3:
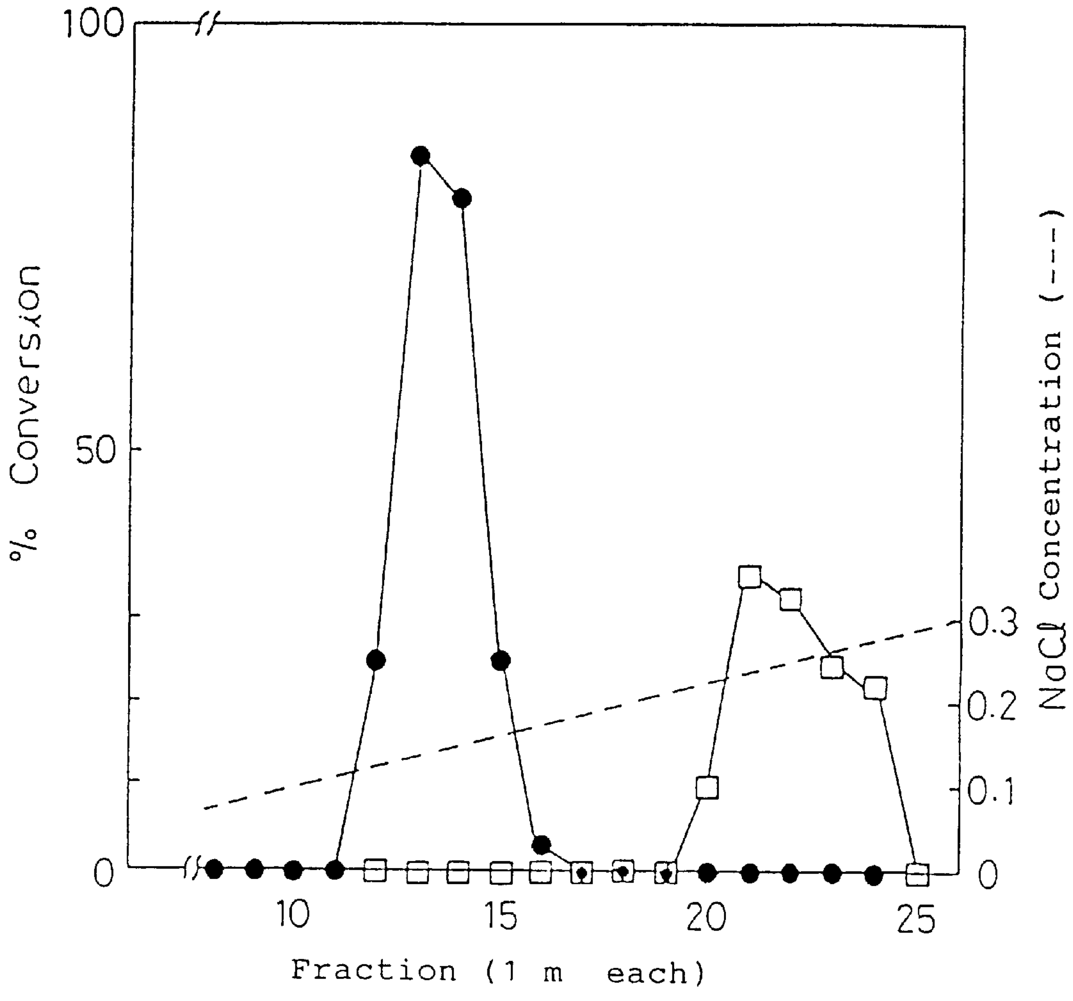
FIG. 3 is a chromatogram pattern showing a separation of the enzyme-I and the enzyme-II of the present invention according to chromatography by a Mono Q column, wherein the open square plots indicate the activity of the enzyme-II, the filled circle plots show the activity of the enzyme-I, and the broken line shows the linear concentration gradient of sodium chloride.

(2) The active fraction obtained in the above (1) was applied to a column (1.6×15 cm) filled with heparin Sepharose CL-6B (produced by Pharmacia) equilibrated with 10 mM Hepes-potassium hydroxide buffer (pH 7.0). After the nonadsorbed substances were washed out with 96 ml of the same buffer, elution was effected with 10 mM Hepes-potassium hydroxide buffer (pH 7.0) containing 0.5 M sodium chloride (flow rate 30 ml/hr). FIG. 3 shows the elution pattern. The present enzyme-I was eluted with 0.5 M sodium chloride containing buffer [fractions Nos. 14–16 were collected (100 ml)].

(3) The above fractions were subjected to gel filtration by use of Sephadex G-25 Fine (produced by Pharmacia) column chromatography (5 cmφ×23 cm). By use of 10 mM Hepes-KOH (pH 7.0) as the solvent, elution was effected at a flow rate of 2 ml/min. The proteins were detected by absorbance at 280 nm, and 100 ml of fractions containing the proteins was collected.

(4) Affigel 10-Phe-Gly-Phe-Gly gel prepared according to Example 1 in an amount of 5 ml of filled in a column (1.0×6.3 cm), and the column was equilibrated with 10 mM Hepes-potassium hydroxide buffer (pH 7.0) containing 0.1 M sodium chloride. To the column was applied the sample (18.1 ml) obtained in the above (3). To ensure that the enzyme-I was adsorbed onto the gel, the liquid passed through the column was circulated many times through the column (flow rate 20 ml/hr). After 12 hours, the circulation was stopped, and the nonadsorbed substances were washed out with 35 ml of the buffer used for equilibration, followed by elution with 8 mM Hepes-potassium hydroxide buffer (pH 7.0) containing 0.4 M sodium chloride and 20% acetonitrile (flow rate 20 ml/hr). The enzyme-I activity was recognized only in the eluted fraction (10 ml).

(5) The purified product obtained in the above (4) was subjected against to the treatment (3) as described above, then carried on Mono column (produced by Pharmacia, 0.5×5 cm) equilibrated with 10 mM hepes-potassium hydroxide buffer (pH 7.0), and an NaCl linear concentration gradient was applied in the same buffer as shown in FIG. 3, to elute the proteins. The flow rate at this time was made 0.5 ml/min.

Table 1 shows the total protein amounts, the total enzyme activities, specific activities, yields and purification folds in the respective steps of purification conducted in the above (1) to (5).

TABLE 1

Preparation of enzyme-I from horse serum

| Step | Total protein (mg) | Total activity (U) | Specific activity (U/mg) | Yield (%) | Purification fold |
|---|---|---|---|---|---|
| Serum | 7,500 | 10,500* | 1.4 | 100 | |
| (1) Polyethylene glycol 6000 Precipitation | 4,100 | 9,020 | 2.2 | 86 | 1.6 |
| (2) Heparin Sepharose CL-6B | 1,400 | 5,740 | 4.1 | 55 | 2.9 |
| (3) Sephadex G-25 | 1,100 | 3,960 | 3.6 | 38 | 2.6 |
| (4) Affigel 10-Phe-Gly-Phe-Gly | 2.0 | 800 | 400 | 8 | 290 |
| (5) Mono Q column | 0.5 | 350 | 700 | 3 | 500 |

* Probably because of the influence of the protease existing in the serum, the substrate and product were partially decomposed to give a relatively lower activity.

The activity assay was conducted by practicing the reaction according to the preparation method from FGFG to FGFhyG as described in Example 2 and quantitating FGFhyG by HPLC as described there. The enzyme activity 1 U was defined as the enzyme amount forming 1 ninole of FGFhyG at 37° C. for one hour.

A measurement of the protein amount was conducted by using the improved method of Lowry (Bensadoun et al, Anal. Biochem., 70 265, 1976), and the standard curve was prepared with bovine serum albumin (fraction V, produced by Sigma).

As shown in Table 1, the present enzyme could be purified to about 500-fold with a yield of 2%. When further purification is required, the above-described steps (3) to (5) may be repeated, or either one of those steps may be repeated.

Example 4

Preparation of enzyme-II from horse serum

Horse serum was treated in the same manner as in Example 3 except for performing the respective purification steps while monitoring the activity of the enzyme-II.

Table 2 shows the total proteins, the total enzyme activities, specific activities, yields and purification folds in the respective purification steps (1) to (5).

TABLE 2

Preparation of enzyme-II from horse serum

| Step | Total protein (mg) | Total activity (U) | Specific activity (U/mg) | Yield (%) | Purification fold |
|---|---|---|---|---|---|
| Serum | 7,500 | 2,100* | 0.28 | | |
| (1) Polyethylene glycol 6000 Precipitation | 4,000 | 5,300 | 1.3 | 250 | 4.6 |
| (2) Heparin Sepharose CL-6B | 1,500 | 3,800 | 2.5 | 180 | 9.0 |
| (3) Sephadex G-25 | 1,200 | 3,000 | 2.5 | 140 | 9.0 |
| (4) Affigel 10-Phe-Gly-Phe-Gly | 1.2 | 360 | 300 | 17 | 1070 |
| (5) Mono Q column | 0.1 | 50 | 500 | 2 | 1790 |

*Probably because of the influence of the protease existing in the serum, the substrate and product were partially decomposed to give a relatively lower activity.

Figure 4:
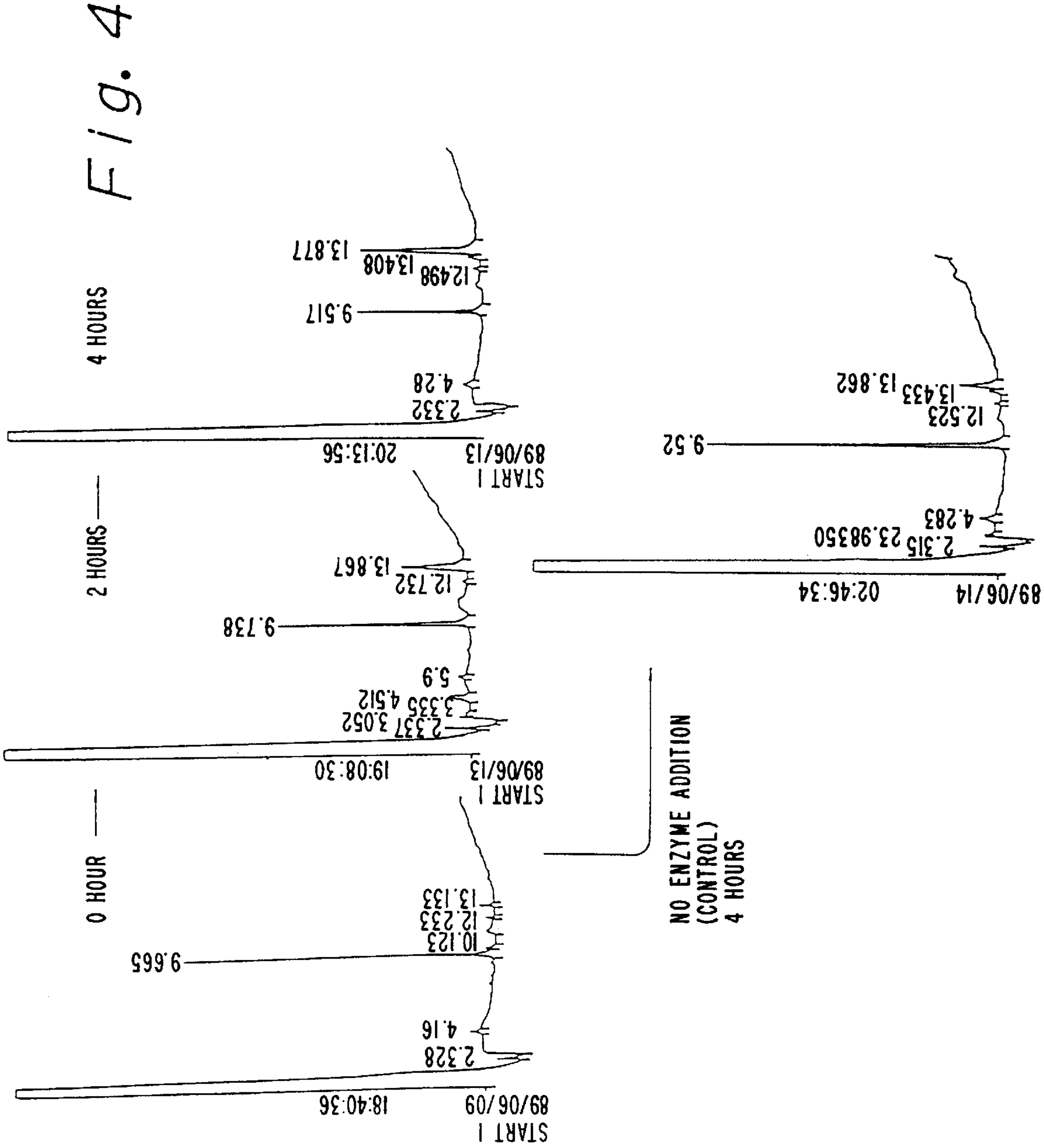
FIG. 4 shows an HPLC pattern over a lapse of time when preparing FGF-$NH_2$ by using the enzyme-II of the present invention with FGFhyG as the substrate.
Figure 7:
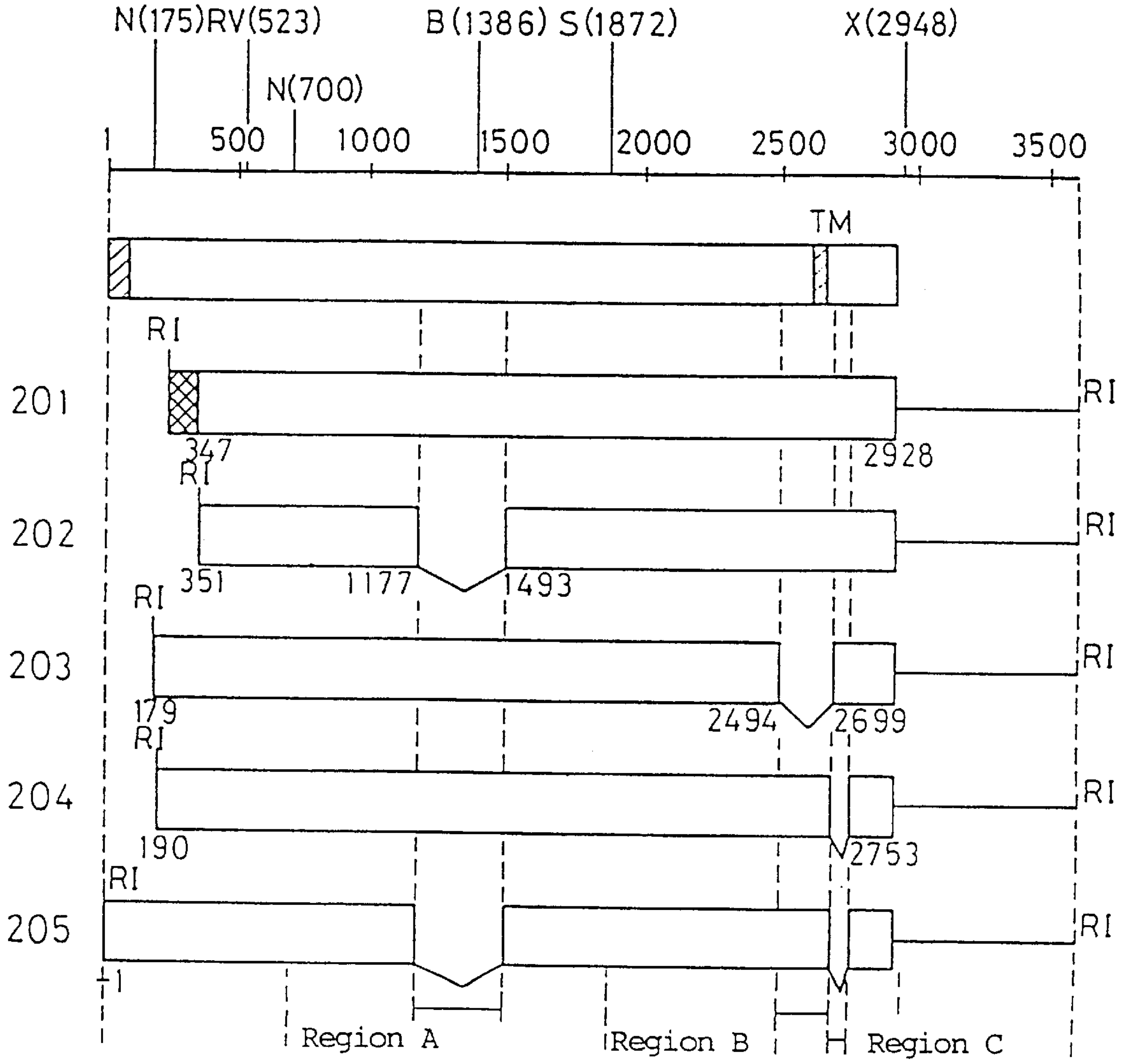
FIG. 7 schematically shows the five C-terminal amidating enzymes cloned from the rat pituitary mRNA, wherein the region coding for the enzyme estimated is shown by boxes. The numerals indicate the base numbers (bp) with the translation initiation point being made 1, TM represents the portion corresponding to the membrane-transport region, KK represents the lysine-lysine sequence, and the restriction endonucleases are shown by the following abbreviations, respectively.

Activity assay was carried out at 30° C. by dissolving the phenylalanyl-glycyl-phenylalanyl-hydroxylglycine (FGFhyG) obtained in Example 1 in 10 mM hepes-potassium hydroxide (pH 6.5) to 5 mM concentration, adding the samples at the respective steps, and making up the total amount to 100 ml. After the reaction for one hour, the reaction was stopped by addition of 10% formic acid, and the reaction product was quantitated by HPLC using the conditions of Example 2. At this time, the reaction of Control with no addition of the sample was also conducted to confirm that substantially no non-enzymatic conversion proceeded. The HPLC pattern of the reaction mixture is shown in FIG. 4 (the reaction conditions in the Figure are 37° C., pH 6.9, with the reaction time being indicated in the Figure), and the activity represented in unit (U). 1 U is defined as the enzyme amount which forms 1 nmole of FGF-$NH_2$ at 30° C. for one hour.

Measurement of the protein mass was carried out in the same manner as in Example 3.

As shown in Table 2, the present enzyme could be purified to about 1800-fold with a yield of 2%.

In the following Examples, production of said enzyme utilizing a peptide C-terminal amidating enzyme CDNA derived from rat pituitary is described, but the present invention is not limited thereby.

Example 5

Construction of expression plasmid

By use of the poly-A RNA derived from rat pituitary, 5 cDNA clones were obtained (see FIGS. 6(A)–6(H), FIG. 7, Seikagaku, 61, 842 (1989)).

The DNA fragment of 2.58 kbp (kilobase pairs) of the cDNA clone 205 cleaved by EcoRI-XmaI was inserted into an expression vector of an animal culture cell system, pSV2 vector [S. Subramani, R. Mulligan, P. Berg, Mol. Cell. Biol. I, 854 (1981)] via a synthetic linker at the HindIII-BqlII, and the plasmid was designated as SV-205. Next, the NsiI (700)—XmaI fragment of SV-205 was replaced with the respective NsiI(700)—XmaI fragments of CDNA clones 201, 202, 203, 204. These expression plasmids were called SV-201, SV-202, SV-203, SV-204. The SV-203 DNA was deleted the DNA region coding trans membrane domain. From the SV-203 plasmid DNA this obtained, an expression plasmid SV-A which expresses an enzyme by acting on a C-terminal glycine adduct according to the present invention to convert it to a C-terminal α-hydroxylglycine adduct was constructed. The DNA portion of the BamHI site [FIG. 7 (1386)] existing in the vicinity of the CDNA region coding for the KK sequence portion around the center was deleted by digestion with BamHI, XmaI [FIG. 7 X (1948)], and a synthetic linker:

5'-CATCTGAAAC-3'
3-ACTTTGGGCC-5' was inserted into the cleaved site, ligation was effected, followed by completion of the SV-A plasmid. The synthetic DNA was synthesized in conventional manner by use of a DNA synthesizer produced by ABI and purified. The synthetic DNA is constituted of the BamHI cleaved site-stop codon-XmaI cleaved site.

Next, an expression plasmid SV-B according to the present invention which expresses an enzyme for converting a C-terminal α-hydroxylglycine adduct to a C-terminal amidated compound and glyoxylic acid was constructed. The SV-203 DNA was cleaved at the KpnI site [FIG. 7, N (175)] existing immediately downstream of the region coding for the signal peptide and the BamHi site existing at the position corresponding to the vicinity of the KK site at the center, and linked in A between thereof with a synthetic DNA:

5'-GATCGTAC-3'
3'-CATGCTAG-5' to form an expression plasmid SV-B. As the result, the signal peptide region were combined with the cDNA latter part site in reading frame.

Example 6

Expression in animal culture cells

The cultured cell COS-7 was grown in a synthetic medium (DMEM) containing a 10% fetal bovine serum and transformed by use of the expression plasmid of Example 5 according to the known method (see C. Chen and H. Okayama, Mol. Cell. Biol. 7, 2745 (1987)). In the transformation, 20 μg of the expression plasmid was employed per $5\times10^5$ cells. After cultivation under the conditions of 3% carbon dioxide, 35° C. for 24 hours, the cells were washed twice with 10 ml of a DMEM medium containing 0.2% bovine serum albumin (BSA), and then further cultured in 10 ml of the DMEM medium containing 0.2% BSA under the conditions of 5% carbon dioxide and 37° C. for 48 hours.

Example 7

C-terminal amidating enzyme activity produced by the recombinant cells

The cell culture broth expressed in Example 6 was separated by centrifugation into cells and supernatant (medium).

For the supernatant, enzyme activity was assayed. Assay of the activity was carried out following basically the method by use of HPLC shown in a literature (J. Biol. Chem. 265, 9602–9605). Shortly speaking, the conversion activity of the C-terminal glycine adduct to the α-hydroxylglycine adduct was determined by permitting the reaction to proceed with the reaction composition (A) as shown below and quantitating the substrate (PheGlyPheGly) and the product (PheGlyPhehydroxyGly) after a certain time of the reaction.

Reaction composition (A):

15 μM PheGlyPheGly 5 mM $CuSO_4$

5 μl/reaction mixture 1 ml Catalase (Sigma)

100 mM MES buffer (pH 5.6)

1 mM Ascorbic acid

+ Culture supernatant (medium)

The converting activity of the α-hydroxylglycine adduct to the amidated compound and glyoxylic acid was assayed similarly by use of the following reaction composition (B).

Reaction composition (B):

15 μM PheGlyPhehydroxyGly*

100 mM MES buffer (pH 5.6)

+ Culture supernatant (medium)

* The reaction was permitted to proceed in the reaction composition (A), and prepared from the α-hydroxylglycine adduct separated by HPLC.

The assay results are shown in Table 3.

TABLE 3

| Plasmid | | Enzyme activity n mole/h/ml medium<br>Substrate<br>Product | PheGlyPheGly<br>PheGlyPhe-hydroxyGly | PheGlyPhehydroxyGly<br>PheGlyPhe-$NH_2$ + Glyoxylic acid |
|---|---|---|---|---|
| SV-203 | (Signal sequence + N-terminal domain + C-terminal domain; present invention) | | 2.5 | 4.2 |
| SVa | (Signal sequence + N-terminal domain; present invention) | | 2.8 | <2 |
| SVb | (Signal sequence + C-terminal domain; present invention) | | 0.4 | 10.8 |
| PSV2 | (Control) | | 0.3 | <2 |
| NO Plasmid | (Control) | | 0.5 | <2 |

In medium of the transformant with the SV-a plasmid, a markedly improved α-hydroxylglycine adduct producing activity was recognized, and it did not participate in the reaction with the α-hydroxylglycine adduct as the substrate. In contrast, in the strain transformed with the SV-b plasmid, no reaction occurred at all on the C-terminal glycine adduct, but only an activity of converting the α-hydroxylglycine adduct to the amidated compound was recognized. In the strain transformed with the plasmid SV-203 having substantially the whole region of the cDNA, both enzyme activities were recognized, but the respective enzyme activities were lower as compared with SV-a, SV-b.

Next, whether or not the enzyme expressed in these transformed strains is single was confirmed by gel filtration chromatography. By the use of a Sephacryl S-200 (produced by Pharmacia) column (1×95 cm), the column was equilibrated with an elution buffer 10 mM HEPES-KOH (pH 7.0), 50 mM NaCl. The elution rate was 6 ml/hour, and 1 ml fractions were collected. The results of the both enzyme activities and the protein masses assayed are shown in FIG. 8 to FIG. 10. The enzyme activities derived from SV-a (FIG. 8) and from SV-b (FIG. 9) became respectively the single peaks, and also the molecular weights assayed were found to be 36 kDa, and 54 kDA, corresponding to the molecular weights of the proteins coded for by the cDNA's possessed by the respective plasmids. However, the protein derived from SV-203 plasmid, as shown in FIG. 10, was separated into the two peaks of the activity for producing the α-hydroxylglycine adduct (□—□) by acting on the C-terminal glycine and the activity for producing the amidated compound and glyoxylic acid (○—○) by acting on the α-hydroxylglycine adduct. Besides, these molecular weights were found to be the same as those of the respective enzymes shown in FIG. 8, FIG. 9 expressed solely. This result showed that the KK sequence positioned at the central portion of the protein coding for the CDNA was cleaved by processing the culture cells. Therefore, it was shown that the two kinds of enzymes according to the present invention can be also produced by expression of the cDNA having such whole cDNA region.

Next, the synergetic effect by using the two kinds of enzymes in the present invention in the C-terminal amidating reaction was shown by use of FIG. 11 and FIG. 12. FIG. 11 and FIG. 12 show the change in conversion of amidated compound with a lapse of time when PheGlyPheGly was employed as the substrate. The enzyme samples were prepared by purifying the medium supernatants obtained by expression of SV-a, SV-b plasmids by the gel filtration as described above, and concentrating the respective active fractions. FIG. 11 shows one derived from SV-a, which shows that only the α-hydroxyl adduct is produced with no amidated compound being produced. FIG. 12 shows the case when using only the enzyme derived from SV-b (☆), and the case when using those derived from SV-a and SV-b in combination. It was shown that none of the α-hydroxyl adduct and the amidated compound were produced at all with only the enzyme derived from SV-b, while both the α-hydroxyl adduct and the amidated compound could be produced well by using the both enzymes in combination (the amounts of the enzymes added were the same). Note, the reaction efficiency is increased when they were used after 4 hours or later, and after the reaction for 9 hours, a conversion as high as 1.5-fold is obtained compared with the case of use of only the enzyme derived from SV-a shown in FIG. 11. Thus, the use of both enzymes proved to be a very effective means for carrying out the C-terminal amidating reaction.

Example 8

Preparation of Poly-$A^+$RNA from horse heart atrium (1) Preparation of whole RNA Horse heart atrium after enucleation was minced swiftly, and about 2 g thereof was placed in a 50 ml plastic tube (No. 2070, produced by Falcon) and freezed in liquid nitrogen. An amount 20 ml of guanidine thiocyanate solution (4 M guanidine thiocyanate, 25 mM sodium citrate (pH 7.0), 0.5% laurylsarcosine sodium, 0.1% Antifoam A, 0.1 M 2-mercaptoethanol) were added, and the cells were crushed by means of Polytron (Central Kagaku Boeki), followed by take-out and introduction of the crushed liquor by a 10 ml syringe (produced by Terumo Co., Ltd.) equipped with an 18 G injection needle. The sedimentation was removed by a low speed centrifugation (300× g, 5 minutes), and 7.3 ml of the supernatant was overlaid in a 3.7 ml CsTFA vessel (produced by Pharmacia, aqueous cesium trifluoroacetic acid containing 0.5 M EDTA, adjusted to a density of 1.64 g/ml) and treated by a ultra-centrifugation machine by use of a swing rotor RPS-40T (produced by Hitachi Seisakusho, SCP85H) at 33,000 rpm for 16 hours. The precipitates were washed with 3 ml of 4 M guanidine solution, then with 3 ml of 95% ethanol and thereafter dissolved in 1.5 ml CsTFA solution. To the solution were added 60 μl of 5 M NaCl Solution, 3.9 ml of ethanol, and ethanol precipitation was effected at −80° C. for 30 minutes, followed by centrifugation at 16,000× g for 15 minutes to obtain precipitates. The precipitates were washed with 70% ethanol, and then dried by a concentrator (produced by Sakuma Seisakusho, EC-57C). After dissolved in sterilized distilled solution, absorbance at 260 nm was measured to quantitate the RNA amount. According to this method, 350 μg of RNA could be obtained from about 2 g of a horse heart atrium tissue.

(2) Preparation of poly-$A^+$RNA

Preparation of a poly-A RNA from the whole RNA was carried out by use of "mRNA Purification Kit" (produced by Pharmacia) according to the accompanying protocol. Affinity chromatography was carried out twice by an oligo(dT) column to obtain 13 μg of a poly-$A^+$RNA from 350 μg of a horse heart atrium whole RNA.

Example 9

Preparation of cDNA library (1) Preparation of cDNA

By the use of "cDNA Synthesis System Plus" (RPN1256Y, produced by Amersham), cDNA synthesis was. carried out by the use of 5 μg of a horse heart atrium poly-$A^+$RNA. The synthesis procedure followed faithfully the accompanying protocol. As the primer, an oligo-dT-nucleotide was employed, and the cDNA synthesis efficiency was calculated from the radio-activity according to a synthetic system containing [α-$^{32}$P]-dCTP. As the result, the reverse transcription efficiency was found to be about 20%, and the second strand synthesis efficiency 90% or higher.

(2) Preparation of cDNA library

By use of "cDNA Cloning System λgt10, version 2.0" (RPN 1257, produced by Amersham) for linking to the phage DNA, and "Gigapack;Gold" (produced by Stratagene) for packaging into the phage, a cDNA. library was prepared from the synthetic cDNA according to the accompanying protocols of these.

(3) Infection of *E. coli*

As the host microorganism, *E. coli* Y1089 (ATCC37196) was employed, and the competent cells were prepared as described below. Single colony cells were inoculated into 5 ml of an NZY medium (0.5% NaCl, 1% NZ amine, type A (Wako Junyaku), 0.5% yeast extract (DIFCO), 0.2% magnesium sulfate, pH 7.5) added with 0.2% maltose, and shaking cultivation was carried out at 37° C. overnight. An amount of 100 μl of the culture broth was transplated into 5 ml of the same fresh medium, and after culturing at 37° C. to $OD_{660}$=0.5, the microorganisms were collected by centrifugation. The competent cells were prepared by suspending the cells in 1 ml of a 10 mM magnesium sulfate solution.

To 0.2 ml of the competent cell suspension was added 0.1 ml of the phage solution prepared in (2), and the mixture was mixed with 3 ml of top agarose (NZY medium containing 0.7% type I-LowEEO-agarose (produced by Sigma)) maintained at a temperature of 56° C., followed by casting into the upper part of an NZY agar plate (30 ml of NZY medium containing 1.5% Bactoagar (produced by DIFCO) added to the 1005 Plate produced by Falcon). After solidifcation of top agarose, stationary cultivation was carried out at 37° C. overnight. By identifying the plaques, the phage-infected cells were identified.

According to the method as described above, a horse heart atrium cDNA library containing 2.0×$10^7$ independent phage.

Example 10

Isolation of C-terminal amidating enzyme cDNA (1) Preparation of DNA probe

A peptide C-terminal amidating enzyme cDNA derived from rat has been already isolated, and its sequence reported (D. A. Soffer et. al., Proc. Natl. Acad. Sci. USA, 86, 735–739 (1989), Kato et. al., Seikagaku, 61, 842 (1989)). The present inventors considered that there is homology to some extent between the rat cDNA and the C-terminal amidating enzyme cDNA derived from horse, procured a part of the rat cDNA and progressed isolation of the horse cDNA with the use of this as the probe. The rat CDNA was gifted from Tohoku University, School of Medicine (Kato et. al., Seikagaku, 61, 842 (1989)), which was digested with restriction endonucleases EcoRI and HincII as well as Nsi I and Sph I, whereby the DNA fragments shown in FIGS. 14(A)–14(C) and FIGS. 15(A)–15(F) were respectively isolated, followed by $^{32}$P labelling by Multiprime DNA Labelling Kit (produced by Amersham) to provide a probe.

(2) Plaque hybridization

According to the method shown in the infection of *E. coli* in Example 9 (3) about 500,000 plaques were formed per one sheet of a plate of 15 cm in diameter (No. 1058, produced by FALCON). The cultivation for plaque formation was carried out at 37° C. for 4 hours. After the plate was left to stand at 4° C. for 2 hours, a nitrocellulose filter (BA85, produced by Schleicher & Schuell) was adhered to have the phage DNA migrated to the filter, and then the DNA was denatured in an alkaline solution (0.5 M caustic soda, 1.5 M sodium chloride). After neutralization with a neutralizing solution (1.5 M sodium chloride, 0.5 M Tris-HCl buffer, pH 7.0), the mixture was rinsed with a 2 XSSC solution (0.3 M sodium chloride, 30 mm sodium citrate buffer pH 7.0), and after air drying heated at 80° C. for 2 hours under a reduced pressure, followed by fixing of the DNA onto the filter.

For the nitrocellulose filter having the phage DNA fixed thereon, plaque hybridization was effected by use of the probe prepared in (1). The filter was placed in Lappybag (produced by Iwatani), and 30 ml of a prehybridization liquor (0.75 M sodium chloride, 50 mM sodium phosphate buffer, pH 7.4, 5 mM EDTA, 0.05% Ficoll, 0.05% polyvinyl pyrrolidone, 0.05% bovine serum albumin (fraction V, produced by Sigma), 0.1% SDS, 0.2 mg/ml salmon sperm DNA) was added, followed by sealing of the bag by a sealer and heating at 65° C. for 4 hours. The prehybridization liquor was discarded, and 30 ml of a hybridization solution (0.75 M sodium chloride, 50 mM sodium phosphate buffer, pH 7.4, 5 mM EDTA, 0.02% Ficoll, 0.02% polyvinyl pyrrolidone, 0.02% bovine serum albumin, 0.1% SDS, 0.1 mg/ml salmon sperm DNA having about 1.0×$10^7$ cpm of the radioactivities was added, and after sealing, hybridization was effected at 65° C. for 15 hours. The filter was washed twice with 250 ml of a washing solution (0.3 mM sodium chloride, 20 mM sodium phosphate buffer, pH 7.4, 2 mM EDTA, 0.1% SDS) and further twice with 250 ml of a washing solution (30 mM sodium chloride, 2 mM sodium phosphate buffer pH 7.4, 0.2 mM EDTA, 0.1% SDS) and dried on air. The positive clone was detected by autoradiography by an X-ray film (Fuji, HR-H) under the exposure conditions at −80° C. overnight.

For the two probes employed, 2,000,000 plaques were respectively screened, and about 1000 positive clones were obtained. The phage DNA was recovered from the positive plaques, and again *E. coli* was effected therewith according to the method as described above, and plaque hybridization practiced again, which operations were repeated until the plaque became single. Ordinarily, single plaques can be obtained by repeating the operations twice.

Example 11

Determination of cDNA base sequence

According to the method described on pages 371–372 in Molecular Cloning A Laboratory Manual (T. Maniatis, E. F. Fritsch, J. Sambrook, editors, Cold Spring Harbor Laboratory, 1982), DNA was separated and purified from the phage cloned. The DNA was digested with a restriction enconuclease EcoRI (produced by Takara Shuzo), and the cDNA insertion DNA fragment was separated from the phage DNA according to 1.5% Agarose gel electrophoresis. The cDNA fragment was extracted from the gel, and incorporated at the EcoRI site of the *E. coli* plasmid pUC 119 (produced by Takara Shuzo) by the ligation reaction. When the EcoRI site exists in the cDNA fragment, the cDNA fragment was obtained by partial digestion of the phage DNA with EcoRI. After the plasmid was amplified, the cDNA fragment was subcloned with M13 phages mp 18, mp 19 (produced by Takara Shuzo), to obtain a single-stranded DNA following conventional procedures. By the use of Sequenase (trade name, produced by Toyo Boseki K.K.) following the instructions thereof, the DNA base sequence was determined. The base sequence of single-stranded DNA was determined for about 400 bases, and for the DNA fragment with a length exceeding that length, the sequence was determined by subcloning by the use of an appropriate restriction endonuclease. For the CDNA fragment, the base sequences of both chains of the double-strand were determined.

FIGS. 13(A)–13(P) show the horse C-terminal amidating enzyme cDNA base sequence determined (this base sequence shows the longest cDNA as the result of many analyses of CDNA) and the amino acid sequence (one letter representation) expected from the base sequence. Also, cDNA's in which one or both of the portions shown by [ ] in the Figure were deficient could be confirmed. These cDNA's are considered to be derived from mRNA's by different mRNA splicing methods.

INDUSTRIAL APPLICABILITY

The present invention can be utilized for producing a peptide C-terminal amidation compound from the corresponding peptide C-terminal glycine adduct. Such a peptide C-terminal amidation compound includes valuable physiologically active substances.

What is claimed is:

1. A method of preparing an enzyme, wherein said enzyme participates in C-terminal amidation and acts on a peptide C-terminal glycine adduct represented by the following formula (I):

(I)

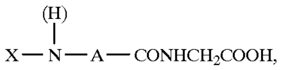

wherein A represents a residue other than α-amino group or imino group and α-carboxylic group derived from naturally occurring α-amino acid, X represents a hydrogen atom or a residue of an amino acid derivative which is bonded to the N atom through carbonyl group, to form a peptide C-terminal α-hydroxylglycine adduct represented by the following formula (II):

(II)

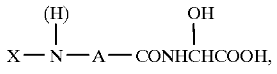

wherein A and X have the meanings as above, but said enzyme does not convert the peptide C-terminal α-hydroxyglycine adduct (II) to a C-terminal amidated peptide represented by the following formula (III):

(III)

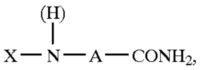

wherein A and X have the meanings as above, wherein said method of preparing said enzyme comprises culturing host cells transformed with a plasmid comprising a cDNA which encodes said enzyme and which is capable of expressing said enzyme, and collecting said enzyme from the culture.

2. The method of claim 1, wherein said cDNA is derived from a mammal.

3. The method of claim 1, wherein said cDNA is that in which the membrane spanning region has been excised.

4. The method of claim 2, wherein the mammal is rat or horse.

5. The method of claim 1, wherein said collection is carried out by substrate affinity chromatography using as a ligand the peptide C-terminal glycine adduct represented by said formula (I).

* * * * *

SEQUENCE LISTING (1) GENERAL INFORMATION:

(iii) NUMBER OF SEQUENCES: 21

(2) INFORMATION FOR SEQ ID NO:1:

(i) SEQUENCE CHARACTERISTICS:
(A) LENGTH: 631 base pairs
(B) TYPE: nucleic acid
(C) STRANDEDNESS: single
(D) TOPOLOGY: linear (ii) MOLECULE TYPE: DNA (genomic)

(vi) ORIGINAL SOURCE:
(A) ORGANISM: rat (xi) SEQUENCE DESCRIPTION: SEQ ID NO:1:

```
ATGGCCGGAC GCGCCCGCAG CGGTCTGCTA CTGCTGCTGC TCGCCCTGCA TCGCCCTGCA    60

GACCAGCTGC CTGGCCTTCA GAAGCCCACT TTCTGTCTTT AAGAGGTTTA AAGAAACTAC   120

CCAGATCATT TTCCAATGAA TGCCTTGGTA CCATTGGACC AGTCACCCCT CTTGATGCAT   180

CAGATTTTGC GCTGGATATT CGCATGCCTG GGGTTACACC TAAAGAGTCT GACACATACT   240

TCTGCATGTC CATGCGTCTG CCTGTGGATG AGGAAGCTTC GTGATTGACT TCAAGCCTCG   300

TGCCAGCATG GATACTGTCC ACCATATGCT GCTGTTTGGA TGCAATATGC CCTCGTCCAC   360

TGGAAGTTAC TGGTTTTGTG ATGAAGGAAC CTGTAAACAG ATAAAGCCAA TATTCTATAT   420

GCCTGGGCAA GGAATGCTCC CCCACCCGGC TCCCGAAAGG TGTTGGATTC AGATTGGAGG   480

AGAAACTGGA AGCAAATACT TCGTCCTTCA AGTTCACTAT GGCGATATCA GTGCTTTTCG   540

AGATAATCAC AAAGACTGCT CTGGCGTGTC CGTACATCTC ACACGTGTGC CCCAGCCTTT   600

AATTGCGGGC ATGTACCTTA TGATGTCTGT T                                  631
```

(2) INFORMATION FOR SEQ ID NO:2:

(i) SEQUENCE CHARACTERISTICS:
(A) LENGTH: 6638 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Horse -continued

```
    (ix) FEATURE:
          (A) NAME/KEY: CDS
          (B) LOCATION: 11..3070

    (xi) SEQUENCE DESCRIPTION: SEQ ID NO:2:

CGGCGTGGAC ATG GCT GGC CTT CGT AGC CTG CTA GTT CTC CTC CTT GTT        49
           Met Ala Gly Leu Arg Ser Leu Leu Val Leu Leu Leu Val
             1               5                  10

TTT CAG AGC AGC TGT TTG GGT TTC AGA AGC CCA CTT TCT GTC TTT AAG       97
Phe Gln Ser Ser Cys Leu Gly Phe Arg Ser Pro Leu Ser Val Phe Lys
     15                  20                  25

AGG TTT AAA GAA ACT ACC AGA CCA TTT TCC AAT GAA TGT CTT GGT ACC      145
Arg Phe Lys Glu Thr Thr Arg Pro Phe Ser Asn Glu Cys Leu Gly Thr
 30                  35                  40                  45

ACC AGA CCA GTC ATT CCT ATT GAT TCA TCA GAT TTT GCA TTG GAT ATT      193
Thr Arg Pro Val Ile Pro Ile Asp Ser Ser Asp Phe Ala Leu Asp Ile
                 50                  55                  60

CGC ATG CCT GGA GTC ACA CCT AAA CAG TCT GAT ACA TAC TTC TGC ATG      241
Arg Met Pro Gly Val Thr Pro Lys Gln Ser Asp Thr Tyr Phe Cys Met
             65                  70                  75

TCG ATG CGT TTG CCA ATG GAT GAG GAA ACC TTC GTG ATT GAC TTC AAA      289
Ser Met Arg Leu Pro Met Asp Glu Glu Thr Phe Val Ile Asp Phe Lys
         80                  85                  90

CCT CGT GCC AGC ATG GAT ACT GTC CAT CAT ATG TTA CTT TTT GGT TGC      337
Pro Arg Ala Ser Met Asp Thr Val His His Met Leu Leu Phe Gly Cys
     95                 100                 105

AAT ATG CCC TCA TCC ACT GGA AGT TAC TGG TTT TGT GAT GAA GGC GTC      385
Asn Met Pro Ser Ser Thr Gly Ser Tyr Trp Phe Cys Asp Glu Gly Val
110                 115                 120                 125

TGT ACA GAC AAA GCC AAT ATT CTC TAT GCC TGG GCA AGA AAT GCT CCC      433
Cys Thr Asp Lys Ala Asn Ile Leu Tyr Ala Trp Ala Arg Asn Ala Pro
                130                 135                 140

CCC ACC AGA CTC CCC AAA GGT GTT GGA TTC AGA GTT GGA GGA GAG ACT      481
Pro Thr Arg Leu Pro Lys Gly Val Gly Phe Arg Val Gly Gly Glu Thr
            145                 150                 155

GGA AGT AAA TAC TTC GTA CTA CAA GTA CAC TAT GGG GAT ATT AGT GCT      529
Gly Ser Lys Tyr Phe Val Leu Gln Val His Tyr Gly Asp Ile Ser Ala
        160                 165                 170

TTT AGA GAT AAT CAC AAG GAC TGT TCT GGT GTG TCC TTA CAC CTC ACA      577
Phe Arg Asp Asn His Lys Asp Cys Ser Gly Val Ser Leu His Leu Thr
    175                 180                 185

CGC CTG CCA CAG CCT TTA ATT GCT GGC ATG TAC CTT ATG ATG GCT CTT      625
Arg Leu Pro Gln Pro Leu Ile Ala Gly Met Tyr Leu Met Met Ala Leu
190                 195                 200                 205

GAC ACT GTT ATA CCA GCA GGA GAG AAA GTG GTG AAT TCT GAC CTT TCA      673
Asp Thr Val Ile Pro Ala Gly Glu Lys Val Val Asn Ser Asp Leu Ser
                210                 215                 220

TGC CAT TAT AAA AAG TAC CCA ATG CAT GTC TTT GCC TAT AGA GTT CAC      721
Cys His Tyr Lys Lys Tyr Pro Met His Val Phe Ala Tyr Arg Val His
            225                 230                 235

ACT CAC CAT TTA GGT AAG GTA GTA AGT GGC TAC AGA GTA AGA AAT GGA      769
Thr His His Leu Gly Lys Val Val Ser Gly Tyr Arg Val Arg Asn Gly
        240                 245                 250

CAG TGG ACA CTG ATT GGA CGT CAG AGC CCC CAG CTG CCA CAG GCT TTC      817
Gln Trp Thr Leu Ile Gly Arg Gln Ser Pro Gln Leu Pro Gln Ala Phe
    255                 260                 265

TAC CCT GTG GAA CAC CCA GTA GAT GTC AGT TTT GGT GAC ATA CTG GCA      865
Tyr Pro Val Glu His Pro Val Asp Val Ser Phe Gly Asp Ile Leu Ala
270                 275                 280                 285
```

-continued

```
GCA AGA TGT GTG TTC ACT GGT GAA GGA AGG ACA GAA GCC ACG CAC ATT      913
Ala Arg Cys Val Phe Thr Gly Glu Gly Arg Thr Glu Ala Thr His Ile
                290                 295                 300

GGT GGC ACA TCT AGT GAT GAA ATG TGC AAC TTA TAC ATT ATG TAT TAC      961
Gly Gly Thr Ser Ser Asp Glu Met Cys Asn Leu Tyr Ile Met Tyr Tyr
            305                 310                 315

ATG GAA GCC AAG CAC GCA GTT TCT TTC ATG ACC TGT ACC CAG AAT GTA     1009
Met Glu Ala Lys His Ala Val Ser Phe Met Thr Cys Thr Gln Asn Val
        320                 325                 330

GCT CCA GAA ATG TTC AGA ACC ATC CCC CCA GAG GCC AAT ATT CCA ATT     1057
Ala Pro Glu Met Phe Arg Thr Ile Pro Pro Glu Ala Asn Ile Pro Ile
    335                 340                 345

CCT GTG AAG TCC GAC ATG GTT ATG ATG CAT GGA CAT CAC AAA GAA ACA     1105
Pro Val Lys Ser Asp Met Val Met Met His Gly His His Lys Glu Thr
350                 355                 360                 365

GAG AAC AAA GAT AAG ACT TCA CTA CAA CAG CCA AAA CAA GAA GAA GAA     1153
Glu Asn Lys Asp Lys Thr Ser Leu Gln Gln Pro Lys Gln Glu Glu Glu
                370                 375                 380

GTG TTA GAA CAG GGT GAT TTC TAT TCA CTG CTT TCC AAG CTG CTA GGA     1201
Val Leu Glu Gln Gly Asp Phe Tyr Ser Leu Leu Ser Lys Leu Leu Gly
            385                 390                 395

GAA AGG GAA GAT GTT GTT CAT GTG CAT AAA TAT AAC CCT ACA GAA AAG     1249
Glu Arg Glu Asp Val Val His Val His Lys Tyr Asn Pro Thr Glu Lys
        400                 405                 410

GCA GAA TCA GAG TCA GAC CTG GTA GCT GAG ATT GCA AAT GTA GTC CAA     1297
Ala Glu Ser Glu Ser Asp Leu Val Ala Glu Ile Ala Asn Val Val Gln
    415                 420                 425

AAG AAG GAT CTC GGT CGA TCT GAT GCC AGA GAG AGT GCA GAG CAT GAG     1345
Lys Lys Asp Leu Gly Arg Ser Asp Ala Arg Glu Ser Ala Glu His Glu
430                 435                 440                 445

GAC AGG GGC AAT GCT ATT CTT GTC AGA GAC AGA ATT CAC AAA TTC CAC     1393
Asp Arg Gly Asn Ala Ile Leu Val Arg Asp Arg Ile His Lys Phe His
                450                 455                 460

AGA CTA GAA TCT ACT TTG AGG CCA ACA GAG AGC AGA GTT ATC TCA GTA     1441
Arg Leu Glu Ser Thr Leu Arg Pro Thr Glu Ser Arg Val Ile Ser Val
            465                 470                 475

CCG CAG CCC CTA CCT GGT GAA GGC ACC TGG GAA CCA GAA CAC ACA GGA     1489
Pro Gln Pro Leu Pro Gly Glu Gly Thr Trp Glu Pro Glu His Thr Gly
        480                 485                 490

GAT TTC CAT GTA GAA GAG GCA CTG GAT TGG CCT GGA GTA TAC TTG TTA     1537
Asp Phe His Val Glu Glu Ala Leu Asp Trp Pro Gly Val Tyr Leu Leu
    495                 500                 505

CCA GGC CAG GTT TCT GGG GTA GCT CTG GAC CTT CAG AAT AAC CTG GTG     1585
Pro Gly Gln Val Ser Gly Val Ala Leu Asp Leu Gln Asn Asn Leu Val
510                 515                 520                 525

ATT TTC CAC AGA GGT GAC CAT GTC TGG GAT GGA AAC TCT TTT GAC AGC     1633
Ile Phe His Arg Gly Asp His Val Trp Asp Gly Asn Ser Phe Asp Ser
                530                 535                 540

AAG TTT GTG TAC CAG CAA AGA GGA CTC GGG CCA ATT GAA GAA GAT ACT     1681
Lys Phe Val Tyr Gln Gln Arg Gly Leu Gly Pro Ile Glu Glu Asp Thr
            545                 550                 555

ATT CTT GTC ATA GAT CCA AAT AAT GCT GCA GTC CTC CAG TCC AGT GGA     1729
Ile Leu Val Ile Asp Pro Asn Asn Ala Ala Val Leu Gln Ser Ser Gly
        560                 565                 570

AAA AAT CTG TTT TAC TTG CCA CAT GGC TTG AGC ATA GAC AAA GAT GGA     1777
Lys Asn Leu Phe Tyr Leu Pro His Gly Leu Ser Ile Asp Lys Asp Gly
    575                 580                 585

AAT TAT TGG GTC ACA GAC GTG GCT CTC CAT CAG GTG TTC AAA CTG GAT     1825
Asn Tyr Trp Val Thr Asp Val Ala Leu His Gln Val Phe Lys Leu Asp
590                 595                 600                 605
```

-continued

```
CCA AAC AGT AAA GAA GGC CCT CTG TTG ATC CTG GGA AGA AGC ATG CAA      1873
Pro Asn Ser Lys Glu Gly Pro Leu Leu Ile Leu Gly Arg Ser Met Gln
                610                 615                 620

CCA GGC AGT GAC CAG AAT CAC TTC TGT CAA CCC ACC GAT GTG GCT GTA      1921
Pro Gly Ser Asp Gln Asn His Phe Cys Gln Pro Thr Asp Val Ala Val
            625                 630                 635

GAT CCA AAC ACT GGG ACC ATC TTT GTA TCA GAT GGT TAC TGC AAC AGT      1969
Asp Pro Asn Thr Gly Thr Ile Phe Val Ser Asp Gly Tyr Cys Asn Ser
        640                 645                 650

CGG ATC GTG CAG TTT TCA CCA ACT GGA AGG TTC ATC ACA CAG TGG GGA      2017
Arg Ile Val Gln Phe Ser Pro Thr Gly Arg Phe Ile Thr Gln Trp Gly
    655                 660                 665

GAA GAG TCT TCT GAG AGC AAT CCT AAA CCA GGC CAG TTC AGG GTT CCT      2065
Glu Glu Ser Ser Glu Ser Asn Pro Lys Pro Gly Gln Phe Arg Val Pro
670                 675                 680                 685

CAC AGC TTG GCC CTT GTG CCT CAT TTG GGC CAA TTA TGT GTG GCC GAC      2113
His Ser Leu Ala Leu Val Pro His Leu Gly Gln Leu Cys Val Ala Asp
                690                 695                 700

CGG GAA AAT GGT CGG ATC CAG TGT TTT AAA ACT GAC ACC AAA GAA TTT      2161
Arg Glu Asn Gly Arg Ile Gln Cys Phe Lys Thr Asp Thr Lys Glu Phe
            705                 710                 715

GTG CGA GAG ATT AAG CAT GCA TCA TTT GGA AGA AAT GTA TTT GCA ATT      2209
Val Arg Glu Ile Lys His Ala Ser Phe Gly Arg Asn Val Phe Ala Ile
        720                 725                 730

TCG TAT ATA CCA GGT TTG CTC TTT GCC GTA AAT GGG AAG CCT TAC TTT      2257
Ser Tyr Ile Pro Gly Leu Leu Phe Ala Val Asn Gly Lys Pro Tyr Phe
    735                 740                 745

GGG GAC CAA AAA CCA GTA CAA GGA TTT GTG ATG AAC TTT TCC AGT GGG      2305
Gly Asp Gln Lys Pro Val Gln Gly Phe Val Met Asn Phe Ser Ser Gly
750                 755                 760                 765

GAA ATT ATA GAT GTC TTC AAG CCA GTG CGC AAG CAC TTT GAC ATG CCT      2353
Glu Ile Ile Asp Val Phe Lys Pro Val Arg Lys His Phe Asp Met Pro
                770                 775                 780

CAT GAC ATT ACT GCA TCT GAA GAC GGG ACT GTG TAT GTT GGA GAT GCT      2401
His Asp Ile Thr Ala Ser Glu Asp Gly Thr Val Tyr Val Gly Asp Ala
            785                 790                 795

CAC ACC AAC ACC GTG TGG AAG TTC ACT TCG ACT GAA ACA GCC CAG GTC      2449
His Thr Asn Thr Val Trp Lys Phe Thr Ser Thr Glu Thr Ala Gln Val
        800                 805                 810

TGG TTC CCG GGT GTG GAC CTA CAT CAC TCG TCA GTG GCC ATG CTG TGG      2497
Trp Phe Pro Gly Val Asp Leu His His Ser Ser Val Ala Met Leu Trp
    815                 820                 825

TGG CAG CTC ACA TAC AAA AAG AGG AAG ATT GAC AAC AGA TGT TAT CTC      2545
Trp Gln Leu Thr Tyr Lys Lys Arg Lys Ile Asp Asn Arg Cys Tyr Leu
830                 835                 840                 845

AGG GCC AAT CTT CCT CAG CAA ATG AAA AAA AAA AGA GTG GAG CAT CGA      2593
Arg Ala Asn Leu Pro Gln Gln Met Lys Lys Lys Arg Val Glu His Arg
                850                 855                 860

TCA GTT AAA AAG GCT GGC ATT GAG GTC CAG GAA ATC AAA GAA TCC GAG      2641
Ser Val Lys Lys Ala Gly Ile Glu Val Gln Glu Ile Lys Glu Ser Glu
            865                 870                 875

GCA GTT GTT GAA ACC AAA ATG GAG AAC AAA CCC GCC TCC TCA GAA TTG      2689
Ala Val Val Glu Thr Lys Met Glu Asn Lys Pro Ala Ser Ser Glu Leu
        880                 885                 890

CAG AAG ATG CAA GAG AAA CAG AAA CTG ATC AAA GAG CCA GGC TCG GGA      2737
Gln Lys Met Gln Glu Lys Gln Lys Leu Ile Lys Glu Pro Gly Ser Gly
    895                 900                 905

GTG CCC GTT GTT CTC ATT ACA ACC CTT CTG GTT ATT CCG GTG GTT GTC      2785
Val Pro Val Val Leu Ile Thr Thr Leu Leu Val Ile Pro Val Val Val
```

-continued

```
910                915                920                925

CTG CTG GCC ATT GCC ATA TTT ATT CGG TGG AAA AAA TCA AGG GCC TTT     2833
Leu Leu Ala Ile Ala Ile Phe Ile Arg Trp Lys Lys Ser Arg Ala Phe
                930                935                940

GGA GAG TCT GAA CAC AAA GTC GAG GCA AGT TCA GGA AGA GTA CTG GGA     2881
Gly Glu Ser Glu His Lys Val Glu Ala Ser Ser Gly Arg Val Leu Gly
            945                950                955

AGA CTT AGA GGA AAA GGA AGT GGA GGC TTA AAC CTC GGA AAT TTC TTT     2929
Arg Leu Arg Gly Lys Gly Ser Gly Gly Leu Asn Leu Gly Asn Phe Phe
        960                965                970

GCG AGC CGT AAA GGC TAC AGT CGG AAA GGG TTT GAC CGG CTC AGC ACC     2977
Ala Ser Arg Lys Gly Tyr Ser Arg Lys Gly Phe Asp Arg Leu Ser Thr
    975                980                985

GAG GGG AGT GAC CAG GAG AAA GAT GAG GAT GAC GGA AGT GAA TCA GAA     3025
Glu Gly Ser Asp Gln Glu Lys Asp Glu Asp Asp Gly Ser Glu Ser Glu
990                995                1000               1005

GAA GAA TAT TCA GCA CCT CTG CCC GCA CCT GTA CCT TCC TCC TCC         3070
Glu Glu Tyr Ser Ala Pro Leu Pro Ala Pro Val Pro Ser Ser Ser
                1010               1015               1020

TGAAAACTGG GCTTTGATTT AGTTGATGAG ATTTACCAAG AATGCCAGGT TCCTTTCCCT   3130

TTAGCACGAT TAGAGTTTTG TGTATTTAAT TGTAAACTGT ACTAGTCTGT GTGGGACTGT   3190

ACACATTTTA TTTACTTCGT TTTGGTTTAG TTGGCTTCTG TTTCTGGTTG AGGAGTTTCC   3250

TAAAAGTTCA TAACAGTGCC ATTGTCTTTA TCTGAACATA GAATAGAGAA ACAGTCCTCT   3310

TCTTCCATCA CGTTACTAAT TTAATGATGG AAGCTTTGCT CATTTACATT TTGAGACTTT   3370

TCTGTAGGTG TAAATAGCCC CATTCTCTGC TTGGACACAG TCTTTTCCCA ATAGCACTTC   3430

CATTGCCAGT GTCTTTCTTT GGTGCCTTTC CTGTTCAGCA TTCTCAGCCT GTGGCAGTAA   3490

AGAGAAACTT TGTGCTACAC GACGACGAAG CTGCTAAATC TTCTTCTATT TTTTTAAAAT   3550

CACTAACATT ATATTGCAAC AAGGGAAAGA AAAAAGTCTC TATTTAAATT CTTTTTTTTA   3610

AATTTTCTTC TTTAGTTGGT GTGTTTTTGG GATGTCTTAT TTTTAGATGG TTACACTGTT   3670

AGAACACTAT TTTCAGAATC TGAATGTAAT TTGTGTAATA AAGTGTTTTC AGAGCATTAG   3730

CTGTCAGAGT GTATTTTGCC AATTTTTGCA TATGTCCAGG GTTTTGTATA CTTTTGTAAT   3790

AATTACATAA ACCACAGATT GAGTGAAACC TACTCAATGT CTTCAACCAA AAGAAATGTG   3850

TTGTATTGTA TTAAAATCAA GAAGATATTT TGTTATGTAG CTGATACAAA TTAAAAACCA   3910

GCCTAAGAGC TTACATACAT GTGTAAAATC AGGCTCTCTG ATGATTCAAC GAGAGTGTTT   3970

GCCTGTATAT CAATCAGAAG GTAAATATCT GAATAAAAGG TGATCATAGC TGAGAGGAAA   4030

AAAAAAAAAA GAGTGGAGCA TCGATCAGTT AAAAAGGCTG GCATTGAGGT CCAGGAAATC   4090

AAAGAATCCG AGGCAGTTGT TGAAACCAAA ATGGAGAACA AACCCGCCTC CTCAGAATTG   4150

CAGAAGATGC AAGAGAAACA GAAACTGATC AAAGAGCCAG GCTCGGGAGT GCCCGTTGTT   4210

CTCATTACAA CCCTTCTGGT TATTCCGGTG GTTGTCCTGC TGGCCATTGC CATATTTATT   4270

CGGTGGAAAA AATCAAGGGC CTTTGGAGAG TCTGAACACA AAGTCGAGGC AAGTTCAGGA   4330

AGAGTACTGG GAAGACTTAG AGGAAAAGGA AGTGGAGGCT TAAACCTCGG AAATTTCTTT   4390

GCGAGCCGTA AAGGCTACAG TCGGAAAGGG TTTGACCGGC TCAGCACCGA GGGGAGTGAC   4450

CAGGAGAAAG ATGAGGATGA CGGAAGTGAA TCAGAAGAAG AATATTCAGC ACCTCTGCCC   4510

GCACCTGTAC CTTCCTCCTC CTGAAAACTG GGCTTTGATT TAGTTGATGA GATTTACCAA   4570

GAATGCCAGG TTCCTTTCCC TTTAGCACGA TTAGAGTTTT GTGTATTTAA TTGTAAACTG   4630

TACTAGTCTG TGTGGGACTG TACACATTTT ATTTACTTCG TTTTGGTTTA GTTGGCTTCT   4690
```

-continued

```
GTTTCTGGTT GAGGAGTTTC CTAAAAGTTC ATAACAGTGC CATTGTCTTT ATCTGAACAT   4750

AGAATAGAGA AACAGTCCTC TTCTTCCATC ACGTTACTAA TTTAATGATG GAAGCTTTGC   4810

TCATTTACAT TTTGAGACTT TTCTGTAGGT GTAAATAGCC CCATTCTCTG CTTGGACACA   4870

GTCTTTTCCC AATAGCACTT CCATTGCCAG TGTCTTTCTT TGGTGCCTTT CCTGTTCAGC   4930

ATTCTCAGCC TGTGGCAGTA AAGAGAAACT TTGTGCTACA CGACGACGAA GCTGCTAAAT   4990

CTTCTTCTAT TTTTTTAAAA TCACTAACAT TATATTGCAA CAAGGGAAAG AAAAAAGTCT   5050

CTATTTAAAT TCTTTTTTTT AAATTTTCTT CTTTAGTTGG TGTGTTTTTG GGATGTCTTA   5110

TTTTTAGATG GTTACACTGT TAGAACACTA TTTTCAGAAT CTGAATGTAA TTTGTGTAAT   5170

AAAGTGTTTT CAGAGCATTA AAAAAAAAAA AAAAAAAAAA AAAAAAAAAA AAAAAAAAAA   5230

AAACAGCCCA GGTCTGGTTC CCGGGTGTGG ACCTACATCA CTCGTCAGTG GCCATGCTGT   5290

GGTGGCAGCT CACATACAAA AAGAGGAAGA TTGACAACAG ATGTTATCTC AGGGCCAATC   5350

TTCCTCAGCA AATGAAAAAA AAAAGAGTGG AGCATCGATC AGTTAAAAAG GCTGGCATTG   5410

AGGTCCAGGA AATCAAAGCA GAGTCTGAAC ACAAAGTCGA GGCAAGTTCA GGAAGAGTAC   5470

TGGGAAGACT TAGAGGAAAA GGAAGTGGAG GCTTAAACCT CGGAAATTTC TTTGCGAGCC   5530

GTAAAGGCTA CAGTCGGAAA GGGTTTGACC GGCTCAGCAC CGAGGGGAGT GACCAGGAGA   5590

AAGATGAGGA TGACGGAAGT GAATCAGAAG AACAATATTC AGCACCTCTG CCCGCACCTG   5650

TACCTTCCTC CTCCTGAAAA CTGGGCTTTG ATTTAGTTGA TGAGATTTAC CAAGAATGCC   5710

AGGTTCCTTT CCCTTTAGCA CGATTAGAGT TTTGTGTATT TAATTGTAAA CTGTACTAGT   5770

CTGTGTGGGA CTGTACACAT TTTATTTACT TCGTTTTGGT TTAGTTGGCT TCTGTTTCTG   5830

GTTGAGGAGT TTCCTAAAAG TTCATAACAG TGCCATTGTC TTTATCTGAA CATAGAATAG   5890

AGAAACAGTC CTCTTCTTCC ATCACGTTAC TAATTTAATG ATGGAAGCTT TGCTCATTTA   5950

CATTTTGAGA CTTTTCTGTA GGTGTAAATA GCCCCATTCT CTGCTTGGAC ACAGTCTTTT   6010

CCCAATAGCA CTTCCATTGC CAGTGTCTTT CTTTGGTGCC TTTCCTGTTC AGCATTCTCA   6070

GCCTGTGGCA GTAAAGAGAA ACTTTGTGCT ACACGACGAC GAAGCTGCTA AATCTTCTTC   6130

TATTTTTTTA AAATCACTAA CATTATATTG CAACAAGGGA AAGAAAAAAG TCTCTATTTA   6190

AATTCTTTTT TTTAAATTTT CTTCTTTAGT TGGTGTGTTT TTGGGATGTC TTATTTTTAG   6250

ATGGTTACAC TGTTAGAACA CTATTTTCAG AATCTGAATG TAATTTGTGT AATAAAGTGT   6310

TTTCAGAGCA TTAGCTGTCA GAGTGTATTT TGCCAATTTT TGCATATGTC CAGGGTTTTG   6370

TATACTTTTG TAATAATTAC ATAAACCACA GATTGAGTGA AACCTACTCA ATGTCTTCAA   6430

CCAAAAGAAA TGTGTTGTAT TGTATTAAAA TCAAGAAGAT ATTTTGTTAT GTAGCTGATA   6490

CAAATTAAAA ACCAGCCTAA GAGCTTACAT ACATGTGTAA AATCAGGCTC TCTGATGATT   6550

CAACGAGAGT GTTTGCCTGT ATATCAATCA GAAGGTAAAT ACTTGAATAA AAGGTGATCA   6610

TAGCTGAGAG GAAAAAAAAA AAAAAAAA                                      6638
```

(2) INFORMATION FOR SEQ ID NO:3:

(i) SEQUENCE CHARACTERISTICS:
(A) LENGTH: 1020 amino acids
(B) TYPE: amino acid
(D) TOPOLOGY: linear (ii) MOLECULE TYPE: protein (xi) SEQUENCE DESCRIPTION: SEQ ID NO:3:

-continued

```
Met Ala Gly Leu Arg Ser Leu Leu Val Leu Leu Leu Val Phe Gln Ser
  1               5                  10                  15

Ser Cys Leu Gly Phe Arg Ser Pro Leu Ser Val Phe Lys Arg Phe Lys
             20                  25                  30

Glu Thr Thr Arg Pro Phe Ser Asn Glu Cys Leu Gly Thr Thr Arg Pro
         35                  40                  45

Val Ile Pro Ile Asp Ser Ser Asp Phe Ala Leu Asp Ile Arg Met Pro
     50                  55                  60

Gly Val Thr Pro Lys Gln Ser Asp Thr Tyr Phe Cys Met Ser Met Arg
 65                  70                  75                  80

Leu Pro Met Asp Glu Glu Thr Phe Val Ile Asp Phe Lys Pro Arg Ala
                 85                  90                  95

Ser Met Asp Thr Val His His Met Leu Leu Phe Gly Cys Asn Met Pro
            100                 105                 110

Ser Ser Thr Gly Ser Tyr Trp Phe Cys Asp Glu Gly Val Cys Thr Asp
        115                 120                 125

Lys Ala Asn Ile Leu Tyr Ala Trp Ala Arg Asn Ala Pro Pro Thr Arg
    130                 135                 140

Leu Pro Lys Gly Val Gly Phe Arg Val Gly Gly Glu Thr Gly Ser Lys
145                 150                 155                 160

Tyr Phe Val Leu Gln Val His Tyr Gly Asp Ile Ser Ala Phe Arg Asp
                165                 170                 175

Asn His Lys Asp Cys Ser Gly Val Ser Leu His Leu Thr Arg Leu Pro
            180                 185                 190

Gln Pro Leu Ile Ala Gly Met Tyr Leu Met Met Ala Leu Asp Thr Val
        195                 200                 205

Ile Pro Ala Gly Glu Lys Val Val Asn Ser Asp Leu Ser Cys His Tyr
    210                 215                 220

Lys Lys Tyr Pro Met His Val Phe Ala Tyr Arg Val His Thr His His
225                 230                 235                 240

Leu Gly Lys Val Val Ser Gly Tyr Arg Val Arg Asn Gly Gln Trp Thr
                245                 250                 255

Leu Ile Gly Arg Gln Ser Pro Gln Leu Pro Gln Ala Phe Tyr Pro Val
            260                 265                 270

Glu His Pro Val Asp Val Ser Phe Gly Asp Ile Leu Ala Ala Arg Cys
        275                 280                 285

Val Phe Thr Gly Glu Gly Arg Thr Glu Ala Thr His Ile Gly Gly Thr
    290                 295                 300

Ser Ser Asp Glu Met Cys Asn Leu Tyr Ile Met Tyr Tyr Met Glu Ala
305                 310                 315                 320

Lys His Ala Val Ser Phe Met Thr Cys Thr Gln Asn Val Ala Pro Glu
                325                 330                 335

Met Phe Arg Thr Ile Pro Pro Glu Ala Asn Ile Pro Ile Pro Val Lys
            340                 345                 350

Ser Asp Met Val Met Met His Gly His His Lys Glu Thr Glu Asn Lys
        355                 360                 365

Asp Lys Thr Ser Leu Gln Gln Pro Lys Gln Glu Glu Glu Val Leu Glu
    370                 375                 380

Gln Gly Asp Phe Tyr Ser Leu Leu Ser Lys Leu Leu Gly Glu Arg Glu
385                 390                 395                 400

Asp Val Val His Val His Lys Tyr Asn Pro Thr Glu Lys Ala Glu Ser
                405                 410                 415

Glu Ser Asp Leu Val Ala Glu Ile Ala Asn Val Val Gln Lys Lys Asp
```

-continued

```
            420                 425                 430

Leu Gly Arg Ser Asp Ala Arg Glu Ser Ala Glu His Glu Asp Arg Gly
        435                 440                 445

Asn Ala Ile Leu Val Arg Asp Arg Ile His Lys Phe His Arg Leu Glu
    450                 455                 460

Ser Thr Leu Arg Pro Thr Glu Ser Arg Val Ile Ser Val Pro Gln Pro
465                 470                 475                 480

Leu Pro Gly Glu Gly Thr Trp Glu Pro Glu His Thr Gly Asp Phe His
                485                 490                 495

Val Glu Glu Ala Leu Asp Trp Pro Gly Val Tyr Leu Leu Pro Gly Gln
            500                 505                 510

Val Ser Gly Val Ala Leu Asp Leu Gln Asn Asn Leu Val Ile Phe His
        515                 520                 525

Arg Gly Asp His Val Trp Asp Gly Asn Ser Phe Asp Ser Lys Phe Val
    530                 535                 540

Tyr Gln Gln Arg Gly Leu Gly Pro Ile Glu Glu Asp Thr Ile Leu Val
545                 550                 555                 560

Ile Asp Pro Asn Asn Ala Ala Val Leu Gln Ser Ser Gly Lys Asn Leu
                565                 570                 575

Phe Tyr Leu Pro His Gly Leu Ser Ile Asp Lys Asp Gly Asn Tyr Trp
            580                 585                 590

Val Thr Asp Val Ala Leu His Gln Val Phe Lys Leu Asp Pro Asn Ser
        595                 600                 605

Lys Glu Gly Pro Leu Leu Ile Leu Gly Arg Ser Met Gln Pro Gly Ser
    610                 615                 620

Asp Gln Asn His Phe Cys Gln Pro Thr Asp Val Ala Val Asp Pro Asn
625                 630                 635                 640

Thr Gly Thr Ile Phe Val Ser Asp Gly Tyr Cys Asn Ser Arg Ile Val
                645                 650                 655

Gln Phe Ser Pro Thr Gly Arg Phe Ile Thr Gln Trp Gly Glu Glu Ser
            660                 665                 670

Ser Glu Ser Asn Pro Lys Pro Gly Gln Phe Arg Val Pro His Ser Leu
        675                 680                 685

Ala Leu Val Pro His Leu Gly Gln Leu Cys Val Ala Asp Arg Glu Asn
    690                 695                 700

Gly Arg Ile Gln Cys Phe Lys Thr Asp Thr Lys Glu Phe Val Arg Glu
705                 710                 715                 720

Ile Lys His Ala Ser Phe Gly Arg Asn Val Phe Ala Ile Ser Tyr Ile
                725                 730                 735

Pro Gly Leu Leu Phe Ala Val Asn Gly Lys Pro Tyr Phe Gly Asp Gln
            740                 745                 750

Lys Pro Val Gln Gly Phe Val Met Asn Phe Ser Ser Gly Glu Ile Ile
        755                 760                 765

Asp Val Phe Lys Pro Val Arg Lys His Phe Asp Met Pro His Asp Ile
    770                 775                 780

Thr Ala Ser Glu Asp Gly Thr Val Tyr Val Gly Asp Ala His Thr Asn
785                 790                 795                 800

Thr Val Trp Lys Phe Thr Ser Thr Glu Thr Ala Gln Val Trp Phe Pro
                805                 810                 815

Gly Val Asp Leu His His Ser Ser Val Ala Met Leu Trp Trp Gln Leu
            820                 825                 830

Thr Tyr Lys Lys Arg Lys Ile Asp Asn Arg Cys Tyr Leu Arg Ala Asn
        835                 840                 845
```

-continued

```
Leu Pro Gln Gln Met Lys Lys Lys Arg Val Glu His Arg Ser Val Lys
    850                 855                 860

Lys Ala Gly Ile Glu Val Gln Glu Ile Lys Glu Ser Glu Ala Val Val
865                 870                 875                 880

Glu Thr Lys Met Glu Asn Lys Pro Ala Ser Ser Glu Leu Gln Lys Met
                885                 890                 895

Gln Glu Lys Gln Lys Leu Ile Lys Glu Pro Gly Ser Gly Val Pro Val
            900                 905                 910

Val Leu Ile Thr Thr Leu Leu Val Ile Pro Val Val Val Leu Leu Ala
        915                 920                 925

Ile Ala Ile Phe Ile Arg Trp Lys Lys Ser Arg Ala Phe Gly Glu Ser
    930                 935                 940

Glu His Lys Val Glu Ala Ser Ser Gly Arg Val Leu Gly Arg Leu Arg
945                 950                 955                 960

Gly Lys Gly Ser Gly Gly Leu Asn Leu Gly Asn Phe Phe Ala Ser Arg
                965                 970                 975

Lys Gly Tyr Ser Arg Lys Gly Phe Asp Arg Leu Ser Thr Glu Gly Ser
            980                 985                 990

Asp Gln Glu Lys Asp Glu Asp Asp Gly Ser Glu Ser Glu Glu Glu Tyr
        995                 1000                1005

Ser Ala Pro Leu Pro Ala Pro Val Pro Ser Ser Ser
    1010                1015                1020
```

(2) INFORMATION FOR SEQ ID NO:4:

(i) SEQUENCE CHARACTERISTICS:
(A) LENGTH: 4 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:4:

```
Phe Gly Phe Gly
1
```

(2) INFORMATION FOR SEQ ID NO:5:

(i) SEQUENCE CHARACTERISTICS:
(A) LENGTH: 5 amino acids
(B) TYPE: amino acid
(C) STRANDEDNESS: single
(D) TOPOLOGY: linear (ii) MOLECULE TYPE: peptide (ix) FEATURE:
(A) NAME/KEY: Modified-site
(B) LOCATION: 1
(D) OTHER INFORMATION: /note= “”D-tyr“”

(xi) SEQUENCE DESCRIPTION: SEQ ID NO:5:

```
Tyr Leu Asn Gly Arg
1               5
```

(2) INFORMATION FOR SEQ ID NO:6:

(i) SEQUENCE CHARACTERISTICS:
(A) LENGTH: 5 amino acids
(B) TYPE: amino acid
(C) STRANDEDNESS: single
(D) TOPOLOGY: linear -continued (ii) MOLECULE TYPE: peptide (xi) SEQUENCE DESCRIPTION: SEQ ID NO:6:

```
Phe Gly Leu Met Gly
1               5
```

(2) INFORMATION FOR SEQ ID NO:7:

(i) SEQUENCE CHARACTERISTICS:
(A) LENGTH: 4 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:7:

```
Lys Ala Phe Gly
1
```

(2) INFORMATION FOR SEQ ID NO:8:

(i) SEQUENCE CHARACTERISTICS:
(A) LENGTH: 4 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:8:

```
Gly Leu Met Gly
1
```

(2) INFORMATION FOR SEQ ID NO:9:

(i) SEQUENCE CHARACTERISTICS:
(A) LENGTH: 4 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:9:

```
Asp Arg Phe Gly
1
```

(2) INFORMATION FOR SEQ ID NO:10:

(i) SEQUENCE CHARACTERISTICS:
(A) LENGTH: 3226 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Rat (ix) FEATURE:
(A) NAME/KEY: CDS
(B) LOCATION: 2..831

(xi) SEQUENCE DESCRIPTION: SEQ ID NO:10:

```
C ATG GCC GGA CGC GCC CGC AGC GGT CTG CTA CTG CTG CTG CTG GGG         46
  Met Ala Gly Arg Ala Arg Ser Gly Leu Leu Leu Leu Leu Leu Gly
    1               5                  10                  15
```

-continued

```
CTG CTC GCC CTG CAG AGC AGC TGC CTG GCC TTC AGA AGC CCA CTT TCT       94
Leu Leu Ala Leu Gln Ser Ser Cys Leu Ala Phe Arg Ser Pro Leu Ser
                20                  25                  30

GTC TTT AAG AGG TTT AAA GAA ACT ACC AGA TCA TTT TCC AAT GAA TGC      142
Val Phe Lys Arg Phe Lys Glu Thr Thr Arg Ser Phe Ser Asn Glu Cys
            35                  40                  45

CTT GGT ACC ATT GGA CCA GTC ACC CCT CTT GAT GCA TCA GAT TTT GCG      190
Leu Gly Thr Ile Gly Pro Val Thr Pro Leu Asp Ala Ser Asp Phe Ala
        50                  55                  60

CTG GAT ATT CGC ATG CCT GGG GTT ACA CCT AAA GAG TCT GAC ACA TAC      238
Leu Asp Ile Arg Met Pro Gly Val Thr Pro Lys Glu Ser Asp Thr Tyr
    65                  70                  75

TTC TGC ATG TCC ATG CGT CTG CCT GTG GAT GAG GAA GCC TTC GTG ATT      286
Phe Cys Met Ser Met Arg Leu Pro Val Asp Glu Glu Ala Phe Val Ile
 80                  85                  90                  95

GAC TTC AAG CCT CGT GCC AGC ATG GAT ACT GTC CAC CAT ATG CTG CTG      334
Asp Phe Lys Pro Arg Ala Ser Met Asp Thr Val His His Met Leu Leu
                100                 105                 110

TTT GGA TGC AAT ATG CCC TCG TCC ACT GGA AGT TAC TGG TTT TGT GAT      382
Phe Gly Cys Asn Met Pro Ser Ser Thr Gly Ser Tyr Trp Phe Cys Asp
            115                 120                 125

GAA GGA ACC TGT ACA GAT AAA GCC AAT ATT CTA TAT GCC TGG GCA AGG      430
Glu Gly Thr Cys Thr Asp Lys Ala Asn Ile Leu Tyr Ala Trp Ala Arg
        130                 135                 140

AAT GCT CCC CCC ACC CGG CTC CCG AAA GGT GTT GGA TTC AGA GTT GGA      478
Asn Ala Pro Pro Thr Arg Leu Pro Lys Gly Val Gly Phe Arg Val Gly
    145                 150                 155

GGA GAA ACT GGA AGC AAA TAC TTC GTC CTT CAA GTT CAC TAT GGC GAT      526
Gly Glu Thr Gly Ser Lys Tyr Phe Val Leu Gln Val His Tyr Gly Asp
160                 165                 170                 175

ATC AGT GCT TTT CGA GAT AAT CAC AAA GAC TGC TCT GGC GTG TCC GTA      574
Ile Ser Ala Phe Arg Asp Asn His Lys Asp Cys Ser Gly Val Ser Val
                180                 185                 190

CAT CTC ACA CGT GTG CCC CAG CCT TTA ATT GCG GGC ATG TAC CTT ATG      622
His Leu Thr Arg Val Pro Gln Pro Leu Ile Ala Gly Met Tyr Leu Met
            195                 200                 205

ATG TCT GTT GAC ACT GTC ATA CCA CCA GGA GAG AAA GTA GTG AAT GCT      670
Met Ser Val Asp Thr Val Ile Pro Pro Gly Glu Lys Val Val Asn Ala
        210                 215                 220

GAC ATT TCG TGC CAA TAC AAA ATG TAT CCA ATG CAT GTG TTT GCC TAC      718
Asp Ile Ser Cys Gln Tyr Lys Met Tyr Pro Met His Val Phe Ala Tyr
    225                 230                 235

AGA GTC CAC ACT CAC CAT TTA GGT AAG GTG GTG AGC GGA TAC AGA GTA      766
Arg Val His Thr His His Leu Gly Lys Val Val Ser Gly Tyr Arg Val
240                 245                 250                 255

AGA AAC GGA CAG TGG ACA CTG ATT GGA CGC CAG AAC CCC CAG CTG CCA      814
Arg Asn Gly Gln Trp Thr Leu Ile Gly Arg Gln Asn Pro Gln Leu Pro
                260                 265                 270

CAG GCT TTC TAC CCT GT GGAACACCCC GTTGATGTTA CTTTTGGTGA              861
Gln Ala Phe Tyr Pro
            275

TATACTGGCA GCCAGATGTG TGTTCACTGG TGAAGGGAGG ACAGAGGCCA CCCACATCGG    921

CGGCACTTCT AGTGACGAAA TGTGTAACCT GTACATCATG TATTACATGG AAGCCAAATA    981

TGCACTTTCC TTCATGACCT GTACAAAGAA CGTGGCTCCA GATATGTTCA GAACTATCCC   1041

AGCAGAGGCC AATATCCCAA TTCCTGTCAA ACCGGACATG GTTATGATGC ACGGGCATCA   1101

CAAAGAAGCA GAAAACAAAG AAAAGAGTGC TTTAATGCAG CAGCCAAAAC AGGGAGAGGA   1161
```

-continued

```
AGAAGTATTA GAGCAGGAAT TTCCATGTGG AAGAAGAACT GGACTGGCCT GGAGTGTACT   1221
TGTTACCAGG CCAGGTTTCT GGGGTGGCCC TGGATTCTAA GAATAACCTG TGATTTTCCA   1281
CAGAGGTGAC CATGTTTGGG ATGGAAACTC TTTTGACAGC AAGTTTGTTT ACCAGCAAAG   1341
AGGTCTTGGG CCAATTGAAG AAGACACCAT CCTGGTCATT GACCCAAATA ATGCTGAAAT   1401
CCTCCAGTCC AGTGGCAAGA ACCTGTTTTA TTTACCACAC GGCTTGAGCA TAGATACAGA   1461
TGGAAATTAT TGGGTCACAG ATGTGGCTCT CCACCAGGTG TTCAAATTGG ACCCGCATAG   1521
CAAAGAAGGC CCTCTCTTAA TTCTGGGAAG GAGCATGCAA CCTGGGAGTG ACCAAAATCA   1581
TTTCTGCCAG CCCACCGATG TGGCTGTGGA GCCCAGTACT GGAGCTGTCT TCGTGTCAGA   1641
CGGTTACTGT AACAGTCGGA TTGTGCAGTT TTCACCAAGC GGAAAGTTCG TCACCCAGTG   1701
GGGAGAAGAG TCCTCTGGAA GCAGTCCTAG GCCAGGCCAG TTCAGTGTTC CTCAGAGTTT   1761
GGCCCTTGTG CCTCATTTGG ACCAGTTGTG TGTGGCAGAC AGGGAAAATG GCCGAATCCA   1821
ATGCTTCAAA ACTGACACCA AAGAATTTGT GAGAGAGATT AAGCACGCAT CATTTGGAAG   1881
GAATGTCTTT GCCATTTCAT ATATACCAGG TTTCCTCTTT GCCGTAAACG GGAAGCCTTA   1941
CTTTGGAGAC CAAGAGCCCG TGCAAGGATT TGTGATGAAC TTTTCCAGTG GGGAAATTAT   2001
AGACGTCTTC AAGCCAGTAC GCAAGCACTT CGACATGCCT CATGATATTG TGGCTTCTGA   2061
AGATGGGACT GTGTACATTG GAGACGCACA CACAAACACC GTGTGGAAGT TCACCCTGAC   2121
TGAAAAAATG GAGCATCGGT CAGTTAAAAA GGCTGGCATT GAAGTCCAGG AAATCAAAGA   2181
AGCCGAGGCA GTTGTTGAAC CCAAAGTGGA GAACAAACCC ACCTCCTCAG AATTGCAGAA   2241
GATGCAAGAG AAACAGAAAC TGAGCACAGA GCCCGGCTCG GGAGTGTCCG TGGTTCTCAT   2301
TACAACCCTT CTGGTTATTC CTGTGCTGGT CCTGCTGGCC ATTGTCATGT TTATTCGGTG   2361
GAAAAAATCA AGGGCCTTTG GAGGAAAGGG AAGCGGCGGC TTAAATCTGG GAAATTTCTT   2421
TGCAAGTCGA AAAGGCTACA GCAGAAAAGG GTTTGACCGA GTGAGCACAG AGGGGAGTGA   2481
CCAAGAGAAA GATGAGGACG ACGGAAGTGA GTCTGAAGAG GAGTACTCGG CCCCGCTGCC   2541
CAAGCCTGCA CCTTCCTCCT GAGCTCCAGC CTTCGCCCGG GTAGCTGGAC TGAGGTTTAC   2601
CAGGATGCCC AGACTCCTTC CCCTTTAGCG CGTGTAAAGT TCTGTGCATT TGATTGTAAA   2661
CTGTACTCGT CAGTGTGGGA CTGTACACAC CTTATTTACT TCATTTGGCT CCGTTGGCTT   2721
CTGTTTTCTA GGTGAGGAGT TCCCCACCAG TTCACTCCAG TGCCATTGTC TTTATATGAA   2781
CTTAGCGTAG AGAAGCCGCC CTCCTCTTCC AAGGTAGCGC TCCAACCCCC GAGGGAAGTT   2841
TAGCTCATTC ACATTTGGAG ACGTTTTAGT TGGTGGATGT AAATAGCCCT ATTCTCTGCT   2901
TGAACACAGT ATTCTCCCAG TCCACACCCA TCGCCAGTGT CTTTCTTTGG TGCCTTTCCT   2961
GTTCAGCATT CTCAGCCTGT GGCAGTGAAG AGAACCAACC TGCCACACGA CGAAAAGCTG   3021
CTAAATCTCC TTCTATTTTT TTAAAATCAC TAACATTATA TTGCAATGAG AGAAATTTTA   3081
AAAAGTCTCT ATTTAAATTC TTTTTTTAAA TTTCTCCTCA GTTGGTGTGT TTCCGGGATG   3141
TCTTATTTTT AGATGGTTAC ACTGTTAGAA CACTATTTTT CAGAATCTGA ATGTAATTTG   3201
TGTAATAAAG TGTTTTCAGA GCATT                                         3226
```

(2) INFORMATION FOR SEQ ID NO:11:

(i) SEQUENCE CHARACTERISTICS:
(A) LENGTH: 276 amino acids
(B) TYPE: amino acid
(D) TOPOLOGY: linear (ii) MOLECULE TYPE: protein -continued (xi) SEQUENCE DESCRIPTION: SEQ ID NO:11:

```
Met Ala Gly Arg Ala Arg Ser Gly Leu Leu Leu Leu Leu Leu Gly Leu
  1               5                  10                  15

Leu Ala Leu Gln Ser Ser Cys Leu Ala Phe Arg Ser Pro Leu Ser Val
             20                  25                  30

Phe Lys Arg Phe Lys Glu Thr Thr Arg Ser Phe Ser Asn Glu Cys Leu
         35                  40                  45

Gly Thr Ile Gly Pro Val Thr Pro Leu Asp Ala Ser Asp Phe Ala Leu
     50                  55                  60

Asp Ile Arg Met Pro Gly Val Thr Pro Lys Glu Ser Asp Thr Tyr Phe
 65                  70                  75                  80

Cys Met Ser Met Arg Leu Pro Val Asp Glu Glu Ala Phe Val Ile Asp
                 85                  90                  95

Phe Lys Pro Arg Ala Ser Met Asp Thr Val His His Met Leu Leu Phe
            100                 105                 110

Gly Cys Asn Met Pro Ser Ser Thr Gly Ser Tyr Trp Phe Cys Asp Glu
        115                 120                 125

Gly Thr Cys Thr Asp Lys Ala Asn Ile Leu Tyr Ala Trp Ala Arg Asn
    130                 135                 140

Ala Pro Pro Thr Arg Leu Pro Lys Gly Val Gly Phe Arg Val Gly Gly
145                 150                 155                 160

Glu Thr Gly Ser Lys Tyr Phe Val Leu Gln Val His Tyr Gly Asp Ile
                165                 170                 175

Ser Ala Phe Arg Asp Asn His Lys Asp Cys Ser Gly Val Ser Val His
            180                 185                 190

Leu Thr Arg Val Pro Gln Pro Leu Ile Ala Gly Met Tyr Leu Met Met
        195                 200                 205

Ser Val Asp Thr Val Ile Pro Pro Gly Glu Lys Val Val Asn Ala Asp
    210                 215                 220

Ile Ser Cys Gln Tyr Lys Met Tyr Pro Met His Val Phe Ala Tyr Arg
225                 230                 235                 240

Val His Thr His His Leu Gly Lys Val Val Ser Gly Tyr Arg Val Arg
                245                 250                 255

Asn Gly Gln Trp Thr Leu Ile Gly Arg Gln Asn Pro Gln Leu Pro Gln
            260                 265                 270

Ala Phe Tyr Pro
        275
```

(2) INFORMATION FOR SEQ ID NO:12:

(i) SEQUENCE CHARACTERISTICS:
(A) LENGTH: 315 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Rat (xi) SEQUENCE DESCRIPTION: SEQ ID NO:12:

```
GTGATTTCTA TTCACTGCTT TCCAAGCTGC TAGGAGAAAG GGAAGATGTT CATGTGCACA     60

AGTATAATCC TACAGAAAAG ACAGAATCTG GGTCAGACCT GGTAGCTGAG ATTGCAAACG    120

TGGTCCAGAA AAAGGACCTT GGTCGGTCTG ACGCCAGAGA AGGTGCAGAG CATGAGGAAT    180
```

-continued

```
GGGGTAATGC TATCCTAGTC AGAGACAGGA TCCACAGATT CCACCAGCTA GAGTCAACTC    240

TGAGGCCAGC TGAGAGCAGA GCTTTCTCGT TCCAGCAGCC TGGCGAAGGC CCTTGGGAAC    300

CAGAACCCTC AGGAG                                                     315
```

(2) INFORMATION FOR SEQ ID NO:13:

(i) SEQUENCE CHARACTERISTICS:
(A) LENGTH: 54 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Rat (xi) SEQUENCE DESCRIPTION: SEQ ID NO:13:

```
ATCATGACCG CAAGCTCGAG TCAAGTTCTG GAAGAGTCCT GGGAAGATTC CGAC           54
```

(2) INFORMATION FOR SEQ ID NO:14:

(i) SEQUENCE CHARACTERISTICS:
(A) LENGTH: 989 amino acids
(B) TYPE: amino acid
(C) STRANDEDNESS: single
(D) TOPOLOGY: linear (ii) MOLECULE TYPE: protein (vi) ORIGINAL SOURCE:
(A) ORGANISM: Bovine (xi) SEQUENCE DESCRIPTION: SEQ ID NO:14:

```
Met Ala Gly Xaa Phe Arg Ser Xaa Xaa Leu Leu Val Leu Leu Xaa Leu
1               5                   10                  15

Val Xaa Phe Pro Ser Gly Cys Val Gly Phe Arg Ser Pro Leu Ser Val
            20                  25                  30

Phe Lys Arg Phe Lys Glu Thr Thr Arg Ser Phe Ser Asn Glu Cys Leu
        35                  40                  45

Gly Thr Thr Arg Pro Val Ile Pro Ile Asp Ser Ser Asp Phe Ala Leu
    50                  55                  60

Asp Ile Arg Met Pro Gly Val Thr Pro Lys Gln Ser Asp Thr Tyr Phe
65                  70                  75                  80

Cys Met Ser Val Arg Leu Pro Met Asp Glu Glu Ala Phe Val Ile Asp
                85                  90                  95

Phe Lys Pro Arg Ala Ser Met Asp Thr Val His His Met Leu Leu Phe
            100                 105                 110

Gly Cys Asn Met Pro Ala Ser Thr Gly Asn Tyr Trp Phe Cys Asp Glu
        115                 120                 125

Gly Thr Cys Thr Asp Lys Ala Asn Ile Leu Tyr Ala Trp Ala Arg Asn
    130                 135                 140

Ala Pro Pro Thr Arg Leu Pro Lys Gly Val Gly Phe Arg Val Gly Gly
145                 150                 155                 160

Glu Thr Gly Ser Lys Tyr Phe Val Leu Gln Val His Tyr Gly Asp Ile
                165                 170                 175

Ser Ala Phe Arg Asp Asn His Lys Asp Cys Ser Gly Val Ser Leu His
            180                 185                 190

Leu Thr Arg Leu Pro Gln Pro Leu Ile Ala Gly Met Tyr Leu Met Met
        195                 200                 205
```

-continued

```
Ser Val Asp Thr Val Ile Pro Pro Gly Gly Lys Val Val Asn Ser Asp
    210                 215                 220

Ile Ser Cys His Tyr Lys Lys Tyr Pro Met His Val Phe Ala Tyr Arg
225                 230                 235                 240

Val His Thr His His Leu Gly Lys Val Val Ser Gly Tyr Arg Val Arg
                245                 250                 255

Asn Gly Gln Trp Thr Leu Ile Gly Arg Gln Ser Pro Gln Leu Pro Gln
            260                 265                 270

Ala Phe Tyr Pro Val Glu His Pro Val Asp Val Ser Phe Gly Asp Ile
        275                 280                 285

Leu Ala Ala Arg Cys Val Phe Thr Gly Glu Gly Arg Thr Glu Val Thr
    290                 295                 300

His Ile Gly Gly Thr Ser Ser Asp Glu Met Cys Asn Leu Tyr Ile Met
305                 310                 315                 320

Tyr Tyr Met Glu Ala Lys His Ala Val Ser Phe Met Thr Cys Thr Gln
                325                 330                 335

Asn Val Ala Pro Asp Ile Phe Arg Thr Ile Pro Pro Glu Ala Asn Ile
            340                 345                 350

Pro Ile Pro Val Lys Ser Asp Met Val Met Met Xaa Xaa Xaa Xaa His
        355                 360                 365

Gly His His Lys Glu Thr Glu Asn Lys Asp Lys Thr Ser Leu Leu Gln
    370                 375                 380

Gln Pro Lys Arg Glu Glu Glu Gly Val Leu Glu Gln Gly Asp Phe Tyr
385                 390                 395                 400

Ser Leu Leu Ser Lys Leu Leu Gly Glu Arg Glu Asp Val Val His Val
                405                 410                 415

His Lys Tyr Asn Pro Thr Glu Lys Ala Glu Ser Glu Ser Asp Leu Val
            420                 425                 430

Ala Glu Ile Ala Asn Val Val Gln Lys Lys Asp Leu Gly Arg Ser Asp
        435                 440                 445

Thr Arg Glu Ser Ala Glu Xaa Gln Glu Xaa Arg Gly Asn Ala Ile Leu
    450                 455                 460

Val Arg Asp Arg Ile His Lys Phe His Arg Leu Val Ser Thr Leu Arg
465                 470                 475                 480

Pro Ala Glu Ser Arg Val Leu Ser Leu Gln Gln Pro Leu Pro Gly Glu
                485                 490                 495

Gly Thr Trp Glu Pro Glu His Thr Gly Asp Phe His Val Glu Glu Ala
            500                 505                 510

Leu Asp Trp Pro Gly Val Tyr Leu Leu Pro Gly Gln Val Ser Gly Val
        515                 520                 525

Ala Leu Asp Pro Gln Asn Asn Leu Val Ile Phe His Arg Gly Asp His
    530                 535                 540

Val Trp Asp Gly Asn Ser Phe Asp Ser Lys Phe Val Tyr Gln Gln Arg
545                 550                 555                 560

Gly Leu Gly Pro Ile Glu Glu Asp Thr Ile Leu Val Ile Asp Pro Asn
                565                 570                 575

Asn Ala Ala Val Leu Gln Ser Ser Gly Lys Asn Leu Phe Tyr Leu Pro
            580                 585                 590

His Gly Leu Ser Ile Asp Lys Asp Gly Asn Tyr Trp Val Thr Asp Val
        595                 600                 605

Ala Leu His Gln Val Phe Lys Leu Asp Pro Lys Ser Lys Glu Gly Pro
    610                 615                 620

Leu Leu Thr Leu Gly Arg Ser Met Gln Pro Gly Ser Asp Gln Asn His
```

-continued

```
625                 630                 635                 640

Phe Cys Gln Pro Thr Asp Val Ala Val Asp Pro Asp Thr Gly Thr Ile
                645                 650                 655

Tyr Val Ser Asp Gly Tyr Cys Asn Ser Arg Leu Val Gln Phe Ser Pro
            660                 665                 670

Ser Gly Lys Phe Ile Thr His Trp Gly Glu Ala Ser Leu Glu Ser Ser
        675                 680                 685

Pro Lys Pro Gly Gln Phe Arg Val Pro His Ser Leu Ala Leu Val Pro
    690                 695                 700

Pro Leu Gly Gln Leu Cys Val Ala Asp Arg Glu Asn Gly Arg Ile Gln
705                 710                 715                 720

Cys Phe Lys Thr Asp Thr Lys Glu Phe Val Arg Glu Ile Lys His Pro
                725                 730                 735

Ser Phe Gly Arg Asn Val Phe Ala Ile Ser Tyr Ile Pro Xaa Gly Leu
            740                 745                 750

Leu Phe Ala Val Asn Gly Lys Pro Tyr Phe Glu Asp Gln Glu Pro Val
        755                 760                 765

Gln Gly Phe Val Met Asn Phe Ser Ser Gly Glu Ile Ile Asp Val Phe
    770                 775                 780

Lys Pro Val Arg Lys His Phe Asp Met Pro His Asp Ile Ala Ala Ser
785                 790                 795                 800

Glu Asp Gly Thr Val Tyr Val Gly Asp Ala His Thr Asn Thr Val Trp
                805                 810                 815

Lys Phe Thr Ser Thr Glu Lys Met Glu His Arg Ser Val Lys Lys Ala
            820                 825                 830

Gly Ile Glu Val Gln Glu Ile Lys Glu Ser Glu Ala Val Val Glu Thr
        835                 840                 845

Lys Met Xaa Xaa Glu Asn Lys Pro Ala Ser Ser Glu Leu Gln Lys Ile
    850                 855                 860

Gln Glu Lys Gln Lys Leu Val Lys Glu Pro Gly Ser Gly Val Pro Ala
865                 870                 875                 880

Val Leu Ile Thr Thr Leu Leu Val Ile Pro Val Val Val Leu Leu Ala
                885                 890                 895

Ile Ala Leu Phe Ile Arg Trp Lys Lys Ser Arg Xaa Ala Phe Gly Asp
            900                 905                 910

Ser Glu Arg Lys Leu Glu Ala Ser Ser Gly Arg Val Leu Gly Arg Leu
        915                 920                 925

Arg Gly Lys Gly Gly Gly Gly Leu Asn Leu Gly Asn Phe Phe Ala Ser
    930                 935                 940

Arg Lys Gly Tyr Ser Arg Lys Gly Phe Asp Arg Leu Ser Thr Glu Gly
945                 950                 955                 960

Ser Asp Gln Glu Lys Xaa Asp Glu Xaa Asp Ala Ser Glu Ser Glu Glu
                965                 970                 975

Glu Tyr Ser Ala Pro Pro Pro Ala Pro Ala Pro Ser Ser
            980                 985
```

(2) INFORMATION FOR SEQ ID NO:15:

(i) SEQUENCE CHARACTERISTICS:
- (A) LENGTH: 404 amino acids
- (B) TYPE: amino acid
- (C) STRANDEDNESS: single
- (D) TOPOLOGY: linear (ii) MOLECULE TYPE: protein -continued (vi) ORIGINAL SOURCE:
(A) ORGANISM: Frog (xi) SEQUENCE DESCRIPTION: SEQ ID NO:15:

```
Met Ala Ser Xaa Leu Ser Ser Ser Xaa Phe Leu Val Leu Xaa Xaa Phe
1               5                   10                  15

Leu Leu Phe Gln Asn Ser Cys Tyr Cys Phe Arg Ser Pro Leu Ser Val
            20                  25                  30

Phe Lys Arg Tyr Glu Glu Ser Thr Arg Ser Leu Ser Asn Asp Cys Leu
        35                  40                  45

Gly Thr Thr Arg Pro Val Met Ser Pro Gly Ser Ser Asp Tyr Thr Leu
    50                  55                  60

Asp Ile Arg Met Pro Gly Val Thr Pro Thr Glu Ser Asp Thr Tyr Leu
65                  70                  75                  80

Cys Lys Ser Tyr Arg Leu Pro Val Asp Asp Glu Ala Tyr Val Val Asp
                85                  90                  95

Phe Arg Pro His Ala Asn Met Asp Thr Ala His His Met Leu Leu Phe
            100                 105                 110

Gly Cys Asn Ile Pro Ser Ser Thr Gly Asp Tyr Trp Asp Cys Ser Ala
        115                 120                 125

Gly Thr Met Asp Lys Ser Ser Ile Met Tyr Ala Trp Ala Lys Asn Ala
    130                 135                 140

Pro Pro Thr Lys Leu Pro Glu Gly Val Gly Phe Arg Val Gly Gly Lys
145                 150                 155                 160

Ser Gly Ser Arg Tyr Phe Val Leu Gln Val His Tyr Gly Asn Val Lys
                165                 170                 175

Ala Phe Gln Asp Lys His Lys Asp Thr Gly Val Thr Val Arg Val Thr
            180                 185                 190

Pro Glu Lys Gln Pro Gln Ile Ala Gly Ile Tyr Leu Ser Met Ser Val
        195                 200                 205

Asp Thr Val Ile Pro Pro Gly Glu Glu Ala Val Asn Ser Asp Ile Ala
    210                 215                 220

Cys Leu Tyr Asn Arg Pro Thr Ile His Pro Phe Ala Tyr Arg Val His
225                 230                 235                 240

Thr His Gln Leu Gly Gln Val Val Ser Gly Phe Arg Val Arg His Gly
                245                 250                 255

Lys Trp Ser Leu Ile Gly Arg Gln Ser Pro Gln Leu Pro Gln Ala Phe
            260                 265                 270

Val Pro Val Glu His Pro Val Glu Ile Ser Pro Gly Asp Ile Ile Ala
        275                 280                 285

Thr Arg Cys Leu Phe Thr Gly Lys Gly Arg Thr Ser Ala Thr Tyr Ile
    290                 295                 300

Gly Gly Thr Ser Asn Asp Glu Met Cys Asn Leu Tyr Ile Met Tyr Tyr
305                 310                 315                 320

Met Asp Ala Ala His Ala Thr Ser Tyr Met Thr Cys Val Gln Thr Gly
                325                 330                 335

Glu Pro Lys Leu Phe Gln Asn Ile Pro Glu Ile Ala Asn Val Pro Ile
            340                 345                 350

Pro Val Ser Pro Asp Met Met Met Met Xaa Xaa Met Gly His Gly His
        355                 360                 365

His His Thr Glu Ala Glu Pro Glu Lys Asn Thr Gly Leu Gln Gln Pro
    370                 375                 380

Lys Arg Glu Glu Glu Glu Val Leu Asp Gln Gly Leu Ile Thr Leu Gly
385                 390                 395                 400
```

-continued

Asp Ser Ala Val (2) INFORMATION FOR SEQ ID NO:16:

(i) SEQUENCE CHARACTERISTICS:
(A) LENGTH: 989 amino acids
(B) TYPE: amino acid
(C) STRANDEDNESS: single
(D) TOPOLOGY: linear (ii) MOLECULE TYPE: protein (vi) ORIGINAL SOURCE:
(A) ORGANISM: Frog (xi) SEQUENCE DESCRIPTION: SEQ ID NO:16:

```
Met Asp Met Ala Ser Xaa Leu Ile Ser Ser Xaa Leu Leu Val Leu Xaa
1               5                   10                  15

Xaa Phe Leu Ile Phe Gln Asn Ser Cys Tyr Cys Phe Arg Ser Pro Leu
            20                  25                  30

Ser Val Phe Lys Arg Tyr Glu Glu Ser Thr Arg Ser Leu Ser Asn Asp
        35                  40                  45

Cys Leu Gly Thr Thr Arg Pro Val Met Ser Pro Gly Ser Ser Asp Tyr
    50                  55                  60

Thr Leu Asp Ile Arg Met Pro Gly Val Thr Pro Thr Glu Ser Asp Thr
65                  70                  75                  80

Tyr Leu Cys Lys Ser Tyr Arg Leu Pro Val Asp Asp Glu Ala Tyr Val
                85                  90                  95

Val Asp Tyr Arg Pro His Ala Asn Met Asp Thr Ala His His Met Leu
            100                 105                 110

Leu Phe Gly Cys Asn Val Pro Ser Ser Thr Gly Asp Tyr Trp Asp Cys
        115                 120                 125

Ser Ala Gly Thr Cys Asn Asp Lys Ser Ser Ile Met Tyr Ala Trp Ala
    130                 135                 140

Lys Asn Ala Pro Pro Thr Lys Leu Pro Glu Gly Val Gly Phe Gln Val
145                 150                 155                 160

Gly Gly Lys Ser Gly Ser Arg Tyr Phe Val Leu Gln Val His Tyr Gly
                165                 170                 175

Asp Val Lys Ala Phe Gln Asp Lys His Lys Asp Thr Gly Val Thr Val
            180                 185                 190

Arg Ile Thr Pro Glu Lys Gln Pro Leu Ile Ala Gly Ile Tyr Leu Ser
        195                 200                 205

Met Ser Leu Asn Thr Val Val Pro Pro Gly Gln Glu Val Val Asn Ser
    210                 215                 220

Asp Ile Ala Cys Leu Tyr Asn Arg Pro Thr Ile His Pro Phe Ala Tyr
225                 230                 235                 240

Arg Val His Thr His Gln Leu Gly Gln Val Val Ser Gly Phe Arg Val
                245                 250                 255

Arg His Gly Lys Trp Thr Leu Ile Gly Arg Gln Ser Pro Gln Leu Pro
            260                 265                 270

Gln Ala Phe Tyr Pro Val Glu His Pro Leu Glu Ile Ser Pro Gly Asp
        275                 280                 285

Ile Ile Ala Thr Arg Leu Phe Thr Gly Lys Gly Arg Met Ser Ala Thr
    290                 295                 300

Tyr Ile Gly Gly Thr Ala Lys Asp Glu Met Cys Asn Leu Tyr Ile Met
305                 310                 315                 320
```

-continued

```
Tyr Tyr Met Asp Ala Ala His Ala Thr Ser Tyr Met Thr Cys Val Gln
                325                 330                 335

Thr Gly Asn Pro Lys Leu Phe Glu Asn Ile Pro Glu Ile Ala Asn Val
            340                 345                 350

Pro Ile Pro Val Ser Pro Asp Met Met Met Met Met Met Met Gly His
        355                 360                 365

Gly His His His Thr Glu Ala Glu Ala Glu Thr Asn Thr Ala Leu Gln
    370                 375                 380

Gln Pro Lys Arg Glu Glu Glu Glu Val Leu Asn Gln Xaa Xaa Xaa Xaa
385                 390                 395                 400

Xaa Xaa Xaa Xaa Xaa Xaa Xaa Xaa Xaa Xaa Xaa Xaa Xaa Xaa Xaa Xaa
                405                 410                 415

Xaa Xaa Xaa Xaa Xaa Xaa Xaa Xaa Xaa Xaa Xaa Xaa Xaa Xaa Xaa Xaa
            420                 425                 430

Xaa Xaa Xaa Xaa Xaa Xaa Xaa Xaa Xaa Xaa Xaa Xaa Xaa Xaa Xaa Xaa
        435                 440                 445

Xaa Xaa Xaa Xaa Xaa Xaa Xaa Xaa Xaa Xaa Xaa Xaa Xaa Xaa Xaa Xaa
    450                 455                 460

Xaa Xaa Xaa Xaa Xaa Xaa Xaa Xaa Xaa Xaa Xaa Xaa Xaa Xaa Xaa Xaa
465                 470                 475                 480

Xaa Xaa Xaa Xaa Xaa Xaa Xaa Xaa Xaa Xaa Xaa Xaa Xaa Xaa Xaa Xaa
                485                 490                 495

Xaa Xaa Xaa Xaa Xaa Xaa Xaa Xaa Xaa Asp Val His Leu Glu Glu Asp
            500                 505                 510

Thr Asp Trp Pro Gly Val Asn Leu Lys Val Gly Gln Val Ser Gly Leu
        515                 520                 525

Ala Leu Asp Pro Lys Asn Asn Leu Val Ile Phe His Arg Gly Asp His
    530                 535                 540

Val Trp Asp Glu Asn Ser Phe Asp Arg Asn Phe Val Tyr Gln Gln Arg
545                 550                 555                 560

Gly Ile Gly Pro Ile Gln Glu Ser Thr Ile Leu Val Val Asp Pro Asn
                565                 570                 575

Thr Ser Lys Val Leu Lys Ser Thr Gly Gln Asn Leu Phe Phe Leu Pro
            580                 585                 590

His Gly Leu Thr Ile Asp Arg Asp Gly Asn Tyr Trp Val Thr Asp Val
        595                 600                 605

Ala Leu His Gln Val Phe Lys Xaa Val Gly Ala Glu Lys Glu Thr Pro
    610                 615                 620

Leu Leu Val Leu Gly Arg Ala Phe Gln Pro Gly Ser Asp Arg Lys His
625                 630                 635                 640

Phe Cys Gln Pro Thr Asp Val Ala Val Asp Pro Ile Thr Gly Asn Phe
                645                 650                 655

Phe Val Ala Asp Gly Tyr Cys Asn Ser Arg Ile Met Gln Phe Ser Pro
            660                 665                 670

Asn Gly Met Phe Ile Met Gln Trp Gly Glu Glu Thr Ser Ser Asn Leu
        675                 680                 685

Pro Arg Pro Gly Gln Phe Arg Ile Pro His Ser Leu Thr Met Ile Ser
    690                 695                 700

Asp Gln Gly Gln Leu Cys Val Ala Asp Arg Glu Asn Gly Arg Ile Gln
705                 710                 715                 720

Cys Phe His Ala Lys Thr Gly Glu Phe Val Lys Gln Ile Lys His Gln
                725                 730                 735

Glu Phe Gly Arg Glu Val Phe Ala Val Ser Tyr Ala Pro Gly Gly Val
```

-continued

```
            740                 745                 750

Leu Tyr Ala Val Asn Gly Lys Pro Tyr Tyr Gly Asp Ser Thr Pro Val
        755                 760                 765

Gln Gly Phe Met Ile Asn Phe Ser Asn Gly Asp Ile Leu Asp Thr Phe
    770                 775                 780

Ile Pro Ala Arg Lys Asn Phe Glu Met Pro His Asp Ile Ala Ala Gly
785                 790                 795                 800

Asp Asp Gly Thr Val Tyr Val Gly Asp Ala His Ala Asn Ala Val Trp
                805                 810                 815

Lys Phe Xaa Ser Pro Ser Lys Ala Glu His Arg Ser Val Lys Lys Ala
            820                 825                 830

Gly Ile Glu Val Glu Glu Ile Thr Glu Thr Glu Xaa Ile Phe Glu Thr
        835                 840                 845

His Met Arg Ser Arg Pro Lys Thr Asn Glu Ser Val Gly Gln Gln Thr
    850                 855                 860

Gln Glu Lys Pro Ser Val Val Gln Glu Ser Ser Ala Gly Val Ser Phe
865                 870                 875                 880

Val Leu Ile Ile Thr Leu Leu Ile Ile Pro Val Val Val Leu Ile Ala
                885                 890                 895

Ile Ala Ile Phe Ile Arg Trp Arg Lys Val Arg Met Tyr Gly Gly Asp
            900                 905                 910

Ile Gly His Lys Ser Glu Ser Ser Ser Gly Gly Ile Leu Gly Lys Leu
        915                 920                 925

Arg Gly Lys Gly Ser Gly Gly Leu Asn Leu Gly Thr Phe Phe Ala Thr
    930                 935                 940

His Lys Gly Tyr Ser Arg Lys Gly Phe Asp Arg Leu Ser Thr Glu Gly
945                 950                 955                 960

Ser Asp Gln Gln Lys Asp Asp Asp Asp Gly Ser Asp Ser Glu Glu Glu
                965                 970                 975

Tyr Ser Ala Pro Pro Ile Pro Pro Val Xaa Ser Ser Ser
            980                 985
```

(2) INFORMATION FOR SEQ ID NO:17:

(i) SEQUENCE CHARACTERISTICS:
(A) LENGTH: 989 amino acids
(B) TYPE: amino acid
(C) STRANDEDNESS: single
(D) TOPOLOGY: linear (ii) MOLECULE TYPE: protein (vi) ORIGINAL SOURCE:
(A) ORGANISM: Rat (xi) SEQUENCE DESCRIPTION: SEQ ID NO:17:

```
Met Ala Gly Arg Ala Arg Ser Gly Leu Leu Leu Leu Leu Leu Gly Leu
1               5                   10                  15

Leu Ala Leu Gln Ser Ser Cys Leu Ala Phe Arg Ser Pro Leu Ser Val
            20                  25                  30

Phe Lys Arg Phe Lys Glu Thr Thr Arg Ser Phe Ser Asn Glu Cys Leu
        35                  40                  45

Gly Thr Ile Gly Pro Val Thr Pro Leu Asp Ala Ser Asp Phe Ala Leu
    50                  55                  60

Asp Ile Arg Met Pro Gly Val Thr Pro Lys Glu Ser Asp Thr Tyr Phe
65                  70                  75                  80

Cys Met Ser Met Arg Leu Pro Val Asp Glu Glu Ala Phe Val Ile Asp
```

-continued

```
                85                  90                  95

Phe Lys Pro Arg Ala Ser Met Asp Thr Val His His Met Leu Leu Phe
            100                 105                 110

Gly Cys Asn Met Pro Ser Ser Thr Gly Ser Tyr Trp Phe Cys Asp Glu
        115                 120                 125

Gly Thr Cys Thr Asp Lys Ala Asn Ile Leu Tyr Ala Trp Ala Arg Asn
    130                 135                 140

Ala Pro Pro Thr Arg Leu Pro Lys Gly Val Gly Phe Arg Val Gly Gly
145                 150                 155                 160

Glu Thr Gly Ser Lys Tyr Phe Leu Val Leu Gln Val His Tyr Gly Asp
                165                 170                 175

Ile Ser Ala Phe Arg Asp Asn His Lys Asp Cys Ser Gly Val Ser Val
            180                 185                 190

His Leu Thr Arg Val Pro Gln Pro Leu Ile Ala Gly Met Tyr Leu Met
        195                 200                 205

Met Ser Val Asp Thr Val Ile Pro Pro Gly Glu Lys Val Val Asn Ala
    210                 215                 220

Asp Ile Ser Cys Gln Tyr Lys Met Tyr Pro Met His Val Phe Ala Tyr
225                 230                 235                 240

Arg Val His Thr His His Leu Gly Lys Val Val Ser Gly Tyr Arg Val
                245                 250                 255

Arg Asn Gly Gln Trp Thr Leu Ile Gly Arg Gln Asn Pro Gln Leu Pro
            260                 265                 270

Gln Ala Phe Tyr Pro Val Glu His Pro Val Asp Val Thr Phe Gly Asp
        275                 280                 285

Ile Leu Ala Ala Arg Cys Val Phe Thr Gly Glu Gly Arg Thr Glu Ala
    290                 295                 300

Thr His Ile Gly Gly Thr Ser Ser Asp Glu Met Cys Asn Leu Tyr Ile
305                 310                 315                 320

Met Tyr Tyr Met Glu Ala Lys Tyr Ala Leu Ser Phe Met Thr Cys Thr
                325                 330                 335

Lys Asn Val Ala Pro Asp Met Phe Arg Thr Ile Pro Ala Glu Ala Asn
            340                 345                 350

Ile Pro Ile Pro Val Lys Pro Asp Met Val Met Met Xaa Xaa Xaa Xaa
        355                 360                 365

His Gly His His Lys Glu Ala Glu Asn Lys Glu Lys Ser Ala Leu Met
    370                 375                 380

Gln Gln Pro Lys Gln Gly Glu Glu Glu Val Leu Glu Gln Gly Asp Phe
385                 390                 395                 400

Tyr Ser Leu Leu Ser Lys Leu Leu Gly Glu Arg Glu Asp Xaa Val His
                405                 410                 415

Val His Lys Tyr Asn Pro Thr Glu Lys Thr Glu Ser Gly Ser Asp Leu
            420                 425                 430

Val Ala Glu Ile Ala Asn Val Val Gln Lys Lys Asp Leu Gly Arg Ser
        435                 440                 445

Asp Ala Arg Glu Gly Ala Glu His Glu Glu Xaa Trp Gly Asn Ala Ile
    450                 455                 460

Leu Val Arg Asp Arg Ile His Arg Phe His Gln Leu Glu Ser Thr Leu
465                 470                 475                 480

Arg Pro Ala Glu Ser Arg Ala Phe Ser Phe Gln Gln Xaa Xaa Pro Gly
                485                 490                 495

Glu Gly Pro Trp Glu Pro Glu Pro Ser Gly Asp Phe His Val Glu Glu
            500                 505                 510
```

-continued

```
Glu Leu Asp Trp Pro Gly Val Tyr Leu Leu Pro Gly Gln Val Ser Gly
        515                 520                 525

Val Ala Leu Asp Ser Lys Asn Asn Leu Val Ile Phe His Arg Gly Asp
    530                 535                 540

His Val Trp Asp Gly Asn Ser Phe Asp Ser Lys Phe Val Tyr Gln Gln
545                 550                 555                 560

Arg Gly Leu Gly Pro Ile Glu Glu Asp Thr Ile Leu Val Ile Asp Pro
                565                 570                 575

Asn Asn Ala Glu Ile Leu Gln Ser Ser Gly Lys Asn Leu Phe Tyr Leu
            580                 585                 590

Pro His Gly Leu Ser Ile Asp Thr Asp Gly Asn Tyr Trp Val Thr Asp
        595                 600                 605

Val Ala Leu His Gln Val Phe Lys Leu Asp Pro His Ser Lys Glu Gly
    610                 615                 620

Pro Leu Leu Ile Leu Gly Arg Ser Met Gln Pro Gly Ser Asp Gln Asn
625                 630                 635                 640

His Phe Cys Gln Pro Thr Asp Val Ala Val Glu Pro Ser Thr Gly Ala
                645                 650                 655

Val Phe Val Ser Asp Gly Tyr Cys Asn Ser Arg Ile Val Gln Phe Ser
            660                 665                 670

Pro Ser Gly Lys Phe Val Thr Gln Trp Gly Glu Glu Ser Ser Gly Ser
        675                 680                 685

Ser Pro Arg Pro Gly Gln Phe Ser Val Pro His Ser Leu Ala Leu Val
    690                 695                 700

Pro His Leu Asp Gln Leu Cys Val Ala Asp Arg Glu Asn Gly Arg Ile
705                 710                 715                 720

Gln Cys Phe Lys Thr Asp Lys Glu Phe Val Arg Glu Ile Lys His Ala
                725                 730                 735

Ser Phe Gly Arg Asn Val Phe Ala Ile Ser Tyr Ile Pro Xaa Gly Phe
            740                 745                 750

Leu Phe Ala Val Asn Gly Lys Pro Tyr Phe Gly Asp Gln Glu Pro Val
        755                 760                 765

Gln Gly Phe Val Met Asn Phe Ser Ser Gly Glu Ile Ile Asp Val Phe
    770                 775                 780

Lys Pro Val Arg Lys His Phe Asp Met Pro His Asp Ile Val Ala Ser
785                 790                 795                 800

Glu Asp Gly Thr Val Tyr Ile Gly Asp Ala His Thr Asn Thr Val Trp
                805                 810                 815

Lys Phe Thr Leu Thr Glu Lys Met Glu His Arg Ser Val Lys Lys Ala
            820                 825                 830

Gly Ile Glu Val Gln Glu Ile Lys Glu Ala Glu Ala Val Val Glu Pro
        835                 840                 845

Lys Val Xaa Xaa Glu Asn Lys Pro Thr Ser Ser Glu Leu Gln Lys Met
    850                 855                 860

Gln Glu Lys Gln Lys Leu Ser Thr Glu Pro Gly Ser Gly Val Ser Val
865                 870                 875                 880

Val Leu Ile Thr Thr Leu Leu Val Ile Pro Val Leu Val Leu Leu Ala
                885                 890                 895

Ile Val Met Phe Ile Arg Trp Lys Lys Ser Arg Xaa Ala Phe Gly Asp
            900                 905                 910

His Asp Arg Lys Leu Glu Ser Ser Ser Gly Arg Val Leu Gly Arg Phe
        915                 920                 925
```

-continued

```
Arg Gly Lys Gly Ser Gly Gly Leu Asn Leu Gly Asn Phe Phe Ala Ser
    930                 935                 940

Arg Lys Gly Tyr Ser Arg Lys Gly Phe Asp Arg Val Ser Thr Glu Gly
945                 950                 955                 960

Ser Asp Gln Glu Lys Xaa Asp Glu Asp Asp Gly Thr Glu Ser Glu Glu
                965                 970                 975

Glu Tyr Ser Ala Pro Leu Pro Lys Pro Ala Pro Ser Ser
            980                 985
```

(2) INFORMATION FOR SEQ ID NO:18:

(i) SEQUENCE CHARACTERISTICS:
(A) LENGTH: 5 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:18:

```
Ser Leu Ala Phe Gly
1               5
```

(2) INFORMATION FOR SEQ ID NO:19:

(i) SEQUENCE CHARACTERISTICS:
(A) LENGTH: 10 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:19:

```
CATCTGAAAC                                                          10
```

(2) INFORMATION FOR SEQ ID NO:20:

(i) SEQUENCE CHARACTERISTICS:
(A) LENGTH: 10 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:20:

```
ACTTTGGGCC                                                          10
```

(2) INFORMATION FOR SEQ ID NO:21:

(i) SEQUENCE CHARACTERISTICS:
(A) LENGTH: 1172 base pairs
(B) TYPE: nucleic acid
(C) STRANDEDNESS: single
(D) TOPOLOGY: linear (ii) MOLECULE TYPE: DNA (genomic)

(vi) ORIGINAL SOURCE:
(A) ORGANISM: Rat (xi) SEQUENCE DESCRIPTION: SEQ ID NO:21:

```
TGCATGTGTT TGCCTACAGA GTCCACACTC ACCATTTAGG TAAGGTGGTG AGCGGATACA     60

GAGTAAGAAA CGGACAGTGG ACACTGATTG GACGCCAGAA CCCCCAGCTG CCACAGGCTT    120

TCTACCCTGT GGAACACCCC GTTGATGTTA CTTTTGGTGA TATACTGGCA GCCAGATGTG    180
```

-continued

| | | | | | | |
|---|---|---|---|---|---|---|
| TGTTCACTGG | TGAAGGGAGG | ACAGAGGCCA | CCCATATCGG | CGGCACTTCT | AGTGACGAAA | 240 |
| TGTGTAACCT | GTACATCATT | GTATTACATG | GAAGCCAAAT | ATGCACTTTC | CTTCATGACC | 300 |
| TGTACAAAGA | ACGTGGCTCC | AGATATGTTC | AGAACTATCC | CAGCAGAGGC | CAATATCCCA | 360 |
| ATTCCTGTCA | AACCGGACAT | GGTTATGATG | CACGGGCATC | ACAAAGAAGC | AGAAAACAAA | 420 |
| GAAAAGAGTG | CTTTAATGCA | GCAGCCAAAA | CAGGGAGAGG | AAGAAGTATT | AGAGCAGGGT | 480 |
| GATTTCTATT | CACTGCTTTC | CAAGCTGCTA | GGAGAAAGGG | AAGATGTTCA | TGTGCACAAG | 540 |
| TATAATCCTA | CAGAAAAGAC | AGAATCTGGG | TCAGACCTGG | TAGCTGAGAT | TGCAAACGTG | 600 |
| GTCCAGAAAA | GGACCTTGGT | CGGTCTGACG | CCAGAGAAGG | TGCAGAGCAT | GAGGAATGGG | 660 |
| GTAATGCTAT | CCTAGTCAGA | GACAGGATCC | ACAGATTCCA | CCAGCTAGAG | TCAACTCTGA | 720 |
| GGCCAGCTGA | GAGCAGAGCT | TTCTCGTTCC | AGCAGCCTGG | CGAAGGCCCT | TGGGAACCAG | 780 |
| AACCCTCAGG | AGATTTCCAT | GTGGAAGAAG | AACTGGACTG | GCCTGGAGTG | TACTTGTTAC | 840 |
| CAGGCCAGGT | TTCTGGGGTG | GCCCTGGATT | CTAAGAATAA | CCTAGTGATT | TTCCACAGAG | 900 |
| GTGACCATGT | TTGGGATGGA | AACTCTTTTG | ACAGCAAGTT | TGTTTACCAG | CAAAGAGGTC | 960 |
| TTGGGCCAAT | TGAAGAAGAC | ACCATCCTGG | TCATTGACCC | AAATAATGCT | GAAATCCTCC | 1020 |
| AGTCCAGTGG | CAAGAACCTG | TTTTATTTAC | CACACGGCTT | GAGCATAGAT | ACAGATGGAA | 1080 |
| ATTATTGGGT | CACAGATGTG | GCTCTCCACC | AGGTGTTCAA | ATTGGACCCG | CATAGCAAAG | 1140 |
| AAGGCCCTCT | CTTAATTCTG | GGAAGGAGCA | TG | | | 1172 |